US011293868B2

(12) United States Patent
Harootunian et al.

(10) Patent No.: US 11,293,868 B2
(45) Date of Patent: Apr. 5, 2022

(54) RATIOMETRIC FLUORESCENCE IMAGING METHODS

(71) Applicant: Avelas Biosciences, Inc., La Jolla, CA (US)

(72) Inventors: Alec Harootunian, San Diego, CA (US); Jesus E. Gonzalez, Carlsbad, CA (US)

(73) Assignee: Avelas Biosciences, Inc., La Jolla, CA (US)

( * ) Notice: Subject to any disclaimer, the term of this patent is extended or adjusted under 35 U.S.C. 154(b) by 350 days.

(21) Appl. No.: 16/603,200

(22) PCT Filed: Apr. 5, 2018

(86) PCT No.: PCT/US2018/026336
§ 371 (c)(1),
(2) Date: Oct. 4, 2019

(87) PCT Pub. No.: WO2018/187629
PCT Pub. Date: Oct. 11, 2018

(65) Prior Publication Data
US 2020/0150041 A1    May 14, 2020

Related U.S. Application Data

(60) Provisional application No. 62/483,004, filed on Apr. 7, 2017.

(51) Int. Cl.
*G01N 21/64* (2006.01)
*G06T 7/136* (2017.01)
(Continued)

(52) U.S. Cl.
CPC ..... *G01N 21/6456* (2013.01); *A61B 1/00009* (2013.01); *A61K 38/03* (2013.01);
(Continued)

(58) Field of Classification Search
None
See application file for complete search history.

(56) References Cited

U.S. PATENT DOCUMENTS 4,496,542 A    1/1985  Skiles et al.
4,659,839 A    4/1987  Nicolotti et al.
(Continued)

FOREIGN PATENT DOCUMENTS

EP    2736533 A2    6/2014
JP    2001017379 A    1/2001
(Continued)

OTHER PUBLICATIONS

Ying, L., Ratiometric Analysis of Single-Molecule Fluorescence Resonance Energy Transfer Using Logical Combinations of Threshold Criteria: A Study of 12-mer DNA, J Phys Chem B, 104:5171-5178 (2000).
(Continued)

*Primary Examiner* — Nancy Bitar
(74) *Attorney, Agent, or Firm* — Goodwin Procter LLP

(57) ABSTRACT

Disclosed herein are ratiometric fluorescence imaging reagents, and image processing methods for using fluorescence ratio and intensity thresholds to detect and visualize regions of biological activity in biological specimens with improved accuracy.

15 Claims, 21 Drawing Sheets

(51) Int. Cl.
*A61B 1/00* (2006.01)
*A61K 38/03* (2006.01)
*G06T 7/00* (2017.01)

(52) U.S. Cl.
CPC .......... *G06T 7/0012* (2013.01); *G06T 7/136* (2017.01); *G01N 2021/6421* (2013.01); *G01N 2021/6441* (2013.01); *G06T 2207/20212* (2013.01); *G06T 2207/30024* (2013.01)

(56) References Cited

U.S. PATENT DOCUMENTS

| | | | |
|---|---|---|---|
| 6,516,217 | B1 | 2/2003 | Tsujita |
| 10,279,585 | B2* | 5/2019 | Hoover ............ B41J 2/04505 |
| 10,614,571 | B2* | 4/2020 | Unterer ............... G16Z 99/00 |
| 10,724,956 | B1* | 7/2020 | Bierdz ............. G01N 21/6428 |
| 2009/0017485 | A1 | 1/2009 | Yamada et al. |
| 2009/0226059 | A1* | 9/2009 | Levenson ............ G06T 7/143 382/128 |
| 2011/0049384 | A1 | 3/2011 | Yared et al. |
| 2012/0150043 | A1 | 6/2012 | Mahmood et al. |
| 2013/0221240 | A1 | 8/2013 | Kishima et al. |
| 2015/0050650 | A1 | 2/2015 | Seppo et al. |
| 2016/0110870 | A1* | 4/2016 | Moriyama ........ G01N 21/6428 382/128 |
| 2016/0160263 | A1 | 6/2016 | Whitney et al. |
| 2018/0024064 | A1* | 1/2018 | Ho ...................... G06T 7/0012 250/459.1 |

FOREIGN PATENT DOCUMENTS

| | | |
|---|---|---|
| JP | 2006189265 A | 7/2006 |
| JP | 2008268027 A | 11/2008 |
| WO | WO-2013019681 A2 | 2/2013 |
| WO | WO-2016148657 A1 | 9/2016 |
| WO | WO-2018187629 A1 | 10/2018 |

OTHER PUBLICATIONS

Gonzalez et al. Improved Indicators of Cell Membrane Potential that use Fluorescence Resonance Energy Transfer. Chemistry & Biology 4:269-277 (1997).
Hoshida et al. Imaging Steps of Lymphatic Metastasis Reveals That Vascular Endothelial Growth Factor-C Increases Metastasis by Increasing Delivery of Cancer Cells to Lymph Nodes: Therapeutic Implications. Cancer Res. 66:8065-75 (2006).
Jiang et al. Tumor imaging by means of proteolytic activation of cell-penetrating peptides. PNAS 101(51):17867-17872 (Dec. 21, 2004).
Jin et al. Visualization of HIV Protease Inhibition Using a Novel FRET Molecular Probe. Biotechnol Prog. 27(4):1107-1114 (2011).
Kaltenbronn et al. In: Proceedings 11th American Peptide Symposium. Netherlands: ESCOM Publishers; 1990: 969-970.
Lyon et al. Self-hydrolyzing maleimides improve the stability and pharmacological properties of antibody-drug conjugates. Nat. Biotechnol. 32(10):1059-1062 (2014).
Mizukami et al. Imaging of Caspase-3 Activation in HeLa Cells Stimulated with Etoposide Using a Novel Fluorescent Probe. FEBS Lett. 453:356-360 (1999).
Olson et al. In vivo characterization of activatable cell penetrating peptides for targeting protease activity in cancer. Integr Biol (Camb) 1(5-6):382-393 (2009).
PCT/US2018/026336 International Search Report and Written Opinion dated Jul. 24, 2018.
Scherer et al. Optical Imaging of Matrix Metalloproteinase-7 Activity In viva Using a Proteolytic Nanobeacon. Mol Imaging. 7(3):118-131 (2008).
Spatola. Chemistry Biochemistry Amino Acids and Proteins. Marcel Dekker De Inc. 7:267-357 (1983).
Whitney et al. Parallel in Vivo and in Vitro Selection Using Phage Display Identifies Proteasedependent Tumor-targeting Peptides. The Journal of Biological Chemistry 285(29):22532-22541 (2010).
Whitney et al. Ratiometric Activatable Cell-Penetrating Peptides Provide Rapid In vivo Readout of Thrombin Activation. Angew. Chem. Int. Ed. 52:325-330 (2013).

* cited by examiner

RATIOMETRIC FLUORESCENCE IMAGING METHODS

CROSS-REFERENCE

This application claims the benefit of U.S. Provisional Application No. 62/483,004, filed Apr. 7, 2017, which is incorporated herein by reference.

SUMMARY

Disclosed herein are methods for using fluorescence ratio and intensity thresholds to detect and visualize regions of biological activity in a biological specimen, the methods comprising: a) contacting the biological specimen with a ratiometric fluorescent indicator of the biological activity; b) capturing a first fluorescence intensity image at a first emission wavelength and a second fluorescence intensity image at a second emission wavelength for the biological specimen; c) combining the first fluorescence image and the second fluorescence image to create a fluorescence ratio image; d) processing the fluorescence ratio image, the first fluorescence intensity image, the second fluorescence intensity image, or any combination thereof, using an image analysis algorithm, wherein the image analysis algorithm: i) uses a fluorescence ratio threshold, a first fluorescence intensity threshold, a second fluorescence intensity threshold, or any combination thereof, to create a mask image of the fluorescence ratio image, a mask image of the first fluorescence intensity image, a mask image of the second fluorescence intensity image, or any combination thereof, ii) performs an AND logical operation on the mask image of the fluorescence ratio image, the mask image of the first fluorescence intensity image, the mask image of the second fluorescence intensity image, or any combination thereof, if two or more mask images have been created in step (i), and iii) provides a classification of the biological specimen as either positive or negative for the biological activity, wherein the classification is based on a detection of a region of interest within the fluorescence ratio image, the first fluorescence intensity image, the second fluorescence intensity image, or any combination thereof, that exhibits a fluorescence ratio value or a fluorescence intensity value that exceeds the value of the fluorescence ratio threshold, the first fluorescence intensity threshold, the second fluorescence intensity threshold, or any combination thereof, and e) displaying the region of interest within the fluorescence ratio image, the first fluorescence intensity image, or the second fluorescence intensity image for a user, and optionally storing the classification result in a computer memory.

In some embodiments, the biological specimen is a cell sample, an ex vivo tissue sample, or an in vivo tissue sample. In some embodiments, the biological activity to be detected and visualized is correlated with a disease. In some embodiments, the disease is arthritis, atherosclerosis, cancer, pre-cancer, inflammation, or any combination thereof. In some embodiments, the cancer is breast cancer. In some embodiments, the biological activity to be detected and visualized is correlated with a malignant tissue or coagulation (blood clotting). In some embodiments, steps (b) to (e) are repeated two or more times at defined time intervals to provide a series of first fluorescence intensity images, second fluorescence intensity images, and fluorescence ratio images for monitoring a change in biological activity over time. In some embodiments, the display of the region of interest is provided in real time. In some embodiments, the display of the region of interest is used by a surgeon in an intraoperative setting to guide a surgical procedure. In some embodiments, the first fluorescence intensity image and the second fluorescence intensity image are captured using an endoscope, and the display of the region of interest is used to guide a positioning of the endoscope. In some embodiments, the ratiometric fluorescent indicator comprises a fluorescence donor moiety and a fluorescence acceptor moiety that are separated by a cleavable linker. In some embodiments, the fluorescence donor moiety and fluorescence acceptor moiety are Cy5 and Cy7 respectively. In some embodiments, the cleavable linker comprises a peptide linkage that is cleavable by a protease. In some embodiments, the protease is a metalloprotease, a serine protease, a threonine protease, or a cysteine protease. In some embodiments, the ratiometric fluorescent indicator comprises a molecule of Formula (I):

$$[D_A\text{-}c_A]\text{-}A\text{-}[c_M\text{-}M]\text{-}X\text{-}B\text{-}[c_B\text{-}D_B] \qquad \text{Formula (I)}$$

wherein X is a cleavable linker which is cleavable by a protease, A is a peptide with a sequence comprising 5 to 20 acidic amino acid residues, B is a peptide with a sequence comprising 5 to 20 basic amino acid residues, $c_A$, $c_B$, and $c_M$ each independently comprise 0-1 amino acid, M is a macromolecule, and $D_A$ and $D_B$ are a pair of acceptor and donor fluorescent moieties that are capable of undergoing fluorescence resonance energy transfer with the other; and wherein $[c_M\text{-}M]$ is bound to any position on A or X, $[D_A\text{-}c_A]$ is bound to any amino acid residue of A, and $[c_B\text{-}D_B]$ is bound to any amino acid residue of B. In some embodiments, the molecule of Formula (I) is SDM-25. In some embodiments, only a fluorescence ratio threshold is used to create a mask file.

Also disclosed herein are methods for automated optimization of fluorescence ratio and fluorescence intensity thresholds used to detect regions of biological activity in ratiometric fluorescence images of biological specimens, the methods comprising: a) providing a plurality of biological specimens; b) contacting each of the biological specimens with a ratiometric fluorescent indicator of the biological activity; c) capturing a first fluorescence intensity image at a first emission wavelength and a second fluorescence intensity image at a second emission wavelength for each of the biological specimens; d) combining the first fluorescence image and the second fluorescence image to create a fluorescence ratio image for each of the biological specimens; e) providing a starting value for a first fluorescence intensity threshold, a second fluorescence intensity threshold, a fluorescence ratio threshold, or any combination thereof; and f) for each of the biological specimens: i) processing the fluorescence ratio image, the first fluorescence intensity image, the second fluorescence intensity image, or any combination thereof, using an image analysis algorithm, wherein the image analysis algorithm: uses the fluorescence ratio threshold, the first fluorescence intensity threshold, the second fluorescence intensity threshold, or any combination thereof, to create a mask image of the fluorescence ratio image, a mask image of the first fluorescence intensity image, a mask image of the second fluorescence intensity image, or any combination thereof, performs an AND logical operation on the mask image of the fluorescence ratio image, the mask image of the first fluorescence intensity image, the mask image of the second fluorescence intensity image, or any combination thereof, if two or more mask images have been created in the previous step, optionally checks that a detected region of interest within the fluorescence ratio image, the first fluorescence intensity image, the second fluorescence intensity image, or any combination thereof, is greater than a specified minimum size, wherein the detected region of interest is a region that exhibits a fluorescence ratio or a fluorescence intensity value that exceeds the value of the fluorescence ratio threshold, the first fluorescence intensity threshold, the second fluorescence intensity threshold, or any combination thereof, and provides a classification of the biological specimen as positive for the biological activity if a region of interest has been detected, or provides a classification of the biological specimen as negative for the biological activity if no region of interest has been detected; ii) comparing the classification provided by the image analysis algorithm with a pathology lab test result for the biological specimen to determine whether the classification is a true positive, false negative, true negative, or false positive; iii) storing the true positive, false negative, true negative, or false positive classification result in a computer memory; and g) repeating step (f) with: i) an incrementally increased value of the first fluorescence intensity threshold, while the second fluorescence intensity threshold and the fluorescence ratio threshold are held fixed until all of the biological specimens are classified as negative by the image processing algorithm, or ii) an incrementally increased value of the second fluorescence intensity threshold, while the first fluorescence intensity threshold and the fluorescence ratio threshold are held fixed until all of the biological specimens are classified as negative by the image processing algorithm, or iii) an incrementally increased value of the fluorescence ratio threshold, while the first fluorescence intensity threshold and the second fluorescence intensity threshold are held fixed until all of the biological specimens are classified as negative by the image processing algorithm; h) calculating a receiver operator characteristic (ROC) curve using the stored classification results for each set of fluorescence ratio threshold, first fluorescence intensity threshold, and second fluorescence intensity threshold values; and i) comparing the area under the ROC curve for each set of fluorescence ratio threshold, first fluorescence intensity threshold, and second fluorescence intensity threshold values to determine an optimal setting for the fluorescence ratio threshold, the first fluorescence intensity threshold, the second fluorescence intensity threshold, or any combination thereof.

In some embodiments, the biological specimen is a cell sample, an ex vivo tissue sample, or an in vivo tissue sample. In some embodiments, the biological activity to be detected is correlated with a disease. In some embodiments, the disease is arthritis, atherosclerosis, cancer, pre-cancer, inflammation, or any combination thereof. In some embodiments, the cancer is breast cancer. In some embodiments, the biological activity to be detected and visualized is correlated with a malignant tissue or coagulation (blood clotting). In some embodiments, the ratiometric fluorescent indicator comprises a fluorescence donor moiety and a fluorescence acceptor moiety that are separated by a cleavable linker. In some embodiments, the fluorescence donor moiety and fluorescence acceptor moiety are Cy5 and Cy7 respectively. In some embodiments, the cleavable linker comprises a peptide linkage that is cleavable by a protease. In some embodiments, the protease is a metalloprotease, a serine protease, a threonine protease, or a cysteine protease. In some embodiments, the ratiometric fluorescence indicator is SDM-25 labeled with Cy5 and Cy7.

Disclosed herein are ratiometric fluorescence imaging methods for detecting regions of biological activity in a biological specimen, the methods comprising: a) contacting a biological specimen with a ratiometric fluorescent indicator of the biological activity; b) illuminating the biological specimen with excitation light of a first excitation wavelength; c) capturing a first fluorescence intensity image of the biological specimen at a first emission wavelength; d) subsequently or concurrently capturing a second fluorescence intensity image of the biological specimen at a second emission wavelength; and e) providing image processing software for combining the first fluorescence intensity image and the second fluorescence intensity image to create a fluorescence ratio image, wherein an image processing algorithm is used to detect or display a region of interest within the fluorescence ratio image of the biological specimen that exhibits the biological activity, wherein a region of interest comprises a region of the ratio image that exhibits a fluorescence ratio value, a first fluorescence intensity value, a second fluorescence intensity value, or any combination thereof, that exceeds the value of a first fluorescence intensity threshold, a second fluorescence intensity threshold, a fluorescence ratio threshold, or any combination thereof.

In some embodiments, the first and second fluorescence intensity images are captured of an in vitro biological specimen. In some embodiments, the first and second fluorescence intensity images are captured of an in vivo biological specimen. In some embodiments, the biological specimen is a cell sample, an ex vivo tissue sample, or an in vivo tissue sample. In some embodiments, the ratiometric fluorescent indicator is a molecule of Formula (I):

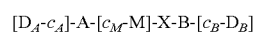

$$[D_A\text{-}c_A]\text{-}A\text{-}[c_M\text{-}M]\text{-}X\text{-}B\text{-}[c_B\text{-}D_B] \qquad \text{Formula (I)}$$

wherein X is a cleavable linker which is cleavable by a protease, A is a peptide with a sequence comprising 5 to 20 acidic amino acid residues, B is a peptide with a sequence comprising 5 to 20 basic amino acid residues, $c_A$, $c_B$, and $c_M$ each independently comprise 0-1 amino acid, M is a macromolecule, and $D_A$ and $D_B$ are a pair of acceptor and donor fluorescent moieties that are capable of undergoing fluorescence resonance energy transfer with the other; and wherein $[c_M\text{-}M]$ is bound to any position on A or X, $[D_A\text{-}c_A]$ is bound to any amino acid residue of A, and $[c_B\text{-}D_B]$ is bound to any amino acid residue of B.

In some embodiments, A is a peptide with a sequence comprising 5 to 9 acidic amino acid residues. In some embodiments, A is a peptide with a sequence comprising 5 or 9 consecutive glutamate residues. In some embodiments, B is a peptide with a sequence comprising 7 to 9 basic amino acid residues. In some embodiments, B is a peptide with a sequence comprising 8 or 9 consecutive arginine residues. In some embodiments, A is a peptide sequence comprising 5 or 9 consecutive glutamate residues and B is a peptide sequence comprising 8 or 9 consecutive arginine residues. In some embodiments, A is a peptide sequence comprising 5 consecutive glutamate residues and B is a peptide sequence comprising 8 consecutive arginine residues. In some embodiments, $c_A$, $c_B$, and $c_M$ are each independently selected from a naturally-occurring amino acid or a non-naturally-occurring amino acid. In some embodiments, $c_A$, $c_B$, and $c_M$ are each independently selected from a D amino acid, an L amino acid, an α-amino acid, a β-amino acid, or a γ-amino acid. In some embodiments, $c_A$, $c_B$, and $c_M$ are each independently selected from any amino acid having a free thiol group, any amino acid having an N-terminal amine group, and any amino acid with a side chain capable of forming an oxime or hydrazone bond upon reaction with a hydroxylamine or hydrazine group. In some embodiments, $c_A$, $c_B$, and $c_M$ are each independently selected from D-cysteine, D-glutamate, lysine, and para-4-acetyl L-phenylalanine. In some embodiments, $c_B$ is any amino acid having a free thiol group. In some embodiments, $c_B$ is D-cysteine. In some embodiments, $c_A$ is any amino acid having an N-terminal amine group. In some embodiments, $c_A$ is D-glutamate. In some embodiments, $c_A$ is lysine. In some embodiments, $c_M$ is any amino acid with a side chain capable of forming an oxime or hydrazone bond upon reaction with a hydroxylamine or hydrazine group. In some embodiments, $c_M$ is para-4-acetyl L-phenylalanine. In some embodiments, X comprises a peptide linkage. In some embodiments, X comprises an amino acid sequence selected from: PLGLAG, PLG-C(me)-AG, RPLALWRS, ESPAYYTA, DPRSFL, PPRSFL, RLQLKL, and RLQLK(Ac)L. In some embodiments, X is cleavable by a metalloprotease. In some embodiments, the metalloprotease is a matrix metalloproteinase, an ADAM metalloproteinase, adamalysin, a pappalysin, a matrilysin, a neprilysin (neutral endopeptidase), an angiotensin-converting enzyme, a metallocarboxypeptidase, or a glutamate carboxypeptidase. In some embodiments, X comprises an amino acid sequence that is cleavable by MMP1, MMP2, MMP7, MMP9, MMP13, or MMP14. In some embodiments, X is cleavable by a serine or threonine protease. In some embodiments, the serine protease is an elastase, a coagulation factor (thrombin, factor VIIa, factor IXa, or factor Xa), a tissue-type plasminogen activator, a urokinase-type plasminogen activator, plasmin, testisin, corin, a tissue or plasma kallikrein, a tryptase, or a dipeptidyl peptidase. In some embodiments, X is cleavable by a cysteine protease. In some embodiments, the cysteine protease is cathepsin B, cathepsin K, cathepsin S, cathepsin L, a caspase, or a legumain. In some embodiments, $D_A$ and $D_B$ are a pair of fluorescence acceptor and donor moieties that are capable of undergoing fluorescence resonance energy transfer from one to the other. In some embodiments, $D_A$ and $D_B$ are Cy5 and Cy7. In some embodiments, the first excitation wavelength is from about 610 nm to about 650 nm. In some embodiments, the first emission wavelength is from about 660 nm to about 720 nm. In some embodiments, the second emission wavelength is from about 760 nm to about 830 nm. In some embodiments, $D_A$ and $D_B$ are Cy5 and IR Dye750. In some embodiments, $D_A$ and $D_B$ are Cy5 and IR Dye800. In some embodiments, $D_A$ and $D_B$ are Cy5 and ICG. In some embodiments, steps (c) to (e) are repeated two or more times at defined time intervals to provide a series of fluorescence ratio images for monitoring changes in biological activity over time. In some embodiments, the first and second fluorescence intensity images are normalized by image exposure time prior to creation of the fluorescence ratio image. In some embodiments, the image processing algorithm comprises the use of a fluorescence ratio threshold, a first fluorescence intensity threshold, a second fluorescence intensity threshold, or any combination thereof, to detect the region of interest. In some embodiments, the image processing algorithm further comprises: (i) using the fluorescence ratio threshold, the first fluorescence intensity threshold, the second fluorescence intensity threshold, or any combination thereof, to create a mask image of the fluorescence ratio image, a mask image of the first fluorescence intensity image, a mask image of the second fluorescence intensity image, or any combination thereof, (ii) performing an AND logical operation on the mask image of the fluorescence ratio image, the mask image of the first fluorescence intensity image, the mask image of the second fluorescence intensity image, or any combination thereof, if two or more mask images have been created in step (i), and (iii) providing a classification of the biological specimen as positive for the biological activity if a region of interest has been detected, or providing a classification of the biological specimen as negative for the biological activity if no region of interest has been detected. In some embodiments, a mean fluorescence ratio or a mean fluorescence intensity value within a region of interest provides a qualitative measure of biological activity in the region of interest. In some embodiments, a mean fluorescence ratio or a mean fluorescence intensity value within a region of interest provides a quantitative measure of biological activity in the region of interest. In some embodiments, a detected region of interest is correlated with a cancerous biological activity. In some embodiments, the fluorescence ratio image provides a contrast ratio of at least 1.5:1 between cancerous and normal tissue. In some embodiments, the image processing algorithm further comprises checking that a detected region of interest is greater than a specified minimum size.

Disclosed herein are methods for performing a ratiometric fluorescence imaging-based diagnostic test for cancer, the methods comprising: a) contacting a biological specimen with a ratiometric fluorescent indicator; b) illuminating the biological specimen with excitation light of a first excitation wavelength; c) capturing a first fluorescence intensity image of the biological specimen at a first emission wavelength; d) subsequently or concurrently capturing a second fluorescence intensity image of the biological specimen at a second emission wavelength; and e) providing imaging software for combining the first fluorescence intensity image and the second fluorescence intensity image to create a fluorescence ratio image of the biological specimen, wherein an image processing algorithm is used to detect or display a region of interest within the fluorescence ratio image of biological specimen that is correlated with cancerous biological activity.

In some embodiments, the first fluorescence intensity image and the second fluorescence images are normalized by image exposure time prior to creation of the fluorescence ratio image. In some embodiments, the image processing algorithm comprises the use of a fluorescence ratio threshold, a first fluorescence intensity threshold, a second fluorescence intensity threshold, or any combination thereof, to detect the region of interest that is correlated with cancerous biological activity. In some embodiments, the image processing algorithm further comprises: (i) using the fluorescence ratio threshold, the first fluorescence intensity threshold, the second fluorescence intensity threshold, or any combination thereof, to create a mask image of the fluorescence ratio image, a mask image of the first fluorescence intensity image, a mask image of the second fluorescence intensity image, or any combination thereof, (ii) performing an AND logical operation on the mask image of the fluorescence ratio image, the mask image of the first fluorescence intensity image, the mask image of the second fluorescence intensity image, or any combination thereof, if two or more mask images have been created in step (i), (iii) optionally checking that a detected region of interest is greater than a specified minimum size, and (iv) providing a classification of the biological specimen as positive for the cancerous activity if a region of interest has been detected, or providing a classification of the biological specimen as negative for the cancerous activity if no region of interest has been detected. In some embodiments, the ratiometric fluorescent indicator is a molecule of Formula (I):

$$[D_A\text{-}c_A]\text{-}A\text{-}[c_M\text{-}M]\text{-}X\text{-}B\text{-}[c_B\text{-}D_B] \qquad \text{Formula (I)}$$

wherein X is a cleavable linker which is cleavable by a protease, A is a peptide with a sequence comprising 5 to 20 acidic amino acid residues, B is a peptide with a sequence comprising 5 to 20 basic amino acid residues, $c_A$, $c_B$, and $c_M$ each independently comprise 0-1 amino acid, M is a macromolecule, and $D_A$ and $D_B$ are a pair of acceptor and donor fluorescent moieties that are capable of undergoing fluorescence resonance energy transfer with the other; and wherein $[c_M\text{-}M]$ is bound to any position on A or X, $[D_A\text{-}c_A]$ is bound to any amino acid residue of A, and $[c_B\text{-}D_B]$ is bound to any amino acid residue of B. In some embodiments, the ratiometric fluorescent indicator is SDM-25 labeled with Cy 5 and Cy7. In some embodiments, the cancerous biological activity is associated with melanoma, non-melanoma skin cancer, lung cancer, breast cancer, prostate cancer, colorectal cancer, pancreatic, liver, ovarian, cervical, head and neck, lymph nodes, thyroid, glioma, gastrointestinal cancer, or sarcoma. In some embodiments, a patient is infused with the ratiometric fluorescent indicator and the method is used to detect breast cancer in post-excision surgical specimens. In some embodiments, the clinical sensitivity for diagnosis of cancer is greater than 80%. In some embodiments, the clinical specificity for diagnosis of cancer is greater than 80%. In some embodiments, a patient is infused with the ratiometric fluorescent indicator and the method is used intraoperatively to guide a surgical procedure. In some embodiments, the method provides a test result that is used by a physician or healthcare provider to make a diagnosis or treatment decision. In some embodiments, the test result is transmitted from a location where the method is performed to a location of the physician or healthcare provider.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A: Absorbance spectrum of 17.5 µg/mL SDM-25 (AVB-620) in 80%/20% PBS/acetonitrile from 500-800 nm. FIG. 2B: SDM-25 fluorescence emission spectra in TCNB buffer using 630 nm excitation and an emission wavelength range of 620-850 nm. The two samples were prepared with and without pre-incubation with MMP9. Representative spectra are shown (from six experiments). The fluorescence emission spectra were measured in a cuvette spectrofluorometer using 630 nm excitation light both before (red) and after (blue) treatment with the MMP9 protease. Before cleavage, Cy5 is quenched by Cy7, which re-emits the absorbed excitation light at 780 nm. After cleavage, Cy7 no longer quenches Cy5, resulting in an increase of the 670 nm Cy5 emission peak and a reduction of the Cy7 re-emission at 780 nm. The residual shoulder from 710 nm to 840 nm is largely due to Cy5 emission.

FIG. 3A: SDM-25 cleavage rate (nM cleaved per minute) in 25 paired human breast cancer patient tissue homogenates. Cancer-positive tumor tissue (red diamonds) and cancer-negative adjacent tissue (blue triangles) are shown. Paired samples are connected by lines. Paired t-test gave P<0.0001 for significant difference between tumor and normal. FIG. 3B: Scatter plot of the same data with mean±95% confidence level. FIG. 3C: shows the ROC curve for SDM-25 cleavage rate detection of tumor versus normal tissue.

FIG. 4A: homogenates from three representative human breast cancer samples and paired normal tissue, selected from the 25 patients for which data is presented in FIG. 3A-FIG. 3C, were analyzed on a 10% gelatin zymogram. Recombinant active MMP2 and MMP9 were shown as standards (2 ng per lane). FIG. 4B: ELISA quantification of six MMPs in five representative human breast cancer samples (labelled as (1)) and paired normal tissue (labelled as (2)), including the three pairs shown in FIG. 4A. Error bars are standard deviations. ND=not detectable.

FIG. 18A: Representative black and white dorsal mouse images with (right) and without (left) fluorescence ratio image superimposed showing high fluorescence ratio in the primary tumor in the mouse's ear. FIG. 18B: SDM-25 (AVB-620) generated fluorescence ratio values for cervical lymph nodes grouped by cancer status as determined from H&E histopathology. Cancer-positive (red diamonds) and cancer-negative (blue triangles) lymph nodes are shown. The black lines show the mean±95% confidence level.

FIG. 18C: Representative fluorescence ratio image of exposed lymph nodes, blended with a reflected light image, taken 6 hours after SDM-25 (AVB-620) administration. The ratio is displayed using an RGB scale where a high ratio is indicated by red and a low ratio is indicated by blue. Red and cyan arrows indicate cancer positive and negative lymph nodes respectively as determined by H&E staining. FIG. 18D: The kinetics for the development of the SDM-25 (AVB-620) in vivo diagnostic fluorescence signal is shown. Imaging was performed at time points ranging from 1 hour to 48 hours after administration. Cancer-positive (red diamonds) and cancer-negative (blue triangles) lymph nodes are shown. The number of measurements (N) per data point ranged from 3 to 24, and the error bars indicate standard deviations.

DETAILED DESCRIPTION

Figure 1:
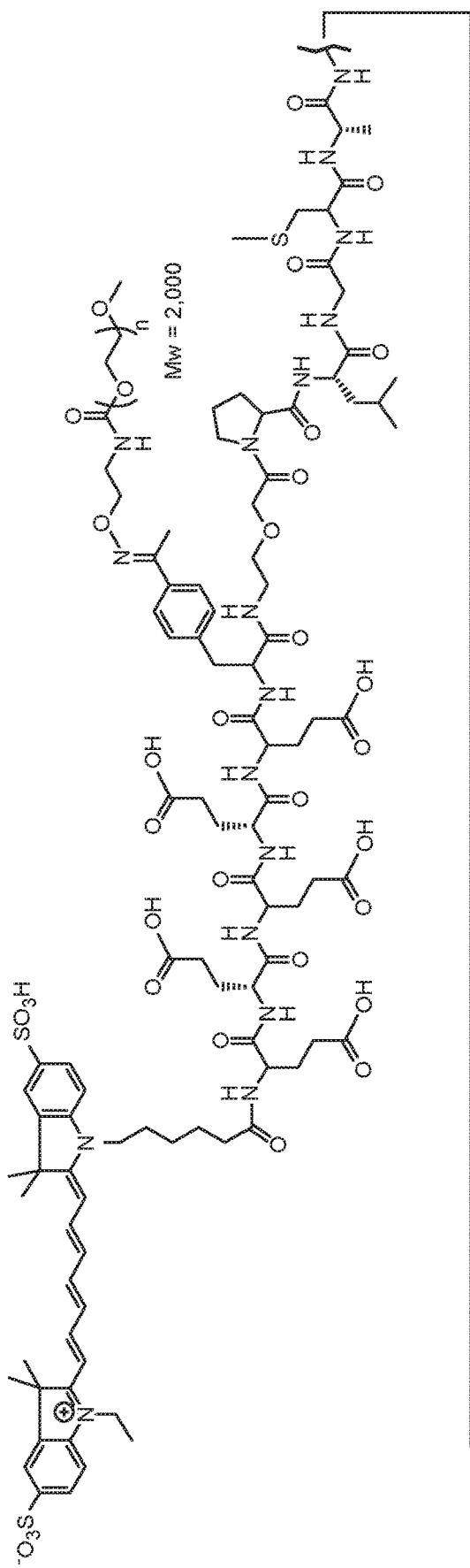
FIG. 1 illustrates the structure of one embodiment of a selective delivery molecule (SDM) (or activatable cell-penetrating peptide (ACPP)) comprising a Cy5 fluorescence donor and a Cy7 fluorescence quencher. The structure shown in FIG. 1 is the SDM-25 molecule.
Figure 1:
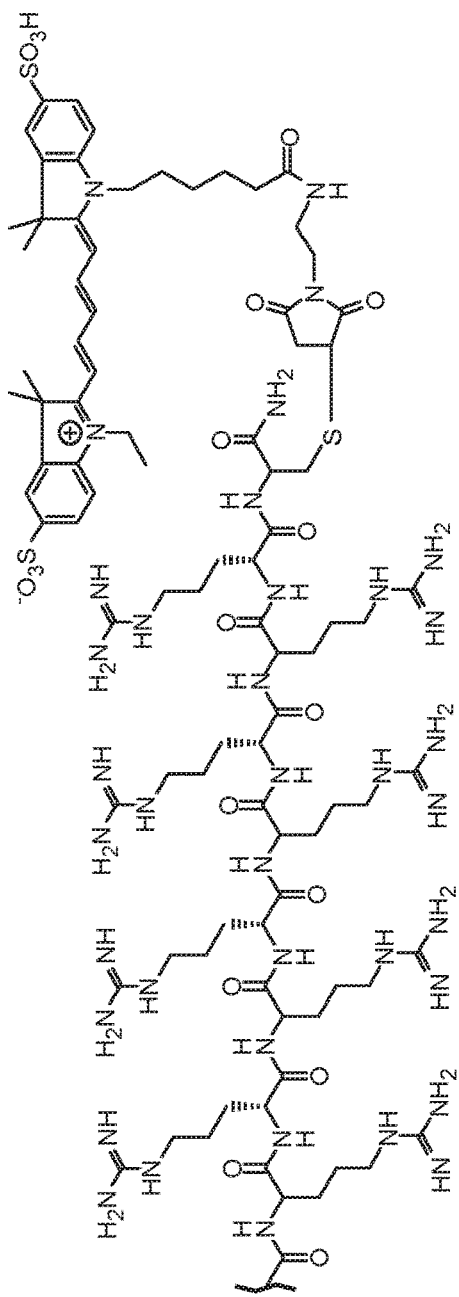

Ratiometric fluorescence detection and single intensity fluorescence detection are methodologies for use in in vitro and in vivo imaging applications. In some instances, measurements of fluorescence emission at single wavelengths are perturbed due to different tissues having different morphologies, thicknesses, cell compositions, and extracellular matrices. Ratiometric fluorescence detection utilizes a combination of fluorescent agents or indicators that generate a ratiometric change at two different wavelengths in response to a specific biological activity. In some cases, this methodology has been shown to reduce artifacts due to a variety of experimental factors including, for example, fluorophore concentration differences, subject motion, and variability in excitation light intensities and/or fluorescence emission collection and detection efficiencies for different fluorescence detectors and instruments.

Disclosed herein, in certain embodiments, are ratiometric fluorescence imaging methods for detecting and visualizing biological activity in biological specimens in vivo and ex vivo. In some cases, the ratiometric fluorescence imaging methods described herein have improved accuracy relative to an imaging method described in the arts. In some instances, the improvement in accuracy is achieved through the use of specific ratiometric fluorescence indicators, which provide greater discrimination between areas of the biological specimen that exhibit the biological activity of interest and those that don't. For example, as will be described in more detail below, in some instances the improvement in the accuracy of detecting and visualizing areas of biological activity (e.g., enhanced protease activity) is achieved through the use of ratiometric activatable cell penetrating peptides (RACPPs) that comprise a fluorescence donor and a fluorescence acceptor moiety. One non-limiting example of the latter is SDM-25 (also referred to as AVB-620), as will be described in more detail below.

In some instances, the improvement in the accuracy of detecting and visualizing areas of biological activity is achieved through the use of the image processing algorithms disclosed herein for generating and displaying fluorescence ratio images and regions-of-interest (ROI) corresponding to the areas within the biological specimen being imaged that exhibit a specific biological activity or structure of interest. In some examples, ROIs are generated from fluorescence ratio images. In some examples, ROIs are generated from a combination of fluorescence ratio images and/or fluorescence intensity images.

In some instances, the improvement in the accuracy of detecting and visualizing areas of biological activity is achieved through the use of both specific ratiometric fluorescence indicators which provide greater discrimination and the disclosed image processing algorithms for generating and displaying fluorescence ratio images and ROI.

Examples of biological activity that are detected and visualized using the disclosed ratiometric imaging techniques include, but are not limited to, changes in ion concentration (e.g., accumulation of or release of $Ca^{2+}$ ions, or changes in local pH), changes in the transmembrane potential of excitable cells, areas of enhanced protease activity, or any combination thereof. In some instances, the biological activity to be detected and visualized is correlated with various disease states, e.g., arthritis, atherosclerosis, cancer, breast cancer, pre-cancer, malignant tissue, coagulation (blood clotting), inflammation, or any combination thereof.

In some examples, the disclosed imaging and image processing methods are used to visualize ROIs in real time. In some examples, these methods are used during surgery. In some examples, these methods are used to guide surgical removal of tissue. In some examples, the tissue to be removed is cancerous tissue. In some examples, these methods are used during an endoscopic procedure. In some examples, these methods are used to guide the positioning of an endoscope or to guide surgical removal of tissue in a minimally invasive surgical procedure. In some examples, these methods are used to visualize ROIs ex vivo. As noted above, in some examples, these methods are used with activatable cell penetrating peptides (ACPPs) that comprise a fluorescence donor and fluorescence acceptor (i.e., ratiometric ACPPs). In some examples, these methods are used with SDM-25. In some examples, these methods are used in breast cancer patients or with tissue removed from these patients.

Definitions

Unless otherwise defined, all technical terms used herein have the same meaning as commonly understood by one of ordinary skill in the art in the field to which this disclosure belongs. As used in this specification and the appended claims, the singular forms "a", "an", and "the" include plural references unless the context clearly dictates otherwise. Any reference to "or" herein is intended to encompass "and/or" unless otherwise stated.

As used herein, the term "biological specimen" includes, but is not limited to, cultured cell samples, primary cell samples (e.g., tissue samples in which the extracellular matrix has been digested or dissolved to release individual cells into suspension), blood samples or fractions thereof, ex vivo tissue samples (e.g., biopsy samples or excised surgical samples), in vivo tissue samples (e.g., tumor tissue or margin tissue exposed during a surgical procedure), and the like. The biological specimens may be collected from any of a variety of organisms, e.g. prokaryotes, eukaryotes, fungi, plants, animals, or humans. In some instances, the biological specimens are patient samples.

As used herein, the term "biological activity" includes, but is not limited to, changes in ion concentration or transport activity (e.g., accumulation of or release of $Ca^{2+}$ ions, or changes in local pH), changes in the transmembrane potential of excitable cells, areas of enhanced protease activity, changes in other biochemical or physiological processes that may be monitored using ratiometric fluorescent indicators, or any combination thereof.

As used herein, the terms "ratiometric fluorescent indicator" (or "ratiometric fluorescence probe") and "ratiometric fluorescence imaging" are used broadly to include not only the use of conventional ratiometric indicators (e.g., fluorescence resonance energy transfer (FRET)-based probes) and associated imaging techniques but also, for example, instances where a combination of two or more fluorophores are used (e.g., fluorophores that are not capable of FRET pairing), with one fluorophore serving as an internal control and at least one other fluorophore serving as an indicator for the biological activity of interest. In some instances, a ratiometric fluorescent indicator is an imaging agent, e.g., for use in in vivo imaging applications.

As used herein, the term "excitation wavelength" refers to the wavelength of light used to excite a fluorescent indicator (e.g., a fluorophore or dye molecule) and generate fluorescence. Although the excitation wavelength is typically specified as a single wavelength, e.g., 620 nm, it will be understood by those of skill in the art that this specification refers to a wavelength range or excitation filter bandpass that is centered on the specified wavelength. In some instances, light of the specified excitation wavelength comprises light of the specified wavelength ±2 nm, ±5 nm, ±10 nm, ±20 nm, ±40 nm, ±80 nm, or more. In some instances, the excitation wavelength used may or may not coincide with the absorption peak maximum of the fluorescent indicator.

As used herein, the term "emission wavelength" refers to the wavelength of light emitted by a fluorescent indicator (e.g., a fluorophore or dye molecule) upon excitation by light of an appropriate wavelength. Although the emission wavelength is typically specified as a single wavelength, e.g., 670 nm, it will be understood by those of skill in the art that this specification refers to a wavelength range or emission filter bandpass that is centered on the specified wavelength. In some instances, light of the specified emission wavelength comprises light of the specified wavelength ±2 nm, ±5 nm, ±10 nm, ±20 nm, ±40 nm, ±80 nm, or more.

As used herein, the term "real time" refers to the rate at which fluorescence image data is acquired, processed, and/or displayed such that the information is used, for example, by a surgeon during a surgical procedure to guide the removal of diseased tissue. In general, the term "real time" as used herein refers to an update rate for image acquisition, processing, and/or display of at least 0.5 Hz, at least 1 Hz, at least 5 Hz, at least 10 Hz, at least 20 Hz, at least 30 Hz, at least 40 Hz, at least 50 Hz, at least 60 Hz, at least 70 Hz, at least 80 Hz, at least 90 Hz, or at least 100 Hz.

The term "surgery" as used herein, refers to any method that used to investigate, manipulate, change, or cause an effect in a tissue by a physical intervention. These methods include, but are not limited to open surgery, endoscopic surgery, laparoscopic surgery, minimally invasive surgery, robotic surgery, and any procedures that affects a cancerous tissue such as tumor resection, cancer tissue ablation, cancer staging, cancer diagnosis, lymph node staging, sentinel lymph node detection, or cancer treatment.

The term "guided surgery" as used herein, refers to any surgical procedure where the surgeon employs an imaging agent to guide the surgery.

The term "cancer" as used herein, refers to any disease involving uncontrolled growth or proliferation cells in the human body. Cancers may further be characterized by the ability of cells to migrate from the original site and spread to distant sites (i.e., metastasize). Cancers may be sarcomas, carcinomas, lymphomas, leukemias, blastomas, or germ cell tumors. Cancers may occur in a variety of tissues including but not limited to lung, breast, ovaries, colon, esophagus, rectum, bone, prostate, brain, pancreas, bladder, kidney, liver, blood cells, lymph nodes, and stomach.

The terms "polypeptide," "peptide" and "protein" are used interchangeably herein to refer to a polymer of amino acid residues. The terms apply to naturally occurring amino acid polymers as well as amino acid polymers in which one or more amino acid residues is a non-naturally occurring amino acid (e.g., an amino acid analog). The terms encompass amino acid chains of any length, including full length proteins (i.e., antigens), wherein the amino acid residues are linked by covalent peptide bonds.

Where an amino acid sequence is provided herein, L-, D-, or beta amino acid versions of the sequence are also contemplated as well as retro, inversion, and retro-inversion isoforms. Peptides also include amino acid polymers in which one or more amino acid residues is an artificial chemical analogue of a corresponding naturally occurring amino acid, as well as to naturally occurring amino acid polymers. In addition, the term applies to amino acids joined by a peptide linkage or by other modified linkages (e.g., where the peptide bond is replaced by an $\alpha$-ester, a $\beta$-ester, a thioamide, phosphonamide, carbamate, hydroxylate, and the like (see, e.g., Spatola, (1983) Chem. Biochem. Amino Acids and Proteins 7: 267-357), where the amide is replaced with a saturated amine (see, e.g., Skiles et al., U.S. Pat. No. 4,496,542, which is incorporated herein by reference, and Kaltenbronn et al., (1990) Pp. 969-970 in Proc. 11th American Peptide Symposium, ESCOM Science Publishers, The Netherlands, and the like)).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, $\gamma$-carboxyglutamate, and O-phosphoserine. Amino acids are grouped as hydrophobic amino acids, polar amino acids, non-polar amino acids, and charged amino acids. Hydrophobic amino acids include small hydrophobic amino acids and large hydrophobic amino acids. Small hydrophobic amino acid can be glycine, alanine, proline, and analogs thereof. Large hydrophobic amino acids can be valine, leucine, isoleucine, phenylalanine, methionine, tryptophan, and analogs thereof. Polar amino acids can be serine, threonine, asparagine, glutamine, cysteine, tyrosine, and analogs thereof. Non-polar amino acids can be glycine, alanine, valine, leucine, isoleucine, methionine, phenylalanine, tryptophan, proline, and analogs thereof. Charged amino acids can be lysine, arginine, histidine, aspartate, glutamate, and analogs thereof. Amino acid analogs refers to compounds that have the same basic chemical structure as a naturally occurring amino acid, i.e., an $\alpha$ carbon that is bound to a hydrogen, a carboxyl group, an amino group, and an R group, e.g., homoserine, norleucine, methionine sulfoxide. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. Amino acids are either D amino acids or L amino acids.

In some cases, such conservatively modified variants are in addition to and do not exclude polymorphic variants, interspecies homologs, and alleles of the invention.

Ratiometric Fluorescence Imaging

Ratiometric fluorescence imaging has been used extensively for a variety of measurements, including measurements of intracellular ion concentrations, cellular membrane voltages, and intracellular pH dynamics in real time. As noted above, ratiometric imaging techniques overcome some of the limitations inherent in using fluorescence intensity measurements for quantitation (e.g., variations in fluorescent indicator concentration, variations in excitation light intensity or the efficiency of collecting and detecting fluorescence emissions between different instruments, and additional challenges for in vivo imaging due to tissues having different morphologies, thicknesses, cell compositions, and extracellular matrices, etc.) by observing shifts in fluorescence emission wavelength or by comparing the emission intensity of a fluorophore combination rather than by monitoring simple changes in intensity.

In some instances, the ratiometric fluorescent indicator comprises a molecule that is excited at a single excitation wavelength, and that exhibits a shift in fluorescence emission wavelength upon sensing a specific biological activity, e.g., upon binding of an ion or cleavage by a protease. In these instances, the associated ratiometric fluorescence imaging technique comprises illuminating a biological specimen that has been infused with the indicator with light of a single excitation wavelength, and capturing fluorescence images at two different emission wavelengths (serially or simultaneously) to create a fluorescence ratio image.

In some instances, the ratiometric fluorescent indicator comprises a molecule that emits fluorescence at a single emission wavelength, and that exhibits a shift in absorption maximum upon sensing a specific biological activity, e.g., upon binding of an ion or cleavage by a protease. In these instances, the associated ratiometric fluorescence imaging technique comprises illuminating a biological specimen that has been infused with the indicator with light of two different excitation wavelengths, and serially capturing fluorescence images at the single emission wavelength to create a fluorescence ratio image.

In some instances, the "ratiometric fluorescent indicator" comprises a set of two or more fluorophores, one of which serves as an internal control (e.g. for monitoring dye concentration or a baseline biological process) and one or more of which serve as indicators of the biological activity of interest. In these instances, the associated ratiometric fluorescence imaging technique comprises illuminating a biological specimen that has been infused with the set of two or more fluorophores with light of two or more different excitation wavelengths, and serially capturing fluorescence images at two or more different emission wavelengths to create one or more fluorescence ratio images.

Ratiometric Fluorescent Indicators

A variety of ratiometric fluorescent indicators have been developed for monitoring intracellular ion concentrations, cellular membrane voltages, protease activities, and other biological processes. Examples include, but are not limited to, the calcium indicators Indo-1, Fura-2, Fura-4F, Fura-6F, Fura-FF, and Fura-Red (or Fluo-3 and Fura Red used in combination) (ThermoFisher Scientific, Waltham, Mass.); the pH indicators SNARF, Oregon Green, and BCECF (ThermoFisher Scientific, Waltham, Mass.); the membrane polarization indicators Di-4-ANEPPS, Di-8-ANEPPS, Di-2-ANEPEQ, JC-1, and JC-9 (ThermoFisher Scientific, Waltham, Mass.) (see also Gonzalez, J. E. and Tsien, R. Y.

(1997), "Improved Indicators of Cell Membrane Potential that use Fluorescence Resonance Energy Transfer", Chemistry & Biology 4:269-277); and ratiometric enzyme substrates labeled with a fluorescence donor and fluorescence acceptor, e.g., ratiometric indicators for HIV-1 protease activity (Jin, et al. (2011), "Visualization of HIV Protease Inhibition Using a Novel FRET Molecular Probe", Biotechnol Prog. 27(4): 1107-1114), matrix metalloproteinase MMP-7 and other matrix metalloproteinase activities (T. Jiang, et al. (2004), Proc. Natl. Acad. Sci. USA 101:17867-17872; Scherer, et al. (2008), Optical Imaging of Matrix Metalloproteinase-7 Activity In vivo Using a Proteolytic Nanobeacon", Mol Imaging. 7(3):118-131; Olson, et al. (2009) Integr. Biol. 1:382-393), elastase activity (Whitney, et al., (2010), J. Biol. Chem. 285:22532-22541), thrombin activity (Whitney, et al. (2013), "Ratiometric Activatable Cell-Penetrating Peptides Provide Rapid In vivo Readout of Thrombin Activation", Angew. Chem. Int. Ed. 52, 325-330), and caspase-3 activation (Mizukami, S. et al. (1999), "Imaging of Caspase-3 Activation in HeLa Cells Stimulated with Etoposide Using a Novel Fluorescent Probe", FEBS Lett. 453, 356-360).

Ratiometric Fluorescence Indicators Based on Fluorescence Resonance Energy Transfer Some ratiometric fluorescent indicators rely on a fluorescence resonance energy transfer (FRET) mechanism to impart their responsiveness to a specific biological activity of interest. Fluorogenic enzyme substrates for monitoring protease activity, for example, are one class of fluorescent indicators that frequently rely on a FRET-based mechanism, and typically comprise a short peptide sequence or linker (e.g., a peptide sequence that corresponds to all or a portion of the native substrate sequence for a particular protease) that is labeled at one end with a fluorophore (e.g., a fluorescence donor) and at the other end with a fluorescence quencher (e.g., a fluorescence acceptor). The fluorescence quencher may or may not be a fluorophore in its own right. In the intact FRET-based probe, the fluorescence donor and quencher are held in close proximity with one another, e.g., typically separated by less than about 100 Å apart. In addition to requiring that the emission spectrum of the fluorescence donor substantially overlaps with the absorption spectrum of the fluorescence quencher, the efficiency of the fluorescence resonance energy transfer process is extremely sensitive to separation distance I, and is proportional to $1/R^6$. Cleavage of the linker separating the donor and quencher by the protease suppresses the efficiency of the energy transfer process, thereby resulting in an increase in fluorescence donor emission intensity and a reduction or elimination of the fluorescence acceptor emission (in cases where the acceptor is a fluorophore, as is typical for ratiometric probes). The change in fluorescence intensity is monitored (at the emission wavelengths for both the donor and acceptor for ratiometric probes) and correlates with protease activity.

Ratiometric Activatable Cell-Penetrating Peptides (RACPPs)

Activatable cell-penetrating peptides (ACPPs; also referred to as "selective delivery molecules" (SDM)) are molecules that are capable of targeted delivery of various cargos, including fluorescent dyes or other imaging agents, to sites of protease activity in vivo (Whitney, et al. (2013), "Ratiometric Activatable Cell-Penetrating Peptides Provide Rapid In vivo Readout of Thrombin Activation", Angew. Chem. Int. Ed. 52, 325-330; Liu, et al., WO 2013/019681 A2). ACPPs consist of a polycationic cell-penetrating peptide attached to a cargo and a polyanionic inhibitory domain with a protease-cleavable linker. Probe activation and cargo uptake depend on localized proteolysis of the linker sequence that connects the polyanionic and polycationic domains, which converts the probe to an adherent form. This method provides detection of spatially localized enzymatic activity in living tissues through the accumulation of cleaved probe. ACPPs have been previously reported that target matrix metalloproteinases (MMPs) and elastases in tumors, and thrombin activation in atherosclerosis and brain injury.

Ratiometric activatable cell-penetrating peptides (RACPPs) are ACPPs that further comprise fluorescence donor and acceptor moieties to provide FRET-dependent emission ratiometric readout for monitoring protease activity in real time (Whitney, et al. (2013), "Ratiometric Activatable Cell-Penetrating Peptides Provide Rapid In vivo Readout of Thrombin Activation", Angew. Chem. Int. Ed. 52, 325-330), and provide significant advantages over single emission wavelength probes for in vivo imaging. For example, FRET from Cy5 to Cy7 within an ACPP provides a significant improvement over intensity-based ACPPs or fluorescence-dequenching probes by eliminating the need for washout to generate contrast at the site of cleavage, as well as eliminating many non-enzymatic factors that perturb intensity measurements at single wavelength emission bands. Other advantages include the large spectroscopic shift that occurs upon enzymatic cleavage of the probe, and the conversion of a diffusible substrate into an adhesive product which remains localized at the site of cleavage to confer improved spatial resolution. A hairpin structure holds the Cy5 and Cy7 (or other fluorescence donor-acceptor pairs) at a distance that ensures efficient FRET. Cleavage of the probe causes a large change (approximately 40× in the case of the Cy5/Cy7-labeled thrombin activation RACPP reported by Whitney, et al. (2013)) in emission ratio regardless of the substrate sequence or enzyme being sensed.

In some embodiments, the RACPPs (or ratiometric SDM probes) utilized in the presently disclosed imaging methods comprise molecules of Formula (I), having the structure:

$$[D_A\text{-}c_A]\text{-}A\text{-}[c_M\text{-}M]\text{-}X\text{-}B\text{-}[c_B\text{-}D_B] \qquad \text{Formula (I)}$$

wherein
X is a cleavable linker which is cleavable by a protease;
A is a peptide with a sequence comprising 5 to 20 acidic amino acid residues;
B is a peptide with a sequence comprising 5 to 20 basic amino acid residues;
$c_A$, $c_B$, and $c_M$ each independently comprise 0-1 amino acid;
M is a macromolecule; and
$D_A$ and $D_B$ are a pair of acceptor and donor fluorescent moieties that are capable of undergoing fluorescence resonance energy transfer; and wherein $[c_M\text{-}M]$ is bound to any position on A or X, $[D_A\text{-}c_A]$ is bound to any amino acid residue of A, and $[c_B\text{-}D_B]$ is bound to any amino acid residue of B.

In some embodiments, the RACPPs (or ratiometric SDM probes) utilized in the presently disclosed imaging methods comprise molecules of Formula (II), having the structure:

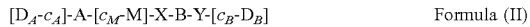
$$[D_A\text{-}c_A]\text{-}A\text{-}[c_M\text{-}M]\text{-}X\text{-}B\text{-}Y\text{-}[c_B\text{-}D_B] \qquad \text{Formula (II)}$$

wherein
X is a cleavable linker which is cleavable by a protease;
Y is a linker;
A is a peptide with a sequence comprising 5 to 20 acidic amino acid residues;
B is a peptide with a sequence comprising 5 to 20 basic amino acid residues;

$c_A$, $c_B$, and $c_M$ each independently comprise 0-1 amino acid;

M is a macromolecule; and $D_A$ and $D_B$ are a pair of acceptor and donor fluorescent moieties that are capable of undergoing fluorescence resonance energy transfer; and wherein [$c_M$-M] is bound to any position on A or X, [$D_A$-$c_A$] is bound to any amino acid residue of A, and [$c_B$-$D_B$] is bound to Y.

Portion A

In some embodiments, A is a peptide with a sequence comprising 2 to 20 acidic amino acids. In some embodiments, peptide portion A comprises between about 2 to about 20 acidic amino acids. In some embodiments, peptide portion A comprises between about 5 to about 20 acidic amino acids. In some embodiments, A has a sequence comprising 5 to 9 acidic amino acids. In some embodiments, A has a sequence comprising 5 to 8 acidic amino acids. In some embodiments, A has a sequence comprising 5 to 7 acidic amino acids. In some embodiments, A has a sequence comprising 5 acidic amino acids. In some embodiments, A has a sequence comprising 6 acidic amino acids. In some embodiments, A has a sequence comprising 7 acidic amino acids. In some embodiments, A has a sequence comprising 8 acidic amino acids. In some embodiments, A has a sequence comprising 9 acidic amino acids.

In some embodiments, peptide portion A comprises between about 2 to about 20 consecutive acidic amino acids. In some embodiments, peptide portion A comprises between about 5 to about 20 consecutive acidic amino acids. In some embodiments, A has a sequence comprising 5 to 9 consecutive acidic amino acids. In some embodiments, A has a sequence comprising 5 to 8 consecutive acidic amino acids. In some embodiments, A has a sequence comprising 5 to 7 consecutive acidic amino acids. In some embodiments, A has a sequence comprising 5 consecutive acidic amino acids. In some embodiments, A has a sequence comprising 6 consecutive acidic amino acids. In some embodiments, A has a sequence comprising 7 consecutive acidic amino acids. In some embodiments, A has a sequence comprising 8 consecutive acidic amino acids. In some embodiments, A has a sequence comprising 9 consecutive acidic amino acids.

In some embodiments, peptide portion A comprises between about 2 to about 20 acidic amino acids selected from, aspartates and glutamates. In some embodiments, peptide portion A comprises between about 5 to about 20 acidic amino acids selected from, aspartates and glutamates. In some embodiments, A has a sequence comprising 5 to 9 acidic amino acids selected from, aspartates and glutamates. In some embodiments, A has a sequence comprising 5 to 8 acidic amino acids selected from, aspartates and glutamates. In some embodiments, A has a sequence comprising 5 to 7 acidic amino acids selected from, aspartates and glutamates. In some embodiments, A has a sequence comprising 5 acidic amino acids selected from, aspartates and glutamates. In some embodiments, A has a sequence comprising 6 acidic amino acids selected from, aspartates and glutamates. In some embodiments, A has a sequence comprising 7 acidic amino acids selected from, aspartates and glutamates. In some embodiments, A has a sequence comprising 8 acidic amino acids selected from, aspartates and glutamates. In some embodiments, A has a sequence comprising 9 acidic amino acids selected from, aspartates and glutamates.

In some embodiments, peptide portion A comprises between about 2 to about 20 consecutive acidic amino acids selected from, aspartates and glutamates. In some embodiments, peptide portion A comprises between about 5 to about 20 consecutive acidic amino acids selected from, aspartates and glutamates. In some embodiments, A has a sequence comprising 5 to 9 consecutive acidic amino acids selected from, aspartates and glutamates. In some embodiments, A has a sequence comprising 5 to 8 consecutive acidic amino acids selected from, aspartates and glutamates. In some embodiments, A has a sequence comprising 5 to 7 consecutive acidic amino acids selected from, aspartates and glutamates. In some embodiments, A has a sequence comprising 5 consecutive acidic amino acids selected from, aspartates and glutamates. In some embodiments, A has a sequence comprising 6 consecutive acidic amino acids selected from, aspartates and glutamates. In some embodiments, A has a sequence comprising 7 consecutive acidic amino acids selected from, aspartates and glutamates. In some embodiments, A has a sequence comprising 8 consecutive acidic amino acids selected from, aspartates and glutamates. In some embodiments, A has a sequence comprising 9 consecutive acidic amino acids selected from, aspartates and glutamates.

In some embodiments, peptide portion A comprises between about 2 to about 20 glutamates. In some embodiments, peptide portion A comprises between about 5 to about 20 glutamates. In some embodiments, A has a sequence comprising 5 to 9 glutamates. In some embodiments, A has a sequence comprising 5 to 8 glutamates. In some embodiments, A has a sequence comprising 5 to 7 glutamates. In some embodiments, A has a sequence comprising 5 glutamates. In some embodiments, A has a sequence comprising 6 glutamates. In some embodiments, A has a sequence comprising 7 glutamates. In some embodiments, A has a sequence comprising 8 glutamates. In some embodiments, A has a sequence comprising 9 glutamates.

In some embodiments, peptide portion A comprises between about 2 to about 20 consecutive glutamates. In some embodiments, peptide portion A comprises between about 5 to about 20 consecutive glutamates. In some embodiments, A has a sequence comprising 5 to 9 consecutive glutamates. In some embodiments, A has a sequence comprising 5 to 8 consecutive glutamates. In some embodiments, A has a sequence comprising 5 to 7 consecutive glutamates. In some embodiments, A has a sequence comprising 5 consecutive glutamates. In some embodiments, A has a sequence comprising 6 consecutive glutamates. In some embodiments, A has a sequence comprising 7 consecutive glutamates. In some embodiments, A has a sequence comprising 8 consecutive glutamates. In some embodiments, A has a sequence comprising 9 consecutive glutamates.

In some embodiments, portion A comprises 5 consecutive glutamates (i.e., EEEEE or eeeee). In some embodiments, portion A comprises 9 consecutive glutamates (i.e., EEEEEEEEE or eeeeeeeee).

An acidic portion A may include amino acids that are not acidic. Acidic portion A may comprise other moieties, such as negatively charged moieties. In embodiments of a selective delivery molecule disclosed herein, an acidic portion A is a negatively charged portion, preferably having about 2 to about 20 negative charges at physiological pH that does not include an amino acid.

In some embodiments, the amount of negative charge in portion A is approximately the same as the amount of positive charge in portion B. In some embodiments, the amount of negative charge in portion A is not the same as the amount of positive charge in portion B. In some embodiments, improved tissue uptake is seen in a selective delivery molecule wherein the amount of negative charge in portion A is not the same as the amount of positive charge in portion B. In some embodiments, improved solubility is observed in a selective delivery molecule wherein the amount of negative charge in portion A is not the same as the amount of positive charge in portion B. In some embodiments, faster tissue uptake is seen in a selective delivery molecule wherein the amount of negative charge in portion A is not the same as the amount of positive charge in portion B. In some embodiments, greater tissue uptake is seen in a selective delivery molecule wherein the amount of negative charge in portion A is not the same as the amount of positive charge in portion B.

Portion A is either L-amino acids or D-amino acids. In embodiments of the invention, D-amino acids are preferred in order to minimize immunogenicity and nonspecific cleavage by background peptidases or proteases.

It will be understood that portion A may include non-standard amino acids, such as, for example, hydroxylysine, desmosine, isodesmosine, or other non-standard amino acids. Portion A may include modified amino acids, including post-translationally modified amino acids such as, for example, methylated amino acids (e.g., methyl histidine, methylated forms of lysine, etc.), acetylated Amino acids, amidated amino acids, formylated amino acids, hydroxylated amino acids, phosphorylated amino acids, or other modified amino acids. Portion A may also include peptide mimetic moieties, including portions linked by non-peptide bonds and amino acids linked by or to non-amino acid portions.

The selective delivery molecules disclosed herein are effective where A is at the amino terminus or where A is at the carboxy terminus, i.e., either orientation of the peptide bonds is permissible.

Portion B

In some embodiments, B is a peptide with a sequence comprising 5 to 15 basic amino acids. In some embodiments, peptide portion B comprises between about 5 to about 20 basic amino acids. In some embodiments, peptide portion B comprises between about 5 to about 12 basic amino acids. In some embodiments, peptide portion B comprises between about 7 to about 9 basic amino acids. In some embodiments, peptide portion B comprises between about 7 to about 8 basic amino acids. In some embodiments, peptide portion B comprises 9 basic amino acids. In some embodiments, peptide portion B comprises 8 basic amino acids. In some embodiments, peptide portion B comprises 7 basic amino acids.

In some embodiments, peptide portion B comprises between about 5 to about 20 consecutive basic amino acids. In some embodiments, peptide portion B comprises between about 5 to about 12 consecutive basic amino acids. In some embodiments, peptide portion B comprises between about 7 to about 9 consecutive basic amino acids. In some embodiments, peptide portion B comprises between about 7 to about 8 consecutive basic amino acids. In some embodiments, peptide portion B comprises 9 consecutive basic amino acids. In some embodiments, peptide portion B comprises 8 consecutive basic amino acids. In some embodiments, peptide portion B comprises 7 consecutive basic amino acids.

In some embodiments, peptide portion B comprises between about 5 to about 20 basic amino acids selected from arginines, histidines, and lysines. In some embodiments, peptide portion B comprises between about 5 to about 12 basic amino acids selected from arginines, histidines, and lysines. In some embodiments, peptide portion B comprises between about 7 to about 9 basic amino acids selected from arginines, histidines, and lysines. In some embodiments, peptide portion B comprises between about 7 to about 8 basic amino acids selected from arginines, histidines, and lysines. In some embodiments, peptide portion B comprises 9 basic amino acids selected from arginines, histidines, and lysines. In some embodiments, peptide portion B comprises 8 basic amino acids selected from arginines, histidines, and lysines. In some embodiments, peptide portion B comprises 7 basic amino acids selected from arginines, histidines, and lysines.

In some embodiments, peptide portion B comprises between about 5 to about 20 consecutive basic amino acids selected from arginines, histidines, and lysines. In some embodiments, peptide portion B comprises between about 5 to about 12 consecutive basic amino acids selected from arginines, histidines, and lysines. In some embodiments, peptide portion B comprises between about 7 to about 9 consecutive basic amino acids selected from arginines, histidines, and lysines. In some embodiments, peptide portion B comprises between about 7 to about 8 consecutive basic amino acids selected from arginines, histidines, and lysines. In some embodiments, peptide portion B comprises 9 consecutive basic amino acids selected from arginines, histidines, and lysines. In some embodiments, peptide portion B comprises 8 consecutive basic amino acids selected from arginines, histidines, and lysines.

In some embodiments, peptide portion B comprises between about 5 to about 20 arginines. In some embodiments, peptide portion B comprises between about 5 to about 12 arginines. In some embodiments, peptide portion B comprises between about 7 to about 9 arginines. In some embodiments, peptide portion B comprises between about 7 to about 8 arginines. In some embodiments, peptide portion B comprises 9 arginines. In some embodiments, peptide portion B comprises 8 arginines. In some embodiments, peptide portion B comprises 7 arginines.

In some embodiments, peptide portion B comprises between about 5 to about 20 consecutive arginines. In some embodiments, peptide portion B comprises between about 5 to about 12 consecutive arginines. In some embodiments, peptide portion B comprises between about 7 to about 9 consecutive arginines. In some embodiments, peptide portion B comprises between about 7 to about 8 consecutive arginines. In some embodiments, peptide portion B comprises 9 consecutive arginines. In some embodiments, peptide portion B comprises 8 consecutive arginines. In some embodiments, peptide portion B comprises 7 consecutive arginines.

A basic portion B may include amino acids that are not basic. Basic portion B may comprise other moieties, such as positively charged moieties. In embodiments, a basic portion B is a positively charged portion, preferably having between about 5 and about 20 positive charges at physiological pH, that does not include an amino acid. In some embodiments, the amount of negative charge in portion A is approximately the same as the amount of positive charge in portion B. In some embodiments, the amount of negative charge in portion A is not the same as the amount of positive charge in portion B.

Portion B is either L-amino acids or D-amino acids. In embodiments of the invention, D-amino acids are preferred in order to minimize immunogenicity and nonspecific cleavage by background peptidases or proteases. Cellular uptake of oligo-D-arginine sequences is known to be as good as or better than that of oligo-L-arginines.

It will be understood that portion B may include non-standard amino acids, such as, for example, hydroxylysine, desmosine, isodesmosine, or other non-standard amino acids. Portion B may include modified amino acids, including post-translationally modified amino acids such as, for example, methylated amino acids (e.g., methyl histidine, methylated forms of lysine, etc.), acetylated amino acids, amidated amino acids, formylated amino acids, hydroxylated amino acids, phosphorylated amino acids, or other modified amino acids. Portion B may also include peptide mimetic moieties, including portions linked by non-peptide bonds and amino acids linked by or to non-amino acid portions.

In embodiments where X is a peptide cleavable by a protease, it is preferable to join the C-terminus of X to the N-terminus of B, so that the new amino terminus created by cleavage of X contributes an additional positive charge that adds to the positive charges already present in B.

Conjugation Group (c)

In some embodiments, the cargo (e.g., $D_A$ and $D_B$) and the macromolecule carriers (M) are attached indirectly to A-X-B.

In some embodiments, the cargo (e.g., $D_A$ and $D_B$) and the macromolecule carriers (M) are attached indirectly to A-X-B by a conjugation group ($c_A$, $c_B$, and $c_M$). In some embodiments, the cargo (e.g., $D_A$ and $D_B$) and the macromolecule carriers (M) are attached indirectly to A-X-B by a reactive conjugation group ($c_A$, $c_B$, and $c_M$). In some embodiments, the cargo (e.g., $D_A$ and $D_B$) and the macromolecule carriers (M) are attached indirectly to A-X-B by an orthogonally-reactive conjugation group ($c_A$, $c_B$, and $c_M$). In some embodiments, $c_A$, $c_B$, and $c_M$ each independently comprise an amino acid. In some embodiments, $c_A$, $c_B$, and $c_M$ each independently comprise 0-10 amino acids. In some embodiments, $c_A$, $c_B$, and $c_M$ each independently comprise 1 amino acid. In some embodiments, $c_A$, $c_B$, and $c_M$ each independently comprise 2 amino acids. In some embodiments, $c_A$, $c_B$, and $c_M$ each independently comprise 3 amino acids. In some embodiments, $c_A$, $c_B$, and $c_M$ each independently comprise 4 amino acids. In some embodiments, $c_A$, $c_B$, and $c_M$ each independently comprise 5 amino acids. In some embodiments, $c_A$, $c_B$, and $c_M$ each independently comprise 6 amino acids. In some embodiments, $c_A$, $c_B$, and $c_M$ each independently comprise 7 amino acids. In some embodiments, $c_A$, $c_B$, and $c_M$ each independently comprise 8 amino acids. In some embodiments, $c_A$, $c_B$, and $c_M$ each independently comprise 9 amino acids. In some embodiments, $c_A$, $c_B$, and $c_M$ each independently comprise 10 amino acids.

In some embodiments, $c_A$, $c_B$, and $c_M$ each independently comprise a derivatized amino acid. In some embodiments, multiple cargos (D) are attached to a derivatized amino acid conjugation group.

In some embodiments, the conjugation group comprises a receptor ligand.

In some embodiments, $c_A$, $c_B$, and $c_M$ each independently comprise a naturally-occurring amino acid or a non-naturally-occurring amino acid. In some embodiments, $c_A$, $c_B$, and $c_M$ each independently comprise from a D amino acid, a L amino acid, an α-amino acid, a ß-amino acid, or a γ-amino acid. In some embodiments, $c_A$, $c_B$, and $c_M$ each independently comprise any amino acid having a free thiol group, any amino acid containing a free amine group, any amino acid having a N-terminal amine group, and any amino acid with a side chain capable of forming an oxime or hydrazone bond upon reaction with a hydroxylamine or hydrazine group. In some embodiments, $c_A$, $c_B$, and $c_M$ each independently comprise D-cysteine, D-glutamate, lysine, and para-4-acetyl L-phenylalanine. In some embodiments, $c_B$ comprises any amino acid having a free thiol group. In some embodiments, $c_B$ comprises D-cysteine. In some embodiments, $c_A$ comprises any amino acid having a N-terminal amine group. In some embodiments, $c_A$ comprises D-glutamate. In some embodiments, $c_A$ comprises lysine. In some embodiments, $c_M$ comprises any amino acid with a side chain capable of forming an oxime or hydrazone bond upon reaction with a hydroxylamine or hydrazine group. In some embodiments, $c_M$ comprises para-4-acetyl L-phenylalanine.

In some embodiments, $c_A$, $c_B$, and $c_M$ are each independently selected from a naturally-occurring amino acid or a non-naturally-occurring amino acid. In some embodiments, $c_A$, $c_B$, and $c_M$ are each independently selected from a D amino acid, a L amino acid, an α-amino acid, a ß-amino acid, or a γ-amino acid. In some embodiments, $c_A$, $c_B$, and $c_M$ are each independently any amino acid having a free thiol group, any amino acid containing a free amine group, any amino acid having a N-terminal amine group, and any amino acid with a side chain capable of forming an oxime or hydrazone bond upon reaction with a hydroxylamine or hydrazine group. In some embodiments, $c_A$, $c_B$, and $c_M$ are each independently selected from: D-cysteine, D-glutamate, lysine, and para-4-acetyl L-phenylalanine. In some embodiments, $c_B$ is any amino acid having a free thiol group. In some embodiments, $c_B$ is D-cysteine. In some embodiments, $c_A$ is any amino acid having a N-terminal amine group. In some embodiments, $c_A$ is D-glutamate. In some embodiments, $c_A$ is lysine. In some embodiments, $c_M$ is any amino acid with a side chain capable of forming an oxime or hydrazone bond upon reaction with a hydroxylamine or hydrazine group. In some embodiments, $c_M$ is para-4-acetyl L-phenylalanine.

Imaging Agents (Cargo)

In some embodiments, the cargo portion (D) of the selective delivery molecule comprises an imaging agent, for example, a fluorophore or dye. In some embodiments, an imaging agent is a fluorescent moiety. In some embodiments, a fluorescent moiety is selected from: a fluorescent protein, a fluorescent peptide, a fluorescent dye, a fluorescent material or a combination thereof. In some embodiments, an imaging agent comprises a combination of fluorescence moieties (e.g. $D_A$ and $D_B$) attached to the same selective delivery molecule.

All fluorescent moieties are encompassed within the term "fluorescent moiety." Specific examples of fluorescent moieties given herein are illustrative and are not meant to limit the fluorescent moieties for use with the targeting molecules disclosed herein.

Examples of fluorescent dyes include, but are not limited to, xanthenes (e.g., rhodamines, rhodols and fluoresceins, and their derivatives); bimanes; coumarins and their derivatives (e.g., umbelliferone and aminomethyl coumarins); aromatic amines (e.g., dansyl; squarate dyes); benzofurans; fluorescent cyanines; indocarbocyanines; carbazoles; dicyanomethylene pyranes; polymethine; oxabenzanthrane; xanthene; pyrylium; carbostyl; perylene; acridone; quinacridone; rubrene; anthracene; coronene; phenanthrecene; pyrene; butadiene; stilbene; porphyrin; pthalocyanine; lanthanide metal chelate complexes; rare-earth metal chelate complexes; and derivatives of such dyes.

Examples of fluorescein dyes include, but are not limited to, 5-carboxyfluorescein, fluorescein-5-isothiocyanate, fluorescein-6-isothiocyanate and 6-carboxyfluorescein.

Examples of rhodamine dyes include, but are not limited to, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride (sold under the tradename of TEXAS RED®).

Examples of cyanine dyes include, but are not limited to, Cy3, Cy3B, Cy3.5, Cy5, Cy5.5, Cy7, IR Dye680, Alexa Fluor 750, IR Dye800CW, ICG.

Examples of fluorescent peptides include GFP (Green Fluorescent Protein) or derivatives of GFP (e.g., EBFP, EBFP2, Azurite, mKalamal, ECFP, Cerulean, CyPet, YFP, Citrine, Venus, Ypet).

In some embodiments, the imaging agent is a near-infrared fluorophore for near-infra red (near-IR) imaging, a luciferase (firefly, bacterial, or coelenterate) or other luminescent molecule for bioluminescence imaging, or a perfluorocarbon-filled vesicle for ultrasound.

In preferred embodiments, the RACCPs or ratiometric SDMs of the present disclosure are labeled with a fluorescence donor—acceptor pair. Examples of suitable fluorescence donor-acceptor pairs include, but are not limited to, fluorescein/rhodamine, fluorescein/Cy5, rhodamine/Cy5, Cy5/Cy7, Cy5/IR Dye750, Cy5/IR Dye800, Cy5/ICG, and the liked. Cy5 and Cy7 provide one example of a preferred fluorescence donor—acceptor pair, as the long wavelengths of Cy5 and Cy7 are ideal for in vivo imaging, where excitation and emission wavelengths should be well above 600 nm to avoid the strong absorbance of endogenous hemes. For the Cy5/Cy 7 donor-acceptor pair, for example, excitation with light in the wavelength range of about 610 nm to 630 nm (for Cy5 excitation), and collection of fluorescence emission at about 660 nm to 720 nm (for Cy5 emission), and about 760 nm to 830 nm (for Cy 7 emission) allows accurate ratiometric measurements to be made while avoiding interference by endogenous hemes.

Macromolecular Carriers (M)

The term "carrier" means an inert molecule that modulates plasma half-life, solubility, or bio-distribution. In some embodiments, a carrier modulates plasma half-life of a selective delivery molecule disclosed herein. In some embodiments, a carrier modulates solubility of a selective delivery molecule disclosed herein. In some embodiments, a carrier modulates bio-distribution of a selective delivery molecule disclosed herein.

In some embodiments, a carrier decreases uptake of a selective delivery molecule by non-target cells or tissues. In some embodiments, a carrier decreases uptake of a selective delivery molecule into cartilage. In some embodiments, a carrier decreases uptake of a selective delivery molecule into joints relative to target tissue.

In some embodiments, a carrier increases uptake of a selective delivery molecule by target cells or tissues. In some embodiments, a carrier decreases uptake of a selective delivery molecule into the liver relative to target tissue. In some embodiments, a carrier decreases uptake of a selective delivery molecule into kidneys. In some embodiments, a carrier enhances uptake into cancer tissue. In some embodiments, a carrier enhances uptake into lymphatic channels and/or lymph nodes.

In some embodiments, a carrier increases plasma half-life by reducing glomerular filtration. In some embodiments, a carrier modulates plasma half-life by increasing or decreases metabolism or protease degradation. In some embodiments, a carrier increases tumor uptake due to enhanced permeability and retention (EPR) of tumor vasculature. In some embodiments, a carrier increases the aqueous solubility of selective delivery molecule.

In some embodiments, any M is independently directly or indirectly (e.g., via $c_M$) bound to A, B, or X. In some embodiments, any M is independently bound to A at the n-terminal poly glutamate. In some embodiments, any M is independently bound to A (or, the n-terminal poly glutamate) by a covalent linkage. In some embodiments, any M is independently bound to B at the c-terminal polyarginine. In some embodiments, any M is independently bound to B (or, the c-terminal polyarginine) by a covalent linkage. In some embodiments, any M is independently directly or indirectly bound to linkers between X and A, X and B, B and the C/N terminus, or the A and the C/N terminus. In some embodiments, the covalent linkage comprises an ether bond, thio-ether bond, amine bond, amide bond, oxime bond, carbon-carbon bond, carbon-nitrogen bond, carbon-oxygen bond, or carbon-sulfur bond.

In some embodiments, M is selected from a protein, a synthetic or natural polymer, or a dendrimer. In some embodiments, M is selected from dextran, a PEG polymer (e.g., PEG 5 kDa, PEG 12 kDa, PEG 20 kDa, PEG 30 kDa, and PEG40 kDa), albumin, or a combination thereof.

In some embodiments, M is a PEG polymer. In some instances, PEG is a polydispered or monodispered compound. In some instances, polydispered material comprises disperse distribution of different molecular weight of the material, characterized by mean weight (weight average) size and dispersity. In other instances, PEG is a monodisperse compound, which comprises one size of the molecule.

In some embodiments, the molecular weight of PEG is about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50,000, 60,000, or 100,000 Da.

In some instances, M has a molecule weight of about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50,000, 60,000, or 100,000 Da. In some instances, the molecular weight of M is about 200 Da. In some instances, the molecular weight of M is about 300 Da. In some instances, the molecular weight of M is about 400 Da. In some instances, the molecular weight of M is about 500 Da. In some instances, the molecular weight of M is about 600 Da. In some instances, the molecular weight of M is about 700 Da. In some instances, the molecular weight of M is about 800 Da. In some instances, the molecular weight of M is about 900 Da. In some instances, the molecular weight of M is about 1000 Da. In some instances, the molecular weight of M is about 1100 Da. In some instances, the molecular weight of M is about 1200 Da. In some instances, the molecular weight of M is about 1300 Da. In some instances, the molecular weight of M is about 1400 Da. In some instances, the molecular weight of M is about 1450 Da. In some instances, the molecular weight of M is about 1500 Da. In some instances, the molecular weight of M is about 1600 Da. In some instances, the molecular weight of M is about 1700 Da. In some instances, the molecular weight of M is about 1800 Da. In some instances, the molecular weight of M is about 1900 Da. In some instances, the molecular weight of M is about 2000 Da. In some instances, the molecular weight of M is about 2100 Da. In some instances, the molecular weight of M is about 2200 Da. In some instances, the molecular weight of M is about 2300 Da. In some instances, the molecular weight of M is about 2400 Da. In some instances, the molecular weight of M is about 2500 Da. In some instances, the molecular weight of M is about 2600 Da. In some instances, the molecular weight of M is about 2700 Da. In some instances, the molecular weight of M is about 2800 Da. In some instances, the molecular weight of M is about 2900 Da. In some instances, the molecular weight of M is about 3000 Da. In some instances, the molecular weight of M is about 3250 Da. In some instances, the molecular weight of M is about 3350 Da. In some instances, the molecular weight of M is about 3500 Da. In some instances, the molecular weight of M is about 3750 Da. In some instances, the molecular weight of M is about 4000 Da. In some instances, the molecular weight of M is about 4250 Da. In some instances, the molecular weight of M is about 4500 Da. In some instances, the molecular weight of M is about 4600 Da. In some instances, the molecular weight of M is about 4750 Da. In some instances, the molecular weight of M is about 5000 Da. In some instances, the molecular weight of M is about 5500 Da. In some instances, the molecular weight of M is about 6000 Da. In some instances, the molecular weight of M is about 6500 Da. In some instances, the molecular weight of M is about 7000 Da. In some instances, the molecular weight of M is about 7500 Da. In some instances, the molecular weight of M is about 8000 Da. In some instances, the molecular weight of M is about 10,000 Da. In some instances, the molecular weight of M is about 12,000 Da. In some instances, the molecular weight of M is about 20,000 Da. In some instances, the molecular weight of M is about 35,000 Da. In some instances, the molecular weight of M is about 40,000 Da. In some instances, the molecular weight of M is about 50,000 Da. In some instances, the molecular weight of M is about 60,000 Da. In some instances, the molecular weight of M is about 100,000 Da.

In some embodiments, an average molecular weight of M is between 50 and 70 kD.

In some embodiments, M is a discrete PEG, in which the discrete PEG is a polymeric PEG comprising more than one repeating ethylene oxide units. In some instances, a discrete PEG (dPEG) comprises from 2 to 60, from 2 to 50, or from 2 to 48 repeating ethylene oxide units. In some instances, a dPEG comprises about 2, 3, 4, 5, 6, 7, 8, 9, 10, 11, 12, 13, 14, 15, 16, 17, 18, 19, 20, 22, 24, 26, 28, 30, 35, 40, 42, 48, 50 or more repeating ethylene oxide units. In some instances, a dPEG comprises about 2 or more repeating ethylene oxide units. In some instances, a dPEG comprises about 3 or more repeating ethylene oxide units. In some instances, a dPEG comprises about 4 or more repeating ethylene oxide units. In some instances, a dPEG comprises about 5 or more repeating ethylene oxide units. In some instances, a dPEG comprises about 6 or more repeating ethylene oxide units. In some instances, a dPEG comprises about 7 or more repeating ethylene oxide units. In some instances, a dPEG comprises about 8 or more repeating ethylene oxide units. In some instances, a dPEG comprises about 9 or more repeating ethylene oxide units. In some instances, a dPEG comprises about 10 or more repeating ethylene oxide units. In some instances, a dPEG comprises about 11 or more repeating ethylene oxide units. In some instances, a dPEG comprises about 12 or more repeating ethylene oxide units. In some instances, a dPEG comprises about 13 or more repeating ethylene oxide units. In some instances, a dPEG comprises about 14 or more repeating ethylene oxide units. In some instances, a dPEG comprises about 15 or more repeating ethylene oxide units. In some instances, a dPEG comprises about 16 or more repeating ethylene oxide units. In some instances, a dPEG comprises about 17 or more repeating ethylene oxide units. In some instances, a dPEG comprises about 18 or more repeating ethylene oxide units. In some instances, a dPEG comprises about 19 or more repeating ethylene oxide units. In some instances, a dPEG comprises about 20 or more repeating ethylene oxide units. In some instances, a dPEG comprises about 22 or more repeating ethylene oxide units. In some instances, a dPEG comprises about 24 or more repeating ethylene oxide units. In some instances, a dPEG comprises about 26 or more repeating ethylene oxide units. In some instances, a dPEG comprises about 28 or more repeating ethylene oxide units. In some instances, a dPEG comprises about 30 or more repeating ethylene oxide units. In some instances, a dPEG comprises about 35 or more repeating ethylene oxide units. In some instances, a dPEG comprises about 40 or more repeating ethylene oxide units. In some instances, a dPEG comprises about 42 or more repeating ethylene oxide units. In some instances, a dPEG comprises about 48 or more repeating ethylene oxide units. In some instances, a dPEG comprises about 50 or more repeating ethylene oxide units. In some cases, a dPEG is synthesized as a single molecular weight compound from pure (e.g., about 95%, 98%, 99%, or 99.5%) staring material in a step-wise fashion. In some cases, a dPEG has a specific molecular weight, rather than an average molecular weight. In some cases, a dPEG described herein is a dPEG from Quanta Biodesign, LIVID.

In some embodiments, the selective delivery molecule is conjugated to albumin. In certain instances, albumin is excluded from the glomerular filtrate under normal physiological conditions. In some embodiments, the selective delivery molecule comprises a reactive group such as maleimide that can form a covalent conjugate with albumin. A selective delivery molecule comprising albumin results in enhanced accumulation of cleaved selective delivery molecules in tumors in a cleavage dependent manner. In some embodiments, albumin conjugates have good pharmacokinetic properties.

In some embodiments, the selective delivery molecule is conjugated to a PEG polymer. In some embodiments, the selective delivery molecule is conjugated to a PEG 500 Da polymer. In some embodiments, the selective delivery molecule is conjugated to a PEG 1 kDa polymer. In some embodiments, the selective delivery molecule is conjugated to a PEG 2 kDa polymer. In some embodiments, the selective delivery molecule is conjugated to a PEG 5 kDa polymer. In some embodiments, the selective delivery molecule is conjugated to a PEG 10 kDa polymer. In some embodiments, the selective delivery molecule is conjugated to a PEG 12 kDa polymer. In some embodiments, selective delivery molecule is conjugated to a PEG 20 kDa polymer. In some embodiments, 30 kD PEG conjugates had a longer half-life as compared to free peptides. In some embodiments, selective delivery molecules are conjugated to 20-40 kD PEG polymer which has hepatic and renal clearance.

In some embodiments, the selective delivery molecule is conjugated to a dextran. In some embodiments, the selective delivery molecule is conjugated to a 70 kDa dextran. In some embodiments, dextran conjugates, being a mixture of molecular weights, are difficult to synthesize and purify reproducibly.

In some embodiments, the selective delivery molecule is conjugated to streptavidin.

In some embodiments, the selective delivery molecule is conjugated to a fifth generation PAMAM dendrimer.

In some embodiments, a carrier is capped. In some embodiments, capping a carrier improves the pharmacokinetics and reduces cytotoxicity of a carrier by adding hydrophilicity. In some embodiments, the cap is selected from: Acetyl, succinyl, 3-hydroxypropionyl, 2-sulfobenzoyl, glycidyl, PEG-2, PEG-4, PEG-8 and PEG-12.

Portion X (Linkers)

In some embodiments, a linker consisting of one or more amino acids is used to join peptide sequence A (i.e., the sequence designed to inhibit the delivery action of peptide B) and peptide sequence B. Generally, the peptide linker will have no specific biological activity other than to join the molecules or to preserve some minimum distance or other spatial relationship between them. However, the constituent amino acids of the linker may be selected to influence some property of the molecule such as the folding, net charge, or hydrophobicity.

In live cells, an intact selective delivery molecule disclosed herein may not be able to enter the cell because of the presence of portion A. Thus, a strictly intracellular process for cleaving X would be ineffective to cleave X in healthy cells since portion A, preventing uptake into cells, would not be effectively cleaved by intracellular enzymes in healthy cells since it would not be taken up and would not gain access to such intracellular enzymes. However, where a cell is injured or diseased (e.g., cancerous cells, hypoxic cells, ischemic cells, apoptotic cells, necrotic cells) such intracellular enzymes leak out of the cell and cleavage of A would occur, allowing entry of portion B and/or cargo into the cell, effecting targeted delivery of portion B and/or cargo D to neighboring cells. In some embodiments, X is cleaved in the extracellular space.

In some embodiments, the fact that capillaries are often leaky around tumors and other trauma sites enhances the ability of high molecular weight molecules (e.g., molecular weight of about 30 kDa or more) to reach the interstitial compartment. In some embodiments, cells that do not express the relevant protease but that are immediately adjacent to expressing cells pick up cargo from a selective delivery molecule because cleavage of the X linker is typically extracellular. In some embodiments, such bystander targeting is beneficial in the treatment of tumors because of the heterogeneity of cell phenotypes and the wish to eliminate as high a percentage of suspicious cells as possible.

In some embodiments, X is a cleavable linker. In some embodiments, X is a linker that is cleavable by a protease. In some embodiments, X is a linker that is cleavable by an extracellular protease.

In some embodiments, the linker is flexible. In some embodiments, the linker is rigid.

In some embodiments, the linker comprises a linear structure. In some embodiments, the linker comprises a non-linear structure. In some embodiments, the linker comprises a branched structure. In some embodiments, the linker comprises a cyclic structure.

Linkers include, but are not limited to, straight or branched chain carbon linkers, heterocyclic carbon linkers, peptide linkers, and polyether linkers. These linkers optionally have amide linkages, sulfhydryl linkages, or heterofunctional linkages.

In some embodiments, X is about 5 to about 30 atoms in length. In some embodiments, X is about 6 atoms in length. In some embodiments, X is about 8 atoms in length. In some embodiments, X is about 10 atoms in length. In some embodiments, X is about 12 atoms in length. In some embodiments, X is about 14 atoms in length. In some embodiments, X is about 16 atoms in length. In some embodiments, X is about 18 atoms in length. In some embodiments, X is about 20 atoms in length. In some embodiments, X is about 25 atoms in length. In some embodiments, X is about 30 atoms in length.

In some embodiments, the linker binds peptide portion A (i.e., the peptide sequence which prevents cellular uptake) to peptide portion B (i.e., the delivery sequence) by a covalent linkage. In some embodiments, the covalent linkage comprises an ether bond, thioether bond, amine bond, amide bond, oxime bond, hydrazone bond, carbon-carbon bond, carbon-nitrogen bond, carbon-oxygen bond, or carbon-sulfur bond.

In some embodiments, X comprises a peptide linkage. The peptide linkage comprises L-amino acids and/or D-amino acids. In embodiments of the invention, D-amino acids are preferred in order to minimize immunogenicity and nonspecific cleavage by background peptidases or proteases. Cellular uptake of oligo-D-arginine sequences is known to be as good as or better than that of oligo-L-arginines.

In some embodiments, an X linker is designed for cleavage in the presence of particular conditions or in a particular environment. In preferred embodiments, an X linker is cleavable under physiological conditions. Cleavage of such an X linker may, for example, be enhanced or may be affected by particular pathological signals or a particular environment related to cells in which cargo delivery is desired. The design of an X linker for cleavage by specific conditions, such as by a specific enzyme, allows the targeting of cellular uptake to a specific location where such conditions obtain. Thus, one important way that selective delivery molecules provide specific targeting of cellular uptake to desired cells, tissues, or regions is by the design of the linker portion X to be cleaved by conditions near such targeted cells, tissues, or regions.

In some embodiments, X is a pH-sensitive linker. In some embodiments, X is cleaved under basic pH conditions. In some embodiments, X is cleaved under acidic pH conditions. In some embodiments, X is cleaved by a protease, a matrix metalloproteinase, or a combination thereof. In some embodiments, X is cleaved by a reducing agent.

In some embodiments, X is cleaved by an MMP. The hydrolytic activity of matrix metalloproteinases (MMPs) has been implicated in the invasive migration of metastatic tumor cells. In certain instances, MMPs are found near sites of inflammation. In certain instances, MMPs are found near sites of stroke (i.e., a disorder characterized by brain damage following a decrease in blood flow). Thus, uptake of molecules having features of the invention are able to direct cellular uptake of cargo (at least one D moiety) to specific cells, tissues, or regions having active MMPs in the extracellular environment. In some embodiments, a X linker that includes the amino-acid sequences PLG-C(Me)-AG (SEQ ID NO: 1), PLGLAG (SEQ ID NO: 2) which are cleaved by the metalloproteinase enzymes MMP-2, MMP-9, or MMP-7 (MMPs involved in cancer and inflammation).

In some embodiments, X is cleaved by proteolytic enzymes or reducing environment, as is found near cancerous cells. Such an environment, or such enzymes, are typically not found near normal cells.

In some embodiments, X is cleaved by serine proteases including but not limited to thrombin and cathepsins. In some embodiments, X is cleaved by cathepsin K, cathepsin S, cathepsin D, cathepsin E, cathepsin W, cathepsin F, cathepsin A, cathepsin C, cathepsin H, cathepsin Z, or any combinations thereof. In some embodiments, X is cleaved by cathepsin K and/or cathepsin S.

In some embodiments, X is cleaved in or near tissues suffering from hypoxia. In some embodiments, cleavage in or near hypoxic tissues enables targeting of cancer cells and cancerous tissues, infarct regions, and other hypoxic regions. In some embodiments, X comprises a disulfide bond. In some embodiments, a linker comprising a disulfide bond is preferentially cleaved in hypoxic regions and so targets cargo delivery to cells in such a region. Hypoxia is thought to cause cancer cells to become more resistant to radiation and chemotherapy, and also to initiate angiogenesis. In a hypoxic environment in the presence of, for example, leaky or necrotic cells, free thiols and other reducing agents become available extracellularly, while the $O_2$ that normally keeps the extracellular environment oxidizing is by definition depleted. In some embodiments, this shift in the redox balance promotes reduction and cleavage of a disulfide bond within a X linker. In addition to disulfide linkages which take advantage of thiol-disulfide equilibria, linkages including quinones that fall apart when reduced to hydroquinones are used in a X linker designed to be cleaved in a hypoxic environment.

In some embodiments, X is cleaved in a necrotic environment. Necrosis often leads to the release of enzymes or other cell contents that may be used to trigger cleavage of a X linker. In some embodiments, cleavage of X by necrotic enzymes (e.g., by calpains) allows cargo to be taken up by diseased cells and by neighboring cells that had not yet become fully leaky.

In some embodiments, X is an acid-labile linker. In some embodiments, X comprises an acetal or vinyl ether linkage. Acidosis is observed in sites of damaged or hypoxic tissue, due to the Warburg shift from oxidative phosphorylation to anaerobic glycolysis and lactic acid production. In some embodiments, acidosis is used as a trigger of cargo uptake by replacing some of the arginines within B by histidines, which only become cationic below pH 7.

It will be understood that a linker disclosed herein may include non-standard amino acids, such as, for example, hydroxylysine, desmosine, isodesmosine, or other non-standard amino acids. A linker disclosed herein may include modified amino acids, including post-translationally modified amino acids such as, for example, methylated amino acids (e.g., methyl histidine, methylated forms of lysine, etc.), acetylated amino acids, amidated amino acids, formylated amino acids, hydroxylated amino acids, phosphorylated amino acids, or other modified amino acids. A linker disclosed herein may also include peptide mimetic moieties, including portions linked by non-peptide bonds and amino acids linked by or to non-amino acid portions.

In some embodiments, the linker X comprises an amino acid sequence selected from: PLGLAG, PLG-C(me)-AG, RPLALWRS, ESPAYYTA, DPRSFL, PPRSFL, RLQLKL, and RLQLK(Ac). In some embodiments, the linker X comprises the amino acid sequence PLGLAG. In some embodiments, the linker X comprises the amino acid sequence PLG-C(me)-AG. In some embodiments, the linker X comprises the amino acid sequence PLGxAG, wherein x is any amino acid (naturally-occurring or non-naturally occurring). In some embodiments, the linker X comprises the amino acid sequence RPLALWRS. In some embodiments, the linker X comprises the amino acid sequence ESPAYYTA. In some embodiments, the linker X comprises the amino acid sequence DPRSFL. In some embodiments, the linker X comprises the amino acid sequence PPRSFL. In some embodiments, the linker X comprises the amino acid sequence RLQLKL. In some embodiments, the linker X comprises the amino acid sequence RLQLK(Ac).

In some embodiments, the linker X comprises a peptide selected from: PR(S/T)(L/I)(S/T), where the letters in parentheses indicate that either one of the indicated amino acids is at that position in the sequence); GGAANLVRGG; SGRIGFLRTA; SGRSA; GFLG; ALAL; FK; PIC(Et)F-F, where C(Et) indicates S-ethylcysteine (a cysteine with an ethyl group attached to the thiol) and the "–" indicates the typical cleavage site in this and subsequent sequences); GGPRGLPG; HSSKLQ; LVLA-SSSFGY; GVSQNY-PIVG; GVVQA-SCRLA; f(Pip)R-S, where "f" indicates D-phenylalanine and "Pip" indicates piperidine-2-carboxylic acid (pipecolinic acid, a proline analog having a six-membered ring); DEVD; GWEHDG; RPLALWRS, or a combination thereof.

In some embodiments, X is cleaved under hypoxic conditions. In some embodiments, X comprises a disulfide linkage. In some embodiments, X comprises a quinine.

In some embodiments, X is cleaved under necrotic conditions. In some embodiments, X comprises a molecule cleavable by a calpain.

In some embodiments, X comprises 6-aminohexanoyl, 5-(amino)-3-oxapentanoyl, or a combination thereof. In some embodiments, X comprises a disulfide linkage.

In some embodiments, the linker is an alkyl. In some embodiments, the linker is heteroalkyl.

In some embodiments, the linker is an alkylene. In some embodiments, the linker is an alkenylene. In some embodiments, the linker is an alkynylene. In some embodiments, the linker is a heteroalkylene.

An "alkyl" group refers to an aliphatic hydrocarbon group. The alkyl moiety may be a saturated alkyl or an unsaturated alkyl. Depending on the structure, an alkyl group may be a monoradical or a diradical (i.e., an alkylene group).

The "alkyl" moiety may have 1 to 10 carbon atoms (whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated). The alkyl group could also be a "lower alkyl" having 1 to 6 carbon atoms. The alkyl group of the compounds described herein may be designated as "C1-C4 alkyl" or similar designations. By way of example only, "C1-C4 alkyl" indicates that there are one to four carbon atoms in the alkyl chain, i.e., the alkyl chain is selected from: methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, ethenyl, propenyl, butenyl, and the like.

In some embodiments, the linker comprises a ring structure (e.g., an aryl). As used herein, the term "ring" refers to any covalently closed structure. Rings include, for example, carbocycles (e.g., aryls and cycloalkyls), heterocycles (e.g., heteroaryls and non-aromatic heterocycles), aromatics (e.g. aryls and heteroaryls), and non-aromatics (e.g., cycloalkyls and non-aromatic heterocycles). Rings can be optionally substituted. Rings can be monocyclic or polycyclic.

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, naphthalenyl, phenanthrenyl, anthracenyl, fluorenyl, and indenyl. Depending on the structure, an aryl group can be a monoradical or a diradical (i.e., an arylene group).

The term "cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyl groups include groups having from 3 to 10 ring atoms. Cycloalkyls include, but are not limited to, cyclopropyl, cyclobutyl, cyclopentyl, cyclohexyl, cycloheptyl, and cyclooctyl.

In some embodiments, the ring is a cycloalkane. In some embodiments, the ring is a cycloalkene.

In some embodiments, the ring is an aromatic ring. The term "aromatic" refers to a planar ring having a delocalized π-electron system containing 4n+2 π electrons, where n is an integer. Aromatic rings can be formed from five, six, seven, eight, nine, or more than nine atoms. Aromatics can be optionally substituted. The term "aromatic" includes both carbocyclic aryl (e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

In some embodiments, the ring is a heterocycle. The term "heterocycle" refers to heteroaromatic and heteroalicyclic groups containing one to four heteroatoms each selected from 0, S and N, wherein each heterocyclic group has from 4 to 10 atoms in its ring system, and with the proviso that the ring of said group does not contain two adjacent O or S atoms. Non-aromatic heterocyclic groups include groups having only 3 atoms in their ring system, but aromatic heterocyclic groups must have at least 5 atoms in their ring system. The heterocyclic groups include benzo-fused ring systems. An example of a 3-membered heterocyclic group is aziridinyl. An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups may be C-attached or N-attached where such is possible. For instance, a group derived from pyrrole is pyrrol-1-yl (N-attached) or pyrrol-3-yl (C-attached). Further, a group derived from imidazole is imidazol-1-yl or imidazol-3-yl (both N-attached) or imidazol-2-yl, imidazol-4-yl or imidazol-5-yl (all C-attached). The heterocyclic groups include benzo-fused ring systems and ring systems substituted with one or two oxo (=O) moieties such as pyrrolidin-2-one. Depending on the structure, a heterocycle group can be a monoradical or a diradical (i.e., a heterocyclene group).

In some embodiments, the ring is fused. The term "fused" refers to structures in which two or more rings share one or more bonds. In some embodiments, the ring is a dimer. In some embodiments, the ring is a trimer. In some embodiments, the ring is a substituted.

The term "carbocyclic" or "carbocycle" refers to a ring wherein each of the atoms forming the ring is a carbon atom. Carbocycle includes aryl and cycloalkyl. The term thus distinguishes carbocycle from heterocycle ("heterocyclic") in which the ring backbone contains at least one atom which is different from carbon (i.e., a heteroatom). Heterocycle includes heteroaryl and heterocycloalkyl. Carbocycles and heterocycles can be optionally substituted.

In some embodiments, the linker X is substituted. The term "optionally substituted" or "substituted" means that the referenced group may be substituted with one or more additional group(s) individually and independently selected from $C_1$-$C_6$alkyl, $C_3$-$C_8$cycloalkyl, aryl, heteroaryl, $C_2$-$C_6$heteroalicyclic, hydroxy, $C_1$-$C_6$alkoxy, aryloxy, $C_1$-$C_6$alkylthio, arylthio, $C_1$-$C_6$alkylsulfoxide, arylsulfoxide, $C_1$-$C_6$alkylsulfone, arylsulfone, cyano, halo, $C_2$-$C_8$acyl, $C_2$-$C_8$acyloxy, nitro, $C_1$-$C_6$haloalkyl, $C_1$-$C_6$fluoroalkyl, and amino, including $C_1$-$C_6$alkylamino, and the protected derivatives thereof. By way of example, an optional substituents may be LsRs, wherein each Ls is independently selected from a bond, —O—, —C(=O)—, —S—, —S(=O)—, —S(=O)2-, —NH—, —NHC(=O)—, —C(=O)NH—, S(=O)2NH—, —NHS(=O)2-, —OC(=O)NH—, —NHC(=O)O—, —($C_1$-$C_6$alkyl)-, or ($C_2$-$C_6$alkenyl)-; and each Rs is independently selected from H, ($C_1$-$C_4$alkyl), ($C_3$-$C_8$cycloalkyl), heteroaryl, aryl, and $C_1$-$C_6$heteroalkyl. Optionally substituted non-aromatic groups may be substituted with one or more oxo (=O). The protecting groups that may form the protective derivatives of the above substituents are known to those of skill in the art.

In some embodiments, a linker X comprises a zero-linker. In some instances, a zero-linker comprises a covalent bond. In some embodiments, the covalent bond comprises an ether bond, thioether bond, amine bond, amide bond, oxime bond, hydrazone, carbon-carbon bond, carbon-nitrogen bond, carbon-oxygen bond, or carbon-sulfur bond.

In some embodiments, a linker X further comprises a bifunctional linker. In some instances, a bifuctional linker has one functional group reactive with a group on a first molecule (e.g., a selective delivery molecule), and a second functional group reactive on a second molecule (e.g., an imaging cargo). In some cases, the bifunctional linker is a homobifunctional linker or a heterobifunctional linker. Alternatively, in some embodiments, derivatization is performed to provide functional groups. Thus, for example, procedures for the generation of free sulfhydryl groups on peptides are also known (See U.S. Pat. No. 4,659,839). The linker X may alternatively comprise a heterobifunctional crosslinker comprising two or more different reactive groups that form a heterocyclic ring that can interact with a selective delivery molecule. For example, a heterobifunctional crosslinker such as cysteine may comprise an amine reactive group and a thiol-reactive group can interact with an aldehyde on a derivatized selective delivery molecule. Additional combinations of reactive groups suitable for heterobifunctional crosslinkers include, for example, amine- and sulfhydryl reactive groups; carbonyl and sulfhydryl reactive groups; amine and photoreactive groups; sulfhydryl and photoreactive groups; carbonyl and photoreactive groups; carboxylate and photoreactive groups; and arginine and photoreactive groups.

Exemplary homobifuctional linkers include, but are not limited to, Lomant's reagent dithiobis (succinimidylpropionate) DSP, 3'3'-dithiobis(sulfosuccinimidyl proprionate) (DTSSP), disuccinimidyl suberate (DSS), bis(sulfosuccinimidyl)suberate (BS), disuccinimidyl tartrate (DST), di sulfosuccinimidyl tartrate (sulfo DST), ethylene glycobis (succinimidylsuccinate) (EGS), disuccinimidyl glutarate (DSG), N,N'-disuccinimidyl carbonate (DSC), dimethyl adipimidate (DMA), dimethyl pimelimidate (DMP), dimethyl suberimidate (DMS), dimethyl-3,3'-dithiobispropionimidate (DTBP), 1,4-di-3'-(2'-pyridyldithio)propionamido)butane (DPDPB), bismaleimidohexane (BMH), aryl halide-containing compound (DFDNB), such as e.g. 1,5-difluoro-2,4-dinitrobenzene or 1,3-difluoro-4,6-dinitrobenzene, 4,4'-difluoro-3,3'-dinitrophenylsulfone (DFDNPS), bis-[β-(4-azidosalicylamido)ethyl]disulfide (BASED), formaldehyde, glutaraldehyde, 1,4-butanediol diglycidyl ether, adipic acid dihydrazide, carbohydrazide, o-toluidine, 3,3'-dimethylbenzidine, benzidine, α,α'-p-diaminodiphenyl, diiodo-p-xylene sulfonic acid, N,N'-ethylene-bis(iodoacetamide), or N,N'-hexamethylene-bis(iodoacetamide).

Exemplary heterobifunctional linker include, but are not limited to, amine-reactive and sulfhydryl cross-linkers such as N-succinimidyl 3-(2-pyridyldithio)propionate (sPDP), long-chain N-succinimidyl 3-(2-pyridyldithio)propionate (LC-sPDP), water-soluble-long-chain N-succinimidyl 3-(2-pyridyldithio) propionate (sulfo-LC-sPDP), succinimidyloxycarbonyl-α-methyl-α-(2-pyridyldithio)toluene (sMPT), sulfosuccinimidyl-6-[α-methyl-α-(2-pyridyldithio)toluamido]hexanoate (sulfo-LC-sMPT), succinimidyl-4-(N-maleimidomethyl)cyclohexane-1-carboxylate (sMCC), sulfosuccinimidyl-4-(N-maleimidomethyl)cyclohexane-1-carboxylate (sulfo-sMCC), m-maleimidobenzoyl-N-hydroxysuccinimide ester (MBs), m-maleimidobenzoyl-N-hydroxysulfosuccinimide ester (sulfo-MBs), N-succinimidyl(4-iodoacteyl)aminobenzoate (sIAB), sulfosuccinimidyl(4-iodoacteyl)aminobenzoate (sulfo-sIAB), succinimidyl-4-(p-maleimidophenyl)butyrate (sMPB), sulfosuccinimidyl-4-(p-maleimidophenyl)butyrate (sulfo-sMPB), N-(γ-maleimidobutyryloxy)succinimide ester (GMBs), N-(γ-maleimidobutyryloxy)sulfosuccinimide ester (sulfo-GMBs), succinimidyl 6-((iodoacetyl)amino)hexanoate (sIAX), succinimidyl 6-[6-(((iodoacetyl)amino) hexanoyl)amino]hexanoate (sIAXX), succinimidyl 4-(((iodoacetyl)amino)methyl)cyclohexane-1-carboxylate (sIAC), succinimidyl 6-((((4-iodoacetyl)amino)methyl)cyclohexane-1-carbonyl)amino) hexanoate (sIACX), p-nitrophenyl iodoacetate (NPIA), carbonyl-reactive and sulfhydryl-reactive cross-linkers such as 4-(4-N-maleimidophenyl) butyric acid hydrazide (MPBH), 4-(N-maleimidomethyl) cyclohexane-1-carboxyl-hydrazide-8 (M2C2H), 3-(2-pyridyldithio)propionyl hydrazide (PDPH), amine-reactive and photoreactive cross-linkers such as N-hydroxysuccinimidyl-4-azidosalicylic acid (NHs-AsA), N-hydroxysulfosuccinimidyl-4-azidosalicylic acid (sulfo-NHs-AsA), sulfosuccinimidyl-(4-azidosalicylamido)hexanoate (sulfo-NHs-LC-AsA), sulfosuccinimidyl-2-(ρ-azidosalicylamido)ethyl-1,3'-dithiopropionate (sAsD), N-hydroxysuccinimidyl-4-azidobenzoate (HsAB), N-hydroxysulfosuccinimidyl-4-azidobenzoate (sulfo-HsAB), N-succinimidyl-6-(4'-azido-2'-nitrophenylamino)hexanoate (sANPAH), sulfosuccinimidyl-6-(4'-azido-2'-nitrophenylamino)hexanoate (sulfo-sANPAH), N-5-azido-2-nitrobenzoyloxysuccinimide (ANB-NOs), sulfosuccinimidyl-2-(m-azido-o-nitrobenzamido)-ethyl-1,3'-dithiopropionate (sAND), N-succinimidyl-4(4-azidophenyl)1,3'-dithiopropionate (sADP), N-sulfosuccinimidyl(4-azidophenyl)-1,3'-dithiopropionate (sulfo-sADP), sulfosuccinimidyl 4-(ρ-azidophenyl)butyrate (sulfo-sAPB), sulfosuccinimidyl 2-(7-azido-4-methylcoumarin-3-acetamide)ethyl-1,3'-dithiopropionate (sAED), sulfosuccinimidyl 7-azido-4-methylcoumain-3-acetate (sulfo-sAMCA), ρ-nitrophenyl diazopyruvate (ρNPDP), ρ-nitrophenyl-2-diazo-3,3,3-trifluoropropionate (PNP-DTP), sulfhydryl-reactive and photoreactive cross-linkers such as 1-(ρ-Azidosalicylamido)-4-(iodoacetamido) butane (AsIB), N-[4-(ρ-azidosalicylamido)butyl]-3'-(2'-pyridyldithio)propionamide (APDP), benzophenone-4-iodoacetamide, benzophenone-4-maleimide carbonyl-reactive and photoreactive cross-linkers such as ρ-azidobenzoyl hydrazide (ABH), carboxylate-reactive and photoreactive cross-linkers such as 4-(ρ-azidosalicylamido) butylamine (AsBA), and arginine-reactive and photoreactive cross-linkers such as ρ-azidophenyl glyoxal (APG).

In some instances, the linker X further comprises a reactive functional group. In some embodiments, the reactive functional group conjugates the linker X to the cargo described herein. In some cases, the reactive functional group comprises a nucleophilic group that is reactive to an electrophilic group. Exemplary electrophilic groups include carbonyl groups—such as aldehyde, ketone, carboxylic acid, ester, amide, enone, acyl halide or acid anhydride. In some embodiments, the reactive functional group is aldehyde. Exemplary nucleophilic groups include hydrazide, oxime, amino, hydrazine, thiosemicarbazone, hydrazine carboxylate, and arylhydrazide.

In some embodiments, the linker X comprises a maleimide group, an alkyl halide group, or an iodoacetamide group.

In some embodiments, the linker X comprises a maleimide group. In some instances, the maleimide group is also referred to as a maleimide spacer. In some instances, the maleimide group further encompasses a caproic acid, forming maleimidocaproyl (mc). In some cases, the linker comprises maleimidocaproyl (mc). In some cases, the linker is maleimidocaproyl (mc). In other instances, the maleimide group comprises a maleimidomethyl group, such as succinimidyl-4-(N-maleimidomethyl)cyclohexane-1-carboxylate (sMCC) or sulfosuccinimidyl-4-(N-maleimidomethyl)cyclohexane-1-carboxylate (sulfo-sMCC) described above.

In some embodiments, the maleimide group is a self-stabilizing maleimide. In some instances, the self-stabilizing maleimide utilizes diaminopropionic acid (DPR) to incorporate a basic amino group adjacent to the maleimide to provide intramolecular catalysis of tiosuccinimide ring hydrolysis, thereby eliminating maleimide from undergoing an elimination reaction through a retro-Michael reaction. In some instances, the self-stabilizing maleimide is a maleimide group described in Lyon, et al., "Self-hydrolyzing maleimides improve the stability and pharmacological properties of antibody-drug conjugates," Nat. Biotechnol. 32(10): 1059-1062 (2014). In some instances, the linker comprises a self-stabilizing maleimide. In some instances, the linker is a self-stabilizing maleimide.

In some embodiments, a selective delivery molecules disclosed herein comprises a single linker. Use of a single mechanism to mediate uptake of both imaging and therapeutic cargoes is particularly valuable, because imaging with non-injurious tracer quantities can be used to test whether a subsequent therapeutic dose is likely to concentrate correctly in the target tissue.

In some embodiments, a selective delivery molecules disclosed herein comprises a plurality of linkers. Where a selective delivery molecule disclosed herein includes multiple X linkages, separation of portion A from the other portions of the molecule requires cleavage of all X linkages. Cleavage of multiple X linkers may be simultaneous or sequential. Multiple X linkages may include X linkages having different specificities, so that separation of portion A from the other portions of the molecule requires that more than one condition or environment (e.g., "signal" or "extracellular signal") be encountered by the molecule. Cleavage of multiple X linkers thus serves as a detector of combinations of such signals or extracellular signals. For example, a selective delivery molecule may include two linker portions Xa and Xb connecting basic portion B with acidic portion A. Both Xa and Xb linkers must be cleaved before acidic portion A is separated from basic portion B allowing entry of portion B and cargo moiety C (if any) to enter a cell. It will be understood that a linker region may link to either a basic portion B or a cargo moiety C independently of another linker that may be present, and that, where desired, more than two linker regions X may be included.

Combinations of two or more X linkers may be used to further modulate the targeting and delivery of molecules to desired cells, tissue or regions. Combinations of signals or extracellular signals are used to widen or narrow the specificity of the cleavage of X linkers if desired. Where multiple X linkers are linked in parallel, the specificity of cleavage is narrowed, since each X linker must be cleaved before portion A may separate from the remainder of the molecule. Where multiple X linkers are linked in series, the specificity of cleavage is broadened, since cleavage on any one X linker allows separation of portion A from the remainder of the molecule. For example, in order to detect either a protease OR hypoxia (i.e., to cleave X in the presence of either protease or hypoxia), a X linker is designed to place the protease-sensitive and reduction-sensitive sites in tandem, so that cleavage of either would suffice to allow separation of the acidic portion A. Alternatively, in order to detect the presence of both a protease AND hypoxia (i.e., to cleave X in the presence of both protease and hypoxia but not in the presence of only one alone), a X linker is designed to place the protease sensitive site between at least one pair of cysteines that are disulfide-bonded to each other. In that case, both protease cleavage and disulfide reduction are required in order to allow separation of portion A.

Portion Y Linker

In some embodiments, Y is a linker consisting of one or more amino acids is used to join Cargo (D) to the remainder of the SDM. In some embodiments, Y is a linker consisting of one or more amino acids is used to join Cargo (D) to portion B. Generally, the peptide linker will have no specific biological activity other than to join the molecules or to preserve some minimum distance or other spatial relationship between them. However, the constituent amino acids of the linker may be selected to influence some property of the molecule such as the folding, net charge, or hydrophobicity.

In some embodiments, a Y linker binds cargo portion of D to peptide portion of B (i.e., the delivery sequence) by a covalent linkage. In some embodiments, the covalent linkage comprises an ether bond, thioether bond, amine bond, amide bond, oxime bond, hydrazone bond, carbon-carbon bond, carbon-nitrogen bond, carbon-oxygen bond, or carbon-sulfur bond.

In some embodiments, a Y linker is flexible. In some embodiments, the Y linker is rigid. In some embodiments, the Y linker comprises a linear structure. In some embodiments, the Y linker comprises a non-linear structure. In some embodiments, the Y linker comprises a branched structure. In some embodiments, the linker comprises a cyclic structure.

In some embodiments, a Y linker comprises a peptide linkage. The peptide linkage comprises L-amino acids and/or D-amino acids. In embodiments, D-amino acids are preferred in order to minimize immunogenicity and nonspecific cleavage by background peptidases or proteases. Cellular uptake of oligo-D-arginine sequences is known to be as good as or better than that of oligo-L-arginines.

In some embodiments, a Y linker is a non-cleavable linker.

In some embodiments, a Y linker is designed for cleavage in the presence of particular conditions or in a particular environment. In some embodiments, a Y linker is cleavable by an intracellular protease. In some embodiments, Y is cleavable by an intracellular protease. In some embodiments, a Y linker is cleavable by a lysosomal protease. In some embodiments, the intracellular protease is a cysteine protease. In some embodiments, the intracellular protease is an aspartyl protease. In some embodiments, the intracellular protease is a serine protease. In some embodiments, the cysteine protease is a caspase, a cathepsin, calpain, papain or a legumain. In some embodiments, the intracellular protease is an initiator caspase. In some embodiments, the intracellular protease is an effector caspase. In some embodiments, the Y linker is cleavable by a protease selected from among cathepsin B, cathepsin L, cathepsin H, cathepsin K, cathepsin W, cathepsin C, cathepsin F, cathepsin V, cathepsin X, cathepsin S, cathepsin D, cathepsin G, HCP-1, HCP-2, dipeptidyl-peptidase I, MEROPS C13, CED-3 peptidase, caspase 2, caspase 3, caspase 6, caspase 7, caspase 8, caspase 9, caspase 10, caspase 11; caspase 12, caspase 13, and caspase 14. In some embodiments, the Y linker is cleavable by a protease selected from among cathepsin B, cathepsin L, caspase 3, caspase 7, caspase 8, and caspase 9. In some embodiments, a Y linker is cleavable by Cathepsin B a dipeptidyl carboxypeptidase. In some embodiments the linker has a lysine, citrulline, or arginine residue at the P1 position and a large hydrophobic residue at the P1' position.

In some embodiments, a Y linker comprises an acid sensitive chemical linker. In some embodiments, acid sensitive chemical linker is hydrazone or a derivative thereof. In some embodiments, a Y linker comprises a self-immolative spacer. In some embodiments, the self-immolative spacer is of sufficient length to prevent the occurrence of steric hindrance between the B portion of the SDM and the therapeutic cargo. In some embodiments, Y comprises a p-aminobenzyl alcohol (PABOH) spacer or a derivative thereof. In some embodiments, Y comprises a p-aminobenzyl carbonyl (PABC) spacer or a derivative thereof. In some embodiments, Y comprises a branched bis(hydroxymethyl) styrene (BHMS) spacer or a derivative thereof. In some embodiments, Y comprises a 2-aminoimidazol-5-methanol derivative or an ortho or para-aminobenzylacetal spacer. In some embodiments Y comprises 2,6-bishydroxymethyl-p-cresol or hemithioaminal derivatives.

In some embodiments, a Y linker comprises a bifunctional linker. In some instances, a bifuctional linker has one functional group reactive with a group on a first molecule (e.g., a selective delivery molecule), and a second functional group reactive on a second molecule (e.g., an imaging cargo). In some cases, the bifunctional linker is a homobifunctional linker or a heterobifunctional linker. Alternatively, in some embodiments, derivatization is performed to provide functional groups. Thus, for example, procedures for the generation of free sulfhydryl groups on peptides are also known (See U.S. Pat. No. 4,659,839). A linker may alternatively comprise a heterobifunctional crosslinker comprising two or more different reactive groups that form a heterocyclic ring that can interact with a selective delivery molecule. For example, a heterobifunctional crosslinker such as cysteine may comprise an amine reactive group and a thiol-reactive group can interact with an aldehyde on a derivatized selective delivery molecule. Additional combinations of reactive groups suitable for heterobifunctional crosslinkers include, for example, amine- and sulfhydryl reactive groups; carbonyl and sulfhydryl reactive groups; amine and photoreactive groups; sulfhydryl and photoreactive groups; carbonyl and photoreactive groups; carboxylate and photoreactive groups; and arginine and photoreactive groups.

Exemplary homobifunctional linkers include, but are not limited to, Lomant's reagent dithiobis (succinimidylpropionate) DSP, 3'3'-dithiobis(sulfosuccinimidyl proprionate (DTSSP), disuccinimidyl suberate (DSS), bis(sulfosuccinimidyl)suberate (BS), disuccinimidyl tartrate (DST), di sulfosuccinimidyl tartrate (sulfo DST), ethylene glycobis (succinimidylsuccinate) (EGS), disuccinimidyl glutarate (DSG), N,N'-disuccinimidyl carbonate (DSC), dimethyl adipimidate (DMA), dimethyl pimelimidate (DMP), dimethyl suberimidate (DMS), dimethyl-3,3'-dithiobispropionimidate (DTBP), 1,4-di-3'-(2'-pyridyldithio)propionamido)butane (DPDPB), bismaleimidohexane (BMH), aryl halide-containing compound (DFDNB), such as e.g. 1,5-difluoro-2,4-dinitrobenzene or 1,3-difluoro-4,6-dinitrobenzene, 4,4'-difluoro-3,3'-dinitrophenylsulfone (DFDNPS), bis-[β-(4-azidosalicylamido)ethyl]disulfide (BASED), formaldehyde, glutaraldehyde, 1,4-butanediol diglycidyl ether, adipic acid dihydrazide, carbohydrazide, o-toluidine, 3,3'-dimethylbenzidine, benzidine, α,α'-p-diaminodiphenyl, diiodo-p-xylene sulfonic acid, N,N'-ethylene-bis(iodoacetamide), or N,N'-hexamethylene-bis(iodoacetamide).

Exemplary heterobifunctional linker include, but are not limited to, amine-reactive and sulfhydryl cross-linkers such as N-succinimidyl 3-(2-pyridyldithio)propionate (sPDP), long-chain N-succinimidyl 3-(2-pyridyldithio)propionate (LC-sPDP), water-soluble-long-chain N-succinimidyl 3-(2-pyridyldithio) propionate (sulfo-LC-sPDP), succinimidyloxycarbonyl-α-methyl-α-(2-pyridyldithio)toluene (sMPT), sulfosuccinimidyl-6-[α-methyl-α-(2-pyridyldithio)toluamido]hexanoate (sulfo-LC-sMPT), succinimidyl-4-(N-maleimidomethyl)cyclohexane-1-carboxylate (sMCC), sulfosuccinimidyl-4-(N-maleimidomethyl)cyclohexane-1-carboxylate (sulfo-sMCC), m-maleimidobenzoyl-N-hydroxysuccinimide ester (MBs), m-maleimidobenzoyl-N-hydroxysulfosuccinimide ester (sulfo-MBs), N-succinimidyl(4-iodoacteyl)aminobenzoate (sIAB), sulfosuccinimidyl(4-iodoacteyl)aminobenzoate (sulfo-sIAB), succinimidyl-4-(p-maleimidophenyl)butyrate (sMPB), sulfosuccinimidyl-4-(p-maleimidophenyl)butyrate (sulfo-sMPB), N-(γ-maleimidobutyryloxy)succinimide ester (GMBs), N-(γ-maleimidobutyryloxy)sulfosuccinimide ester (sulfo-GMBs), succinimidyl 6-((iodoacetyl)amino)hexanoate (sIAX), succinimidyl 6-[6-(((iodoacetyl)amino) hexanoyl)amino]hexanoate (sIAXX), succinimidyl 4-(((iodoacetyl)amino)methyl)cyclohexane-1-carboxylate (sIAC), succinimidyl 6-((((4-iodoacetyl)amino)methyl)cyclohexane-1-carbonyl)amino) hexanoate (sIACX), p-nitrophenyl iodoacetate (NPIA), carbonyl-reactive and sulfhydryl-reactive cross-linkers such as 4-(4-N-maleimidophenyl) butyric acid hydrazide (MPBH), 4-(N-maleimidomethyl) cyclohexane-1-carboxyl-hydrazide-8 (M2C2H), 3-(2-pyridyldithio)propionyl hydrazide (PDPH), amine-reactive and photoreactive cross-linkers such as N-hydroxysuccinimidyl-4-azidosalicylic acid (NHs-AsA), N-hydroxysulfosuccinimidyl-4-azidosalicylic acid (sulfo-NHs-AsA), sulfosuccinimidyl-(4-azidosalicylamido)hexanoate (sulfo-NHs-LC-AsA), sulfosuccinimidyl-2-(p-azidosalicylamido)ethyl-1,3'-dithiopropionate (sAsD), N-hydroxysuccinimidyl-4-azidobenzoate (HsAB), N-hydroxysulfosuccinimidyl-4-azidobenzoate (sulfo-HsAB), N-succinimidyl-6-(4'-azido-2'-nitrophenylamino)hexanoate (sANPAH), sulfosuccinimidyl-6-(4'-azido-2'-nitrophenylamino)hexanoate (sulfo-sANPAH), N-5-azido-2-nitrobenzoyloxysuccinimide (ANB-NOs), sulfosuccinimidyl-2-(m-azido-o-nitrobenzamido)-ethyl-1,3'-dithiopropionate (sAND), N-succinimidyl-4(4-azidophenyl)1,3'-dithiopropionate (sADP), N-sulfosuccinimidyl(4-azidophenyl)-1,3'-dithiopropionate (sulfo-sADP), sulfosuccinimidyl 4-(p-azidophenyl)butyrate (sulfo-sAPB), sulfosuccinimidyl 2-(7-azido-4-methylcoumarin-3-acetamide)ethyl-1,3'-dithiopropionate (sAED), sulfosuccinimidyl 7-azido-4-methylcoumain-3-acetate (sulfo-sAMCA), p-nitrophenyl diazopyruvate (pNPDP), p-nitrophenyl-2-diazo-3,3,3-trifluoropropionate (PNP-DTP), sulfhydryl-reactive and photoreactive cross-linkers such as 1-(p-Azidosalicylamido)-4-(iodoacetamido) butane (AsIB), N-[4-(p-azidosalicylamido)butyl]-3'-(2'-pyridyldithio)propionamide (APDP), benzophenone-4-iodoacetamide, benzophenone-4-maleimide carbonyl-reactive and photoreactive cross-linkers such as p-azidobenzoyl hydrazide (ABH), carboxylate-reactive and photoreactive cross-linkers such as 4-(p-azidosalicylamido) butylamine (AsBA), and arginine-reactive and photoreactive cross-linkers such as p-azidophenyl glyoxal (APG).

In some embodiments, a linker Y comprises a maleimide group. In some instances, the maleimide group is also referred to as a maleimide spacer. In some instances, the maleimide group further encompasses a caproic acid, forming maleimidocaproyl (mc). In some cases, the linker comprises maleimidocaproyl (mc). In some cases, the linker is maleimidocaproyl (mc). In other instances, the maleimide group comprises a maleimidomethyl group, such as succinimidyl-4-(N-maleimidomethyl)cyclohexane-1-carboxylate (sMCC) or sulfosuccinimidyl-4-(N-maleimidomethyl)cyclohexane-1-carboxylate (sulfo-sMCC) described above.

In some embodiments, the maleimide group is a self-stabilizing maleimide. In some instances, the self-stabilizing maleimide utilizes diaminopropionic acid (DPR) to incorporate a basic amino group adjacent to the maleimide to provide intramolecular catalysis of tiosuccinimide ring hydrolysis, thereby eliminating maleimide from undergoing an elimination reaction through a retro-Michael reaction. In some instances, the self-stabilizing maleimide is a maleimide group described in Lyon, et al., "Self-hydrolyzing maleimides improve the stability and pharmacological properties of antibody-drug conjugates," Nat. Biotechnol. 32(10): 1059-1062 (2014). In some instances, the linker comprises a self-stabilizing maleimide. In some instances, the linker is a self-stabilizing maleimide.

In some embodiments, a Y linker comprises the lysosomally cleavable peptide. In some embodiments, the Y linker comprises the lysosomally cleavable dipeptide Phe-Arg. In some embodiments, the Y linker comprises the lysosomally cleavable dipeptide Phe-Lys. In some embodiments, the Y linker comprises the lysosomally cleavable dipeptide Val-Cit (l-citrulline). In some embodiments, the Y linker comprises the lysosomally cleavable tetrapeptide Gly-Phe-Leu-Gly. In some embodiments, the Y linker comprises the lysosomally cleavable tetrapeptide Ala-Leu-Ala-Leu.

In some embodiments, a Y linker comprises the lysosomally cleavable peptide and a self-immolative spacer.

In some embodiments, Y is a pH-sensitive linker. In some embodiments, Y is cleaved under acidic pH conditions. In some embodiments, Y is cleaved under acidic pH conditions of the lysosome.

It will be understood that a Y linker disclosed herein may include non-standard amino acids, such as, for example, hydroxylysine, desmosine, isodesmosine, or other non-standard amino acids. A linker disclosed herein may include modified amino acids, including post-translationally modified amino acids such as, for example, methylated amino acids (e.g., methyl histidine, methylated forms of lysine, etc.), acetylated amino acids, amidated amino acids, formylated amino acids, hydroxylated amino acids, phosphorylated amino acids, or other modified amino acids. A linker disclosed herein may also include peptide mimetic moieties, including portions linked by non-peptide bonds and amino acids linked by or to non-amino acid portions.

Additional Modifications

In some embodiments, the selective delivery molecules of the present disclosure are optionally conjugated to high molecular weight molecules that increase the multivalency and avidity of labeling. In some embodiments, the high molecular weight molecules are water-soluble polymers. Examples of suitable water-soluble polymers include, but are not limited to, peptides, saccharides, poly(vinyls), poly(ethers), poly(amines), poly(carboxylic acids) and the like. In some embodiments, the water-soluble polymer is dextran, polyethylene glycol (PEG), polyoxyalkylene, polysialic acid, starch, or hydroxyethyl starch. Any suitable method is used to conjugate peptides to water-soluble polymers (see Hermanson G., Bioconjugate Techniques $2^{nd}$ Ed., Academic Press, Inc. 2008).

Exemplary Selective Delivery Molecule for Ratiometric Imaging

FIG. 1 shows the structure of one non-limiting example of a selective delivery molecule for use in the disclosed ratiometric fluorescence imaging methods (i.e., SDM-25 or AVB-620). SDM-25 is used in fluorescence imaging methods to deliver a pair of fluorescence donor and acceptor moieties (i.e., imaging agents) that are capable of undergoing fluorescence resonance energy transfer (for example, Cy5 and Cy7) to a tissue of interest, the method comprising (a) contacting the tissue of interest with SDM-25 (e.g., administering SDM-25 to an individual intravenously), and (b) visualizing at least one of the imaging agents.

Figure 2B:
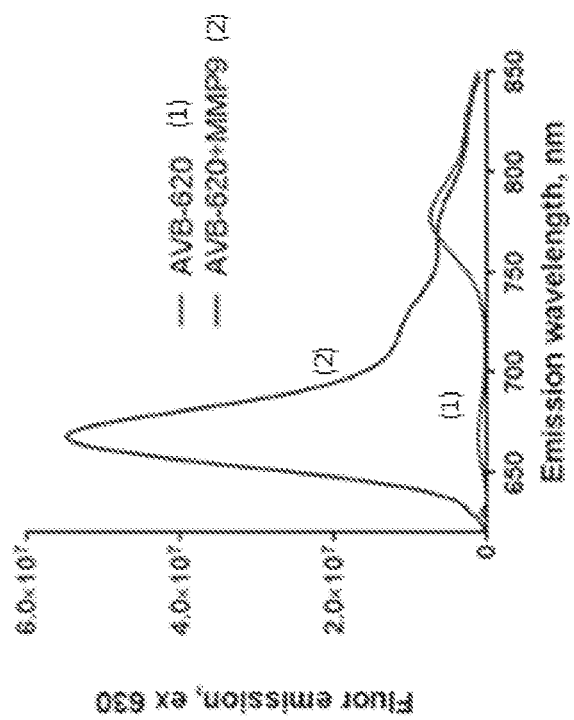
FIG. 2A-FIG. 2B illustrate absorbance and fluorescence emission spectra for SDM-25, a ratiometric ACPP (RACPP) comprising a polyanionic domain that is conjugated to a Cy7 moiety and is connected via a cleavable linker to a polycationic domain that is conjugated to a Cy5 moiety.
Figure 2A:
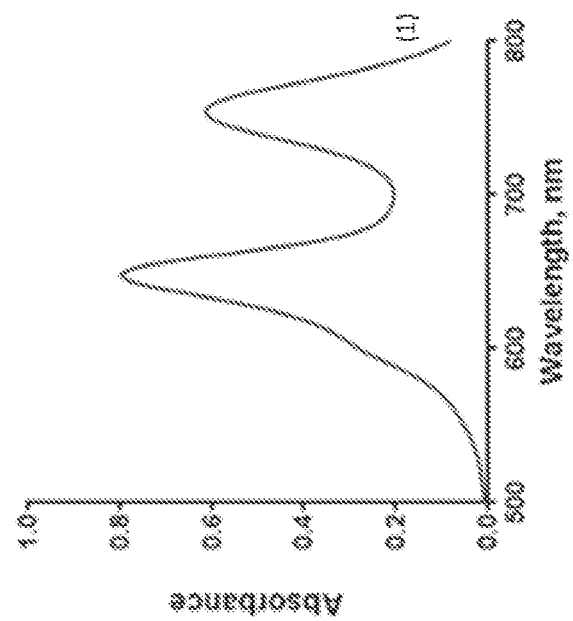

FIG. 2B illustrates the shift in fluorescence emission spectra for a ratiometric SDM-25 labeled with a Cy5/Cy7 donor-acceptor pair upon cleavage of the linker that holds the donor and acceptor in close proximity. For the intact probe, the FRET-based transfer of energy absorbed by the Cy5 donor molecule when excited with 620 nm light to the Cy7 acceptor molecule results in a strong fluorescence emission at approximately 780 nm. Upon cleavage, the separation of the two fluorophores eliminates the FRET-based transfer of energy, resulting in a decrease in Cy7 fluorescence emission at 780 nm and an increase in Cy5 fluorescence emission at 670 nm.

Figure 3A:
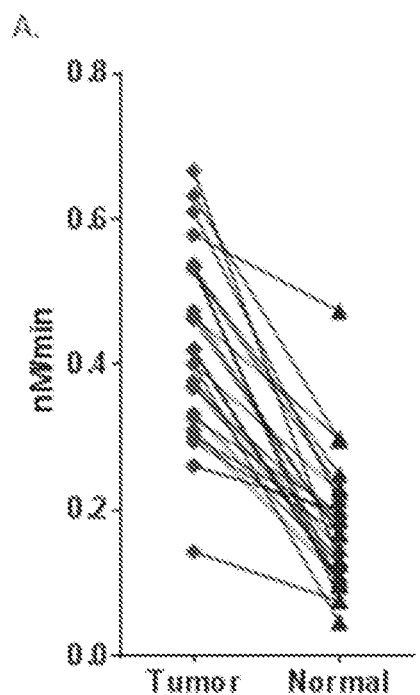
FIG. 3A-FIG. 3C provide examples of data illustrating the different cleavage rates observed for SDM-25 (AVB-620) in human breast cancer tumor tissue and normal tissue, and the Receiver Operator Characteristic (ROC) curve for of the use of SDM-25 in ratiometric fluorescence imaging-based detection of human breast cancer tissue.
Figure 3B:
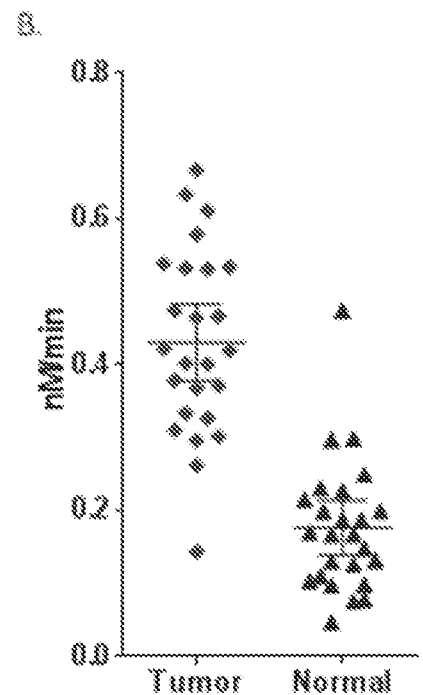
Figure 3C:
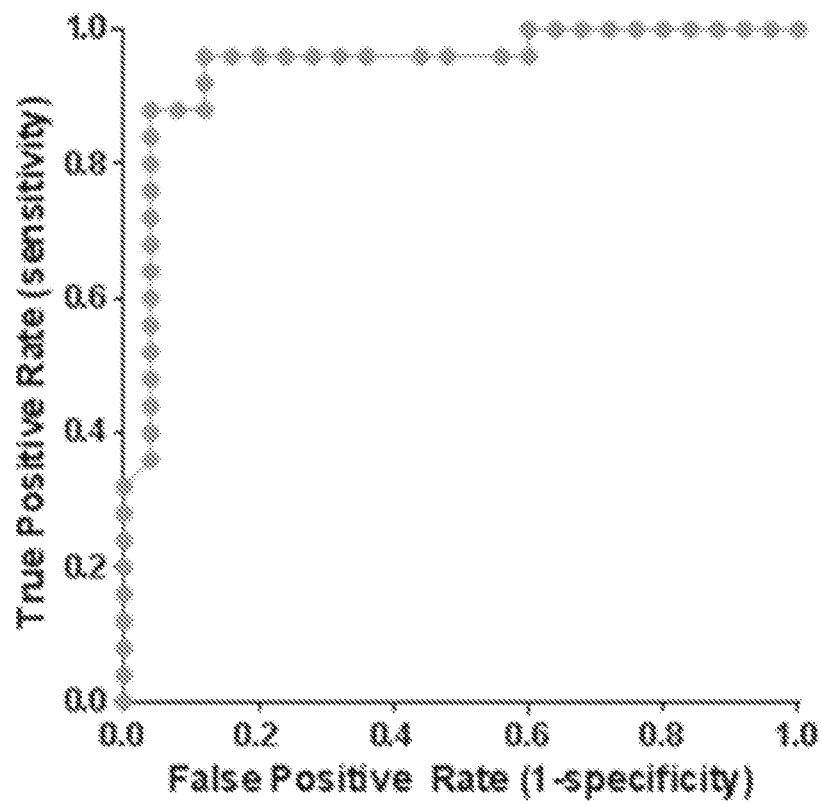

FIG. 3A-FIG. 3C provide examples of data illustrating the different cleavage rates observed for SDM-25 (AVB-620) in human breast cancer tumor tissue and normal tissue, and the Receiver Operator Characteristic (ROC) curve for the use of SDM-25 in ratiometric fluorescence imaging-based detection of human breast cancer tissue. FIG. 3A: SDM-25 cleavage rate (nM cleaved per minute) in 25 paired human breast cancer patient tissue homogenates. Cancer-positive tumor tissue (red diamonds) and cancer-negative adjacent tissue (blue triangles) are shown. Paired samples are connected by lines. Paired t-test gave P<0.0001 for significant difference between tumor and normal. FIG. 3B: Scatter plot of the same data with mean±95% confidence level. FIG. 3C: shows the ROC curve for SDM-25 cleavage rate detection of tumor versus normal tissue.

As indicated in FIG. 3A-FIG. 3B, upon incubation of normal human breast and cancerous human breast tissue homogenates with Cy5/Cy7 labeled SDM-25, enzymatic activity and SDM-25 cleavage was found to be significantly greater in cancerous human breast tissue compared to normal human breast tissue.

Figure 4A:
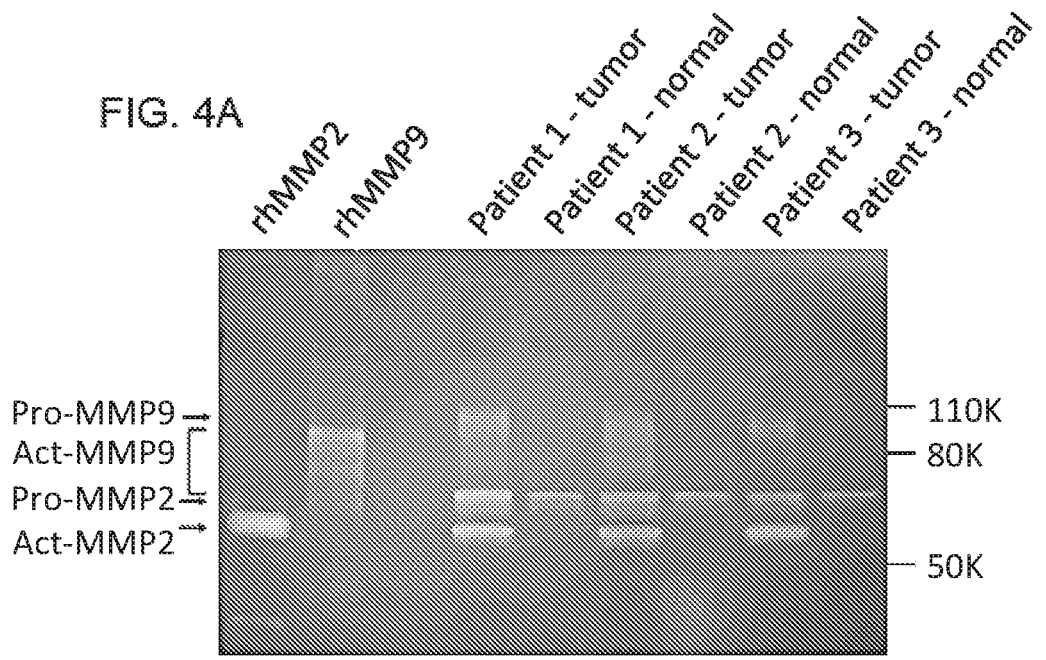
FIG. 4A-FIG. 4B provide examples of data illustrating the use of SDM-25 for quantification of MMP activity in non-malignant breast tissue and tumor homogenates.
Figure 4B:
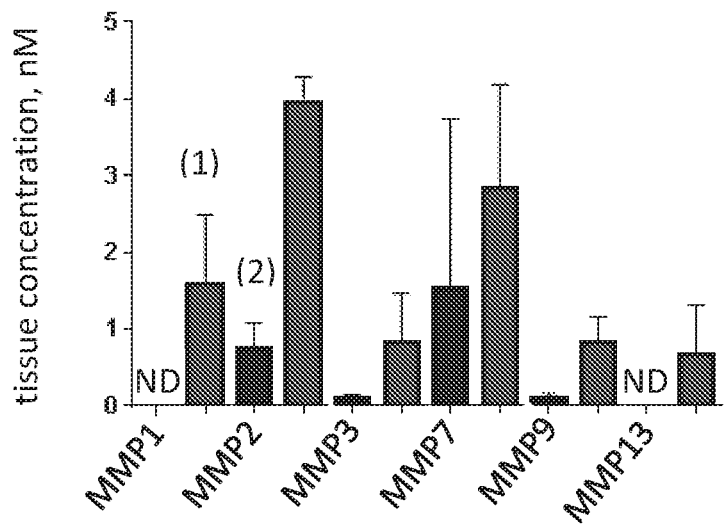

FIG. 4A-FIG. 4B provide examples of data illustrating the use of SDM-25 for quantification of MMP activity in non-malignant breast tissue and tumor homogenates. FIG. 4A: homogenates from three representative human breast cancer samples and paired normal tissue, selected from the 25 patients for which data is presented in FIG. 3A-FIG. 3C, were analyzed on a 10% gelatin zymogram. Recombinant active MMP2 and MMP9 were shown as standards (2 ng per lane). FIG. 4B: ELISA quantification of six MMPs in five representative human breast cancer samples (red) and paired normal tissue (blue), including the three pairs shown in FIG. 4A. Error bars are standard deviations. ND=not detectable.

In some instances, infusion of a biological specimen with Cy5/Cy7 labeled SDM-25 (or other ratiometric indicator) allows discrimination between regions exhibiting the biological activity of interest and those that do not with high image contrast ratios. For example, infusion of a biological specimen with Cy5/Cy7 labeled SDM-25 (or other ratiometric indicator) may provide a fluorescence ratio image or fluorescence intensity image contrast ratio of at least 1.25:1, 1.5:1, 1.75:1, 2:1, 3:1, 4:1, 5:1, 10:1, 20:1, or greater, between regions exhibiting protease activity correlated with cancer and those that do not.

Methods of Use

As noted above, the disclosed ratiometric fluorescence indicators and imaging methods may be used to detect and/or visualize regions within a biological specimen that exhibit a biological activity of interest. Examples of "biological specimen" include, but are not limited to, cultured cell samples, primary cell samples (e.g., tissue samples in which the extracellular matrix has been digested or dissolved to release individual cells into suspension), blood samples or fractions thereof, ex vivo tissue samples (e.g., biopsy samples or excised surgical samples), in vivo tissue samples (e.g., tumor tissue or margin tissue exposed during a surgical procedure), and the like. The biological specimens may be collected from any of a variety of organisms, e.g. prokaryotes, eukaryotes, fungi, plants, animals, or humans. In some instances, the biological specimens are patient samples. Examples of "biological activity" include, but are not limited to, changes in ion concentration or transport activity (e.g., accumulation of or release of Ca2+ ions, or changes in local pH), changes in the transmembrane potential of excitable cells, areas of enhanced protease activity (e.g., extracellular protease activity), changes in other biochemical or physiological processes that are monitored using ratiometric fluorescent indicators, or any combination thereof. In some instances, the biological activity to be detected and visualized is correlated with various disease states, e.g., arthritis, atherosclerosis, cancer, breast cancer, pre-cancer, malignant tissue, coagulation (blood clotting), inflammation, or any combination thereof.

In some embodiments, the disclosed ratiometric fluorescence indicators are used to detect and diagnose cancer in ex vivo tissue samples (e.g., biopsy samples or excised surgical samples).

In some embodiments, the disclosed ratiometric fluorescence indicators and imaging methods are used to visualize a tissue of interest in an individual in need thereof (e.g., a patient). In some embodiments, the ratiometric imaging methods comprise: (a) administering a ratiometric fluorescent indicator, e.g., a ratiometric ACPP such as SDM-25 labeled with a Cy5/Cy7 donor-acceptor pair, to the individual, and (b) visualizing at least one of the fluorescent species.

In some embodiments, targeted delivery of a ratiometric fluorescence indicator to a cell or tissue enables a medical professional to visualize/image a specific tissue (e.g., cancerous tissue). In some embodiments, targeted delivery of an imaging agent to a cell or tissue enables a medical professional to remove (or, surgically excise) the tissue of interest (e.g., cancerous tissue). In some embodiments, targeted delivery of an imaging agent to a cell or tissue enables a medical professional to remove (or, surgically excise) the tissue of interest (e.g., cancerous tissue) with a decrease in surgical margins. In some embodiments, targeted delivery of an imaging agent to a cell or tissue enables a medical professional to remove (or, surgically excise) a tumor/cancerous tissue and decreases the chance that some of the tumor/cancerous tissue will not be removed. In some embodiments, targeted delivery of an imaging agent to a cell or tissue enables a medical professional to maximally debulk a tumor/cancerous tissue. In some embodiments, targeted delivery of an imaging agent to cancerous breast tissue decreases the chances of an unnecessary operations and re-operations. In some embodiments, the cancer margin status is assessed intraoperatively.

In some embodiments, targeted delivery of an imaging agent to a cell or tissue enables a medical professional to more accurately sample (e.g., biopsy (e.g., excision biopsy, incision, biopsy, aspiration biopsy, or needle biopsy)) tissue of interest (e.g., cancerous tissue). In some embodiments, targeted delivery of an imaging agent to a cell or tissue enables a medical professional to visualize/image a specific tissue (e.g., cancerous tissue) within an excised tissue containing healthy tissue. Enabling identification of target tissue (e.g., cancerous tissue) can guide the pathologist on where to section a tissue sample for pathological evaluation and decreases the chances of a pathologist missing unhealthy tissue (e.g., cancerous tissue) and sampling healthy tissue which produces a false negative. In some embodiments, tissue (e.g., cancerous tissue) removed following use of a compound of Formula (I) or a compound of Formula (II) is used to prepare a pathology section or slide. In some embodiments, cancerous tissue removed following use of a compound of Formula (I) or a compound of Formula (II) is used to prepare a pathology section or slide which is used to diagnose a tissue as malignant or benign.

In some embodiments, targeted delivery of an imaging agent to cancerous breast tissue enables a medical professional to accurately stage cancer enabling medical treatment decisions. In some embodiments, targeted delivery of an imaging agent to cancerous tissue enables a medical professional to observe the size of a tumor (cancerous tissue) or the spread (e.g., metastatic lesions) of cancerous tissue. In some embodiments, targeted delivery of an imaging agent to a cell or tissue enables a medical professional to design an efficacious treatment regimen.

In some embodiments, a selective delivery molecule according to Formula (I) comprising an imaging agent (e.g., a selective delivery molecule labeled with a fluorescence donor-acceptor pair) is employed in guided surgery. In some embodiments, the selective delivery molecule is preferentially localized to cancerous or other pathological tissues with upregulated protease activity (e.g. tissues undergoing inflammatory response). In some embodiments, a selective delivery molecule according to Formula (I) comprising an imaging agent is employed in a guided surgery to remove cancerous tissue, e.g., colorectal cancer. In some embodiments, guided surgery employing the selective delivery molecule allows a surgeon to excise as little healthy (i.e., non-cancerous) tissue as possible. In some embodiments, guided surgery employing the selective delivery molecule allows a surgeon to visualize and excise more cancerous tissue than the surgeon would have been able to excise without the presence of the selective delivery molecule. In some embodiments, the surgery is fluorescence-guided surgery.

In some embodiments, a selective delivery molecule according to Formula (II) comprising an imaging agent (e.g., a selective delivery molecule labeled with a fluorescence donor-acceptor pair) is employed in guided surgery. In some embodiments, the selective delivery molecule is preferentially localized to cancerous or other pathological tissues with upregulated protease activity (e.g. tissues undergoing inflammatory response). In some embodiments, a selective delivery molecule according to Formula (II) comprising an imaging agent is employed in a guided surgery to remove cancerous tissue, e.g., colorectal cancer. In some embodiments, guided surgery employing the selective delivery molecule allows a surgeon to excise as little healthy (i.e., non-cancerous) tissue as possible. In some embodiments, guided surgery employing the selective delivery molecule allows a surgeon to visualize and excise more cancerous tissue than the surgeon would have been able to excise without the presence of the selective delivery molecule. In some embodiments, the surgery is fluorescence-guided surgery.

In some embodiments, a tissue of interest is: breast cancer tissue, colon cancer tissue, squamous cell carcinoma tissue, prostate cancer tissue, melanoma tissue, sarcoma tissue, thyroid cancer tissue, colorectal cancer tissue, skin cancer tissue, ovarian cancer tissue, cancerous lymph node tissue, cervical cancer tissue, lung cancer tissue, pancreatic cancer tissue, head and neck cancer tissue, or esophageal cancer tissue. In some embodiments, the tissue of interest is breast cancer tissue. In some instances, the tissue of interest is colon cancer tissue. In some instances, the tissue of interest is lung cancer tissue. In some cases, the tissue of interest is prostate cancer tissue.

In some embodiments, the cancer is AIDS-related cancers (e.g., AIDS-related lymphoma), anal cancer, basal cell carcinoma, bile duct cancer (e.g., extrahepatic), bladder cancer, bone cancer, (osteosarcoma and malignant fibrous histiocytoma), breast cancer, cervical cancer, colon cancer, colorectal cancer, endometrial cancer (e.g., uterine cancer), ependymoma, esophageal cancer, eye cancer (e.g., intraocular melanoma and retinoblastoma), gastric (stomach) cancer, germ cell tumor, (e.g., extracranial, extragonadal, ovarian), head and neck cancer, leukemia, lip and oral cavity cancer, liver cancer, lung cancer (e.g., small cell lung cancer, non-small cell lung cancer, adenocarcinoma of the lung, and squamous carcinoma of the lung), ovarian cancer, pancreatic cancer, pituitary tumor, prostate cancer, renal cancer, sarcoma, skin cancer, small intestine cancer, squamous cell cancer, testicular cancer, throat cancer, thyroid cancer, urethral cancer, and post-transplant lymphoproliferative disorder (PTLD).

In some embodiments, the cancer is breast cancer. In some instances, the breast cancer comprises invasive ductal carcinoma (IDC), invasive lobular carcinoma (ILC), ductal carcinoma in situ (DCIS), inflammatory breast cancer, lubular carcinoma in situ (LCIS), male breast cancer, molecular subtypes of breast cancer, Paget's disease of the Nipple, phyliodes tumors of the breast, and metastatic breast cancer. In some cases, IDC is further subdivided into tubular carcinoma of the breast, medullary carcinoma of the breast, mucinous carcinoma of the breast, papillary carcinoma of the breast, and cribriform carcinoma of the breast. In some cases, the molecular subtypes of breast cancer comprises luminal A, luminal B, triple-negative/basal-like, HER2-enriched, or normal-like breast cancer.

In some embodiments, the cancer is a lymphoid cancer (e.g., lymphoma).

In some embodiments, the cancer is a B-cell cancer. In some embodiments, the cancer is precursor B-cell cancers (e.g., precursor B-lymphoblastic leukemia/lymphoma) and peripheral B-cell cancers (e.g., B-cell chronic lymphocytic leukemia/prolymphocytic leukemia/small lymphocytic lymphoma (small lymphocytic (SL) NHL), lymphoplasmacytoid lymphoma/immunocytoma, mantel cell lymphoma, follicle center lymphoma, follicular lymphoma (e.g., cytologic grades: I (small cell), II (mixed small and large cell), III (large cell) and/or subtype: diffuse and predominantly small cell type), low grade/follicular non-Hodgkin's lymphoma (NHL), intermediate grade/follicular NHL, marginal zone B-cell lymphoma (e.g., extranodal (e.g., MALT-type+/−monocytoid B cells) and/or Nodal (e.g., +/−monocytoid B cells)), splenic marginal zone lymphoma (e.g., +/−villous lymphocytes), Hairy cell leukemia, plasmacytoma/plasma cell myeloma (e.g., myeloma and multiple myeloma), diffuse large B-cell lymphoma (e.g., primary mediastinal (thymic) B-cell lymphoma), intermediate grade diffuse NHL, Burkitt's lymphoma, High-grade B-cell lymphoma, Burkitt-like, high grade immunoblastic NHL, high grade lymphoblastic NHL, high grade small non-cleaved cell NHL, bulky disease NHL, AIDS-related lymphoma, and Waldenstrom's macroglobulinemia).

In some embodiments, the cancer is a T-cell and/or putative NK-cell cancer. In some embodiments, the cancer is precursor T-cell cancer (precursor T-lymphoblastic lymphoma/leukemia) and peripheral T-cell and NK-cell cancers (e.g., T-cell chronic lymphocytic leukemia/prolymphocytic leukemia, and large granular lymphocyte leukemia (LGL) (e.g., T-cell type and/or NK-cell type), cutaneous T-cell lymphoma (e.g., mycosis fungoides/Sezary syndrome), primary T-cell lymphomas unspecified (e.g., cytological categories (e.g., medium-sized cell, mixed medium and large cell), large cell, lymphoepitheloid cell, subtype hepatosplenic γδ T-cell lymphoma, and subcutaneous panniculitic T-cell lymphoma), angioimmunoblastic T-cell lymphoma (AILD), angiocentric lymphoma, intestinal T-cell lymphoma (e.g., +/−enteropathy associated), adult T-cell lymphoma/leukemia (ATL), anaplastic large cell lymphoma (ALCL) (e.g., CD30+, T- and null-cell types), anaplastic large-cell lymphoma, and Hodgkin's like).

In some embodiments, the cancer is Hodgkin's disease.

In some embodiments, the cancer is leukemia. In some embodiments, the cancer is chronic myelocytic I (granulocytic) leukemia, chronic myelogenous, and chronic lymphocytic leukemia (CLL), acute lymphoblastic leukemia (ALL), acute myeloid leukemia, acute lymphocytic leukemia, and acute myelocytic leukemia (e.g., myeloblastic, promyelocytic, myelomonocytic, monocytic, and erythroleukemia).

In some embodiments, the cancer is a liquid tumor or plasmacytoma. In some embodiments, the cancer is extramedullary plasmacytoma, a solitary myeloma, and multiple myeloma. In some embodiments, the plasmacytoma is multiple myeloma.

In some embodiments, the cancer is lung cancer.

In some embodiments, the cancer is prostate cancer. In some embodiments, the prostate cancer is an adenocarcinoma. In some embodiments, the prostate cancer is a sarcoma, neuroendocrine tumor, small cell cancer, ductal cancer, or a lymphoma. In some embodiments, the prostate cancer is stage A prostate cancer (the cancer cannot be felt during a rectal exam). In some embodiments, the prostate cancer is stage B prostate cancer (i.e., the tumor involves more tissue within the prostate, it can be felt during a rectal exam, or it is found with a biopsy that is done because of a high PSA level). In some embodiments, the prostate cancer is stage C prostate cancer (i.e., the cancer has spread outside the prostate to nearby tissues). In some embodiments, the prostate cancer is stage D prostate cancer. In some embodiments, the prostate cancer is androgen independent prostate cancer (AIPC). In some embodiments, the prostate cancer is androgen dependent prostate cancer. In some embodiments, the prostate cancer is refractory to hormone therapy. In some embodiments, the prostate cancer is substantially refractory to hormone therapy. In some embodiments, the prostate cancer is refractory to chemotherapy. In some embodiments, the prostate cancer is metastatic prostate cancer. In some embodiments, the individual is a human who has a gene, genetic mutation, or polymorphism associated with prostate cancer (e.g., RNASEL/HPC1, ELAC2/HPC2, SR-A/MSR1, CHEK2, BRCA2, PON1, OGG1, MIC-1, TLR4, and PTEN) or has one or more extra copies of a gene associated with prostate cancer. In some embodiments, the prostate cancer is HER2 positive. In some embodiments, the prostate cancer is HER2 negative.

In some embodiments, the cancer has metastasized and is characterized by circulating tumor cells.

In some embodiments, a tissue of interest is a tissue with upregulated protease activity (e.g., a tissue undergoing inflammatory response).

Pharmaceutical Compositions

Disclosed herein, in certain embodiments, are pharmaceutical compositions comprising any of SDMs as disclosed herein. In some embodiments, the pharmaceutical composition comprising an SDM comprises an SDM of any of Formula I or Formula II and a pharmaceutically acceptable carrier.

Pharmaceutical compositions herein are formulated using one or more physiologically acceptable carriers including excipients and auxiliaries which facilitate processing of the active agents into preparations which are used pharmaceutically. Proper formulation is dependent upon the route of administration chosen. A summary of pharmaceutical compositions is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins, 1999).

In certain embodiments, a pharmaceutical composition disclosed herein further comprises a pharmaceutically acceptable diluent(s), excipient(s), or carrier(s). In some embodiments, the pharmaceutical compositions includes other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions also contain other therapeutically valuable substances.

In certain embodiments, a pharmaceutical composition disclosed herein is administered to a subject by any suitable administration route, including but not limited to, parenteral (intravenous, subcutaneous, intraperitoneal, intramuscular, intravascular, intrathecal, intravitreal, infusion, or local) administration.

Formulations suitable for intramuscular, subcutaneous, peritumoral, or intravenous injection include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity is maintained, for example, by the use of a coating such as lecithin, by the maintenance of the required particle size in the case of dispersions, and by the use of surfactants. Formulations suitable for subcutaneous injection also contain optional additives such as preserving, wetting, emulsifying, and dispensing agents.

For intravenous injections, an active agent is optionally formulated in aqueous solutions, preferably in physiologically compatible buffers such as Hank's solution, Ringer's solution, or physiological saline buffer.

Parenteral injections optionally involve bolus injection or continuous infusion. Formulations for injection are optionally presented in unit dosage form, e.g., in ampoules or in multi dose containers, with an added preservative. In some embodiments, the pharmaceutical composition described herein are in a form suitable for parenteral injection as a sterile suspensions, solutions or emulsions in oily or aqueous vehicles, and contain formulatory agents such as suspending, stabilizing and/or dispersing agents. Pharmaceutical formulations for parenteral administration include aqueous solutions of an active agent in water soluble form. Additionally, suspensions are optionally prepared as appropriate oily injection suspensions.

In some embodiments, the pharmaceutical composition described herein is in unit dosage forms suitable for single administration of precise dosages. In unit dosage form, the formulation is divided into unit doses containing appropriate quantities of an active agent disclosed herein. In some embodiments, the unit dosage is in the form of a package containing discrete quantities of the formulation. Non-limiting examples are packaged tablets or capsules, and powders in vials or ampoules. In some embodiments, aqueous suspension compositions are packaged in single-dose non-reclosable containers. Alternatively, multiple-dose reclosable containers are used, in which case it is typical to include a preservative in the composition. By way of example only, formulations for parenteral injection are presented in unit dosage form, which include, but are not limited to ampoules, or in multi dose containers, with an added preservative.

In some embodiments, the amount of a given SDM varies depending upon factors such as the particular compound, the identity (e.g., weight) of the subject, the route of administration, and the duration of that the compound is needed for visualization. Exemplary doses include, but are not limited to, 0.5 mg, 1 mg, 2 mg, 3 mg, 4 mg, 5 mg, 6 mg, 7 mg, 8 mg, 9 mg, 10 mg, 11 mg, 12 mg, 15 mg, 18 mg, 20 mg, 25 mg, or 30 mg. In some cases, the dose of the SDM administered to a subject is 1 mg. In some cases, the dose of the SDM administered to a subject is 2 mg. In some cases, the dose of the SDM administered to a subject is 4 mg. In some cases, the dose of the SDM administered to a subject is 6 mg. In some cases, the dose of the SDM administered to a subject is 8 mg. In some cases, the dose of the SDM administered to a subject is 10 mg. In some cases, the dose of the SDM administered to a subject is 12 mg. In some cases, the dose of the SDM administered to a subject is 15 mg. In some cases, the dose of the SDM administered to a subject is 20 mg. In some cases, the dose of the SDM administered to a subject is 25 mg. In some cases, the dose of the SDM administered to a subject is 30 mg.

In some instances, the SDM is administered from about 30 minutes to about 24 hours prior to surgery. In some instances, the SDM is administered from about 1 hour to about 22 hours, from about 1 hour to about 20 hours, from about 2 hours to about 22 hours, from about 2 hours to about 20 hours, from about 2 hours to about 18 hours, from about 2 hours to about 16 hours, from about 2 hours to about 14 hours, from about 2 hours to about 12 hours, from about 2 hours to about 10 hours, from about 2 hours to about 8 hours, from about 4 hours to about 18 hours, from about 4 hours to about 16 hours, from about 4 hours to about 12 hours, from about 4 hours to about 8 hours, from about 6 hours to about 20 hours, from about 6 hours to about 18 hours, from about 6 hours to about 12 hours, from about 8 hours to about 18 hours, or from about 8 hours to about 12 hours prior to surgery. In some cases, the SDM is administered about 30 minutes, 1 hour, 2 hours, 3 hours, 4 hours, 5 hours, 6 hours, 7 hours, 8 hours, 9 hours, 10 hours, 12 hours, 14 hours, 16 hours, 18 hours, 20 hours, 22 hours, or 24 hours prior to surgery.

In some embodiments, the SDM is administered to a subject via infusion. In some instances, the length of infusion is about 20 minutes, 30 minutes, 40 minutes, 50 minutes, 1 hour, 1.5 hour, 2 hours, 2.5 hours, 3 hours, 4 hours, 5 hours, 6 hours, or more. In some cases, the length of infusion is about 20 minutes. In some cases, the length of infusion is about 30 minutes. In some cases, the length of infusion is about 40 minutes. In some cases, the length of infusion is about 50 minutes. In some cases, the length of infusion is about 1 hour. In some cases, the length of infusion is about 50 minutes. In some cases, the length of infusion is about 1.5 hour. In some cases, the length of infusion is about 50 minutes. In some cases, the length of infusion is about 2 hours. In some cases, the length of infusion is about 50 minutes. In some cases, the length of infusion is about 4 hours. In some cases, the length of infusion is about 50 minutes. In some cases, the length of infusion is about 6 hours.

Fluorescence Detection and Imaging Systems

Any of a variety of fluorescence detection instruments and imaging systems may be used with the imaging agents, e.g., ratiometric fluorescent indicators, imaging methods of the present disclosure. For example, for in vitro studies, conventional spectrofluorometers may be used to perform cell-based assays. For imaging of tissue samples ex vivo, an epifluorescence microscope equipped with an appropriate set of excitation and emission filters and one or more CCD cameras may be utilized. For in vivo imaging applications, more sophisticated imaging systems may be employed. In specialized in vivo imaging applications, e.g., colonoscopy, a modified endoscope that allows fluorescence images to be collected at two (or more) emission wavelengths may be employed.

In general, these fluorescence detection and imaging systems will comprise: (i) one or more excitation light sources, (ii) sets of excitation and emission filters (or other components for adjusting wavelength settings and bandpass), (iii) one or more detectors, and (iv) other optical components for manipulating the path of light beams as they traverse the optical system. In some instances, the fluorescence detection and imaging systems further comprise one or more processors, computer data storage (memory) components, operating system software, instrument control software (e.g., image acquisition software), and/or data processing and display software (e.g., image processing and display software).

Figure 5:
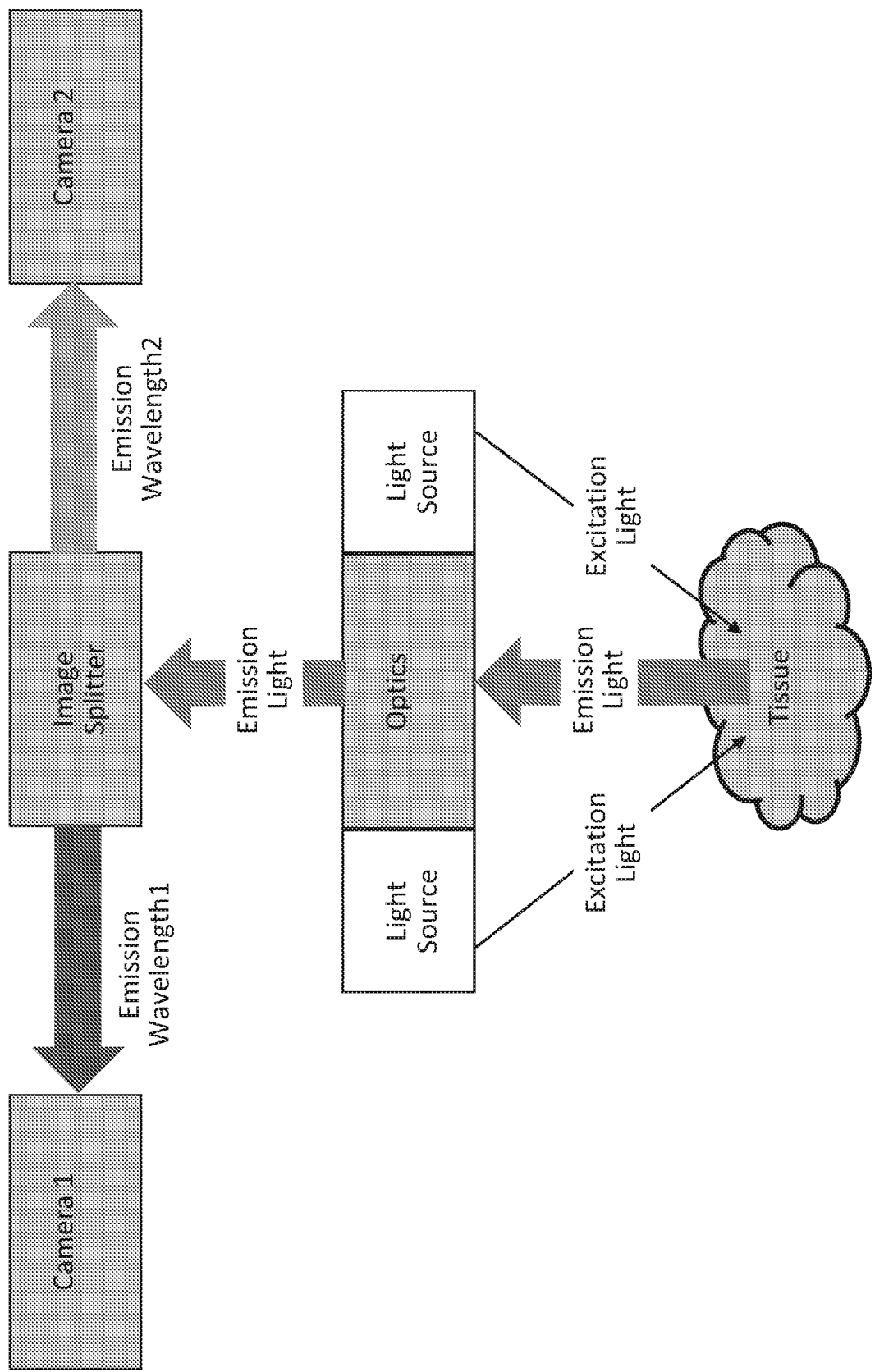
FIG. 5 schematically illustrates one non-limiting example of a ratiometric fluorescence imaging system that utilizes an image splitter to image the fluorescence emission at two different wavelengths onto two different cameras.

FIG. 5 schematically illustrates one non-limiting example of a ratiometric fluorescence imaging system that utilizes an image splitter optical component (e.g., a dichroic reflector) to image the fluorescence emission at two different wavelengths onto two different cameras. Excitation light provided, for example, by a ring light surrounding a microscope objective, is used to illuminate a tissue sample at a specified excitation wavelength. Emitted fluorescence is collected by the optical imaging system, directed to the image splitter component where the image is separated into two component images according to the emission wavelength cutoff of the image splitter, and separately imaged onto the image sensor chips of the two different cameras. In some embodiments, the two images are captured simultaneously. In some embodiments, the two images are captured sequentially.

Any of a variety of light sources known to those of skill in the art may be used as an excitation light source including, but not limited to, arc lamps, tungsten-halogen lamps, lasers (e.g., argon ion lasers, helium-neon (HeNe) lasers, etc.), diode lasers, light emitting diodes (LEDs), light engines, and the like, or any combination thereof. In some instances, the fluorescence detection or imaging system comprises at least one light source, at least two light sources, at least three light sources, at least four light sources, at least five light sources, or more.

Excitation and emission filter sets comprise any of a variety of optical filters known to those of skill in the art including, but not limited to, optical glass filters (e.g., Schott optical filters), long-pass filters, short-pass filters, interference filters, dichroic reflectors, notch filters, and the like, or any combination thereof. In some instances, the excitation and/or emission wavelengths (or bandpass) are set and/or adjusted by changing one or more optical filters in the optical path of the system. In some embodiments, the excitation and/or emission wavelengths (and bandpass) are set and/or adjusted using other components such as diffraction gratings, monochromators, acousto-optic modulators, tunable liquid-crystal filters, and the like.

In some instances, excitation or emission wavelength settings for the fluorescence detection or imaging system are independently adjusted and range from about 350 nm to about 900 nm. In some instances, the excitation or emission wavelength are set at about 350 nm, 375 nm, 400 nm, 425 nm, 450 nm, 475 nm, 500 nm, 525 nm, 550 m, 575 nm, 600 nm, 625 nm, 650 nm, 675 nm, 700 nm, 725 nm, 750 nm, 775 nm, 800 nm, 825 nm, 850 nm, 875 nm, or 900 nm. Those of skill in the art will recognize that the excitation or emission wavelengths may be set to any value within this range, e.g., about 620 nm.

In some instances, the bandwidths of the excitation and emission light are independently adjusted and are specified as the specified excitation or emission wavelength ±2 nm, ±5 nm, ±10 nm, ±20 nm, ±40 nm, ±80 nm, or greater. Those of skill in the art will recognize that the excitation or emission bandwidths may be set to any value within this range, e.g., about ±55 nm.

Any of a variety of detectors and image sensors known to those of skill in the art may be used including, but not limited to, photodiodes, avalanche photodiodes, photodiode arrays, photomultipliers, CCD or CMOS image sensors and cameras, and the like, or any combination thereof. In some instances, the fluorescence detection or imaging system comprises at least one detector, at least two detectors (e.g., for simultaneous capture of fluorescence images at two different emission wavelengths), at least three detectors, at least four detectors, at least five detectors, or more. In some optical designs, the fluorescence detection or imaging system is configured to capture fluorescence intensity images at two (or more) different emission wavelengths sequentially, e.g., by changing the fluorescence emission filter between image capture steps. In some optical designs, the fluorescence detection or imaging system is configured to collect fluorescence intensity images at two (or more) different emission wavelengths simultaneously, e.g., by including appropriate dichroic reflectors in the emission light optical path and utilizing a different detector for each emission wavelength.

Examples of other optical components that may be utilized in fluorescence detection and imaging systems include, but are not limited to, lenses or lens systems, prisms, beam-splitters, mirrors, optical fibers, diffractive optical elements for correction of chromatic aberration, etc. These components are configured, along with light sources, excitation and emission filters (or other components for adjusting wavelength settings and bandpass), and detectors, in any of a number of optical arrangements known to those of skill in the art.

Image Processing Algorithms

Also disclosed herein are image processing algorithms for use with ratiometric fluorescence imaging methods to improve the accuracy of detecting and visualizing areas of biological activity within imaged biological specimens. The disclosed algorithms for generating and displaying fluorescence ratio images and regions-of-interest (ROI) therein enable automated, semi-automated, or manual identification of ROI corresponding to the areas within the biological specimen that exhibit a specific biological activity or structure of interest. In some examples, ROIs are generated from fluorescence ratio images. In some examples ROIs are generated from a combination of fluorescence ratio images and/or fluorescence intensity images.

Figure 6:
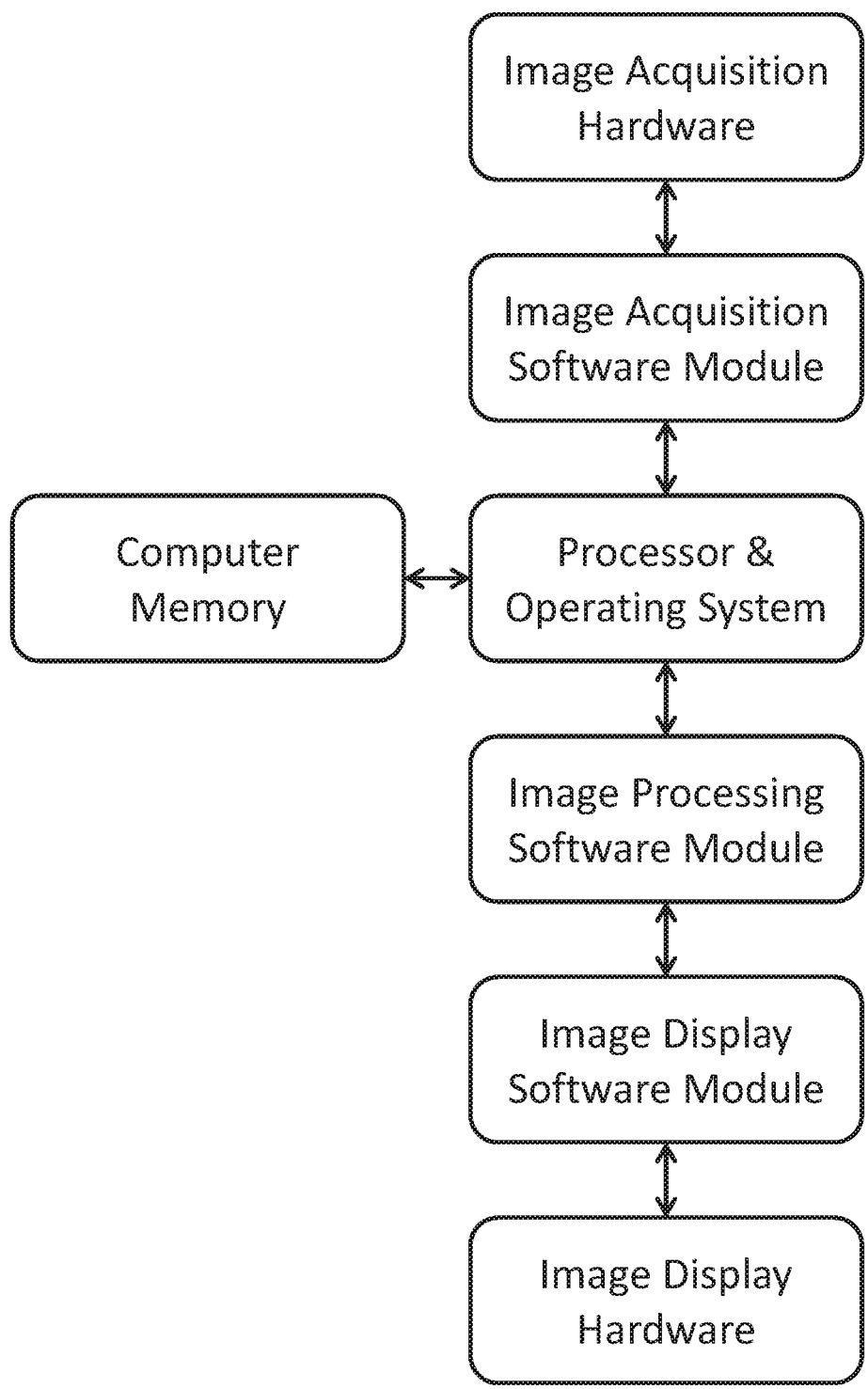
FIG. 6 provides a schematic illustration of ratiometric imaging system comprising hardware (e.g., image acquisition hardware, a processor, and computer memory) and software components (e.g., an operating system, and image acquisition, image processing, and image display software modules).

FIG. 6 provides a schematic illustration of a fluorescence imaging system comprising both hardware components and software components. As described above, in some instances the hardware components of the system comprises image acquisition hardware (e.g., light sources, excitation and emission filters or equivalents, and detectors, as described above), as well as one or more processors, computer storage (memory) components, image display components, other instrument control modules (e.g., temperature controllers) and/or communication hardware. In some instances, the software components of the system comprises an operating system within which the programmed instructions for one or more image acquisition, image processing, and/or image display software modules, as well as other optional instrument control and communications software modules, are executed.

As noted above, in some embodiments of the disclosed ratiometric fluorescence imaging methods, one or more image processing algorithms, which are encoded within the instruction set of an image processing software module, are used to enable automated, semi-automated, or manual identification of ROI within the images being analyzed which correspond to the areas within the biological specimen that exhibit a specific biological activity or structure of interest.

Figure 7:
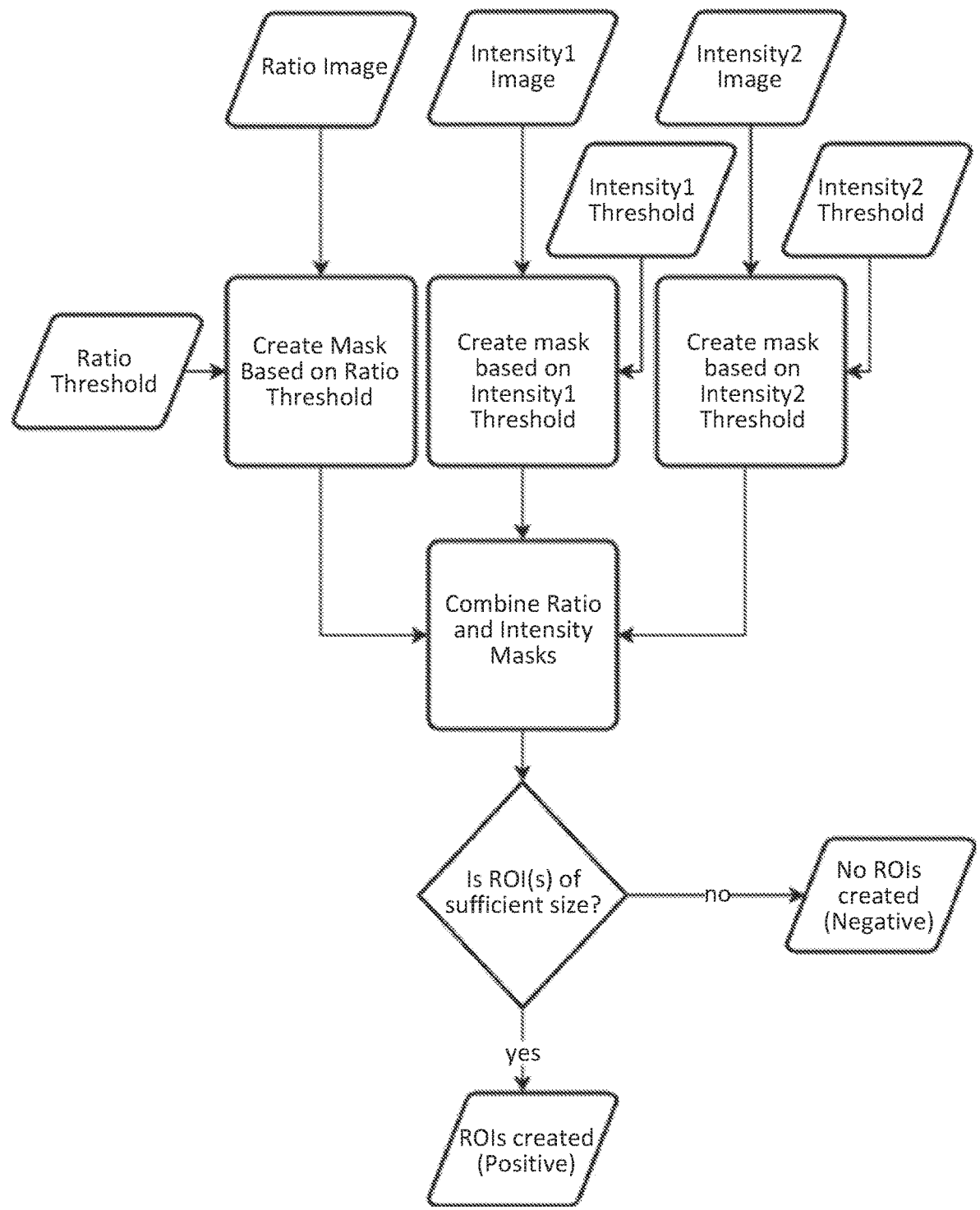
FIG. 7 illustrates an image processing algorithm used to identify regions of interest (ROI) that exhibit high fluorescence ratio and/or fluorescence intensity values within a fluorescence ratio image.

FIG. 7 illustrates an image processing algorithm used to identify regions of interest (ROI) that exhibit high fluorescence ratio and/or fluorescence intensity values within a fluorescence ratio image and/or the corresponding fluorescence intensity images. Fluorescence intensity images at two different emission wavelengths (Intensity 1 and Intensity 2) are used to calculate a fluorescence ratio image. In some instances, the intensity images are background subtracted and/or normalized to the exposure times used to capture the images prior to calculating the ratio. For each of the fluorescence ratio and fluorescence intensity images, threshold values of ratio or intensity are used to generate a mask image (i.e., a corresponding binary image file where each pixel for which the original image had a ratio or intensity value equal to or below the threshold is set to a value of 0, and where each pixel for which the original image had a ratio or intensity value greater than the threshold is set to a value of 1). ROI are detected by performing a logical AND operation to combine the three mask images. In some embodiments, the resulting ROI are optionally evaluated to ensure that they meet a minimum size requirement (i.e., to eliminate single pixel noise or other detection artifacts so as to ensure that they are of biological relevance). The minimum ROI setting is related to the optical resolution of the imaging system, and is selected to exceed the resolution of the imaging system to avoid identifying false positives. In some embodiments, the algorithm is performed in a fully automated fashion. In some embodiments, it is performed in a semi-automated fashion. In some embodiments, it is performed in a manual fashion. In some instances, measurement of the mean value for fluorescence ratio and/or fluorescence intensity within the ROI provides a qualitative measure of biological activity. In some instances, measurement of the mean value for fluorescence ratio and/or fluorescence intensity within the ROI provides a quantitative measure of biological activity.

Figure 10:
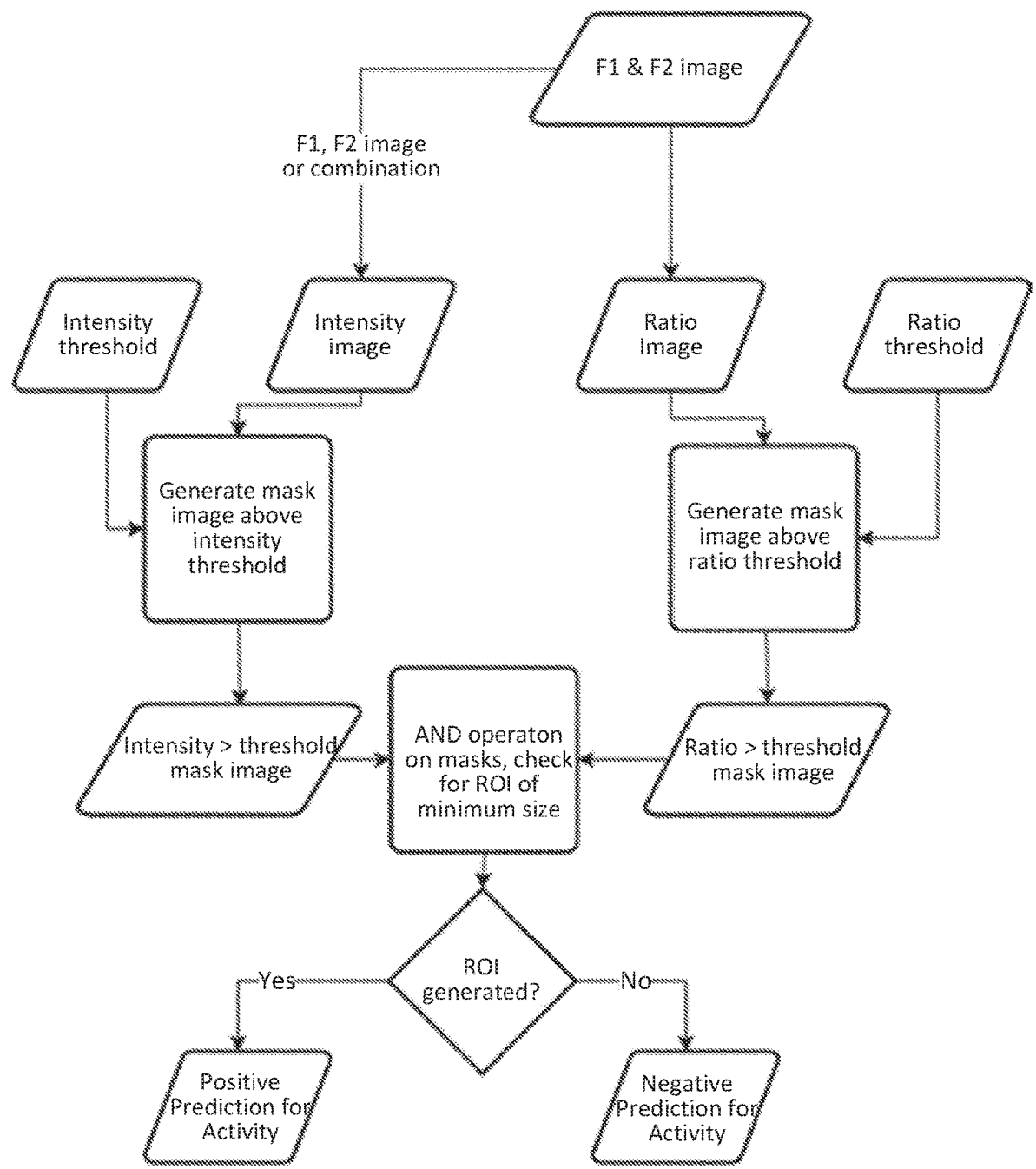
FIG. 10 illustrates an image processing algorithm used to identify regions of interest (ROI) and provide a prediction of biological activity (e.g., enhanced enzyme activity) in biological specimens that have been infused with a ratiometric fluorescence indicator, e.g., SDM-25. A prediction of positive or negative score is generated for a given combination of fluorescence intensity ratio threshold (e.g., a Cy5/Cy7 fluorescence intensity ratio threshold) and/or a fluorescence intensity threshold (e.g., a Cy5 fluorescence intensity threshold).

FIG. 10 illustrates an image processing algorithm used to (i) identify regions of interest (ROI) that exhibit high fluorescence ratio and/or fluorescence intensity values within a fluorescence ratio image and/or the corresponding fluorescence intensity images, and (ii) make a positive or negative prediction for the biological activity indicated by the ratiometric fluorescent indicator used in preparing the images. Fluorescence intensity images at two different emission wavelengths (F1 and F2) are used to calculate a fluorescence ratio image. In some instances, the intensity images are background subtracted and/or normalized to the exposure times used to capture the images prior to calculating the ratio. In some instances, the fluorescence ratio image is used for detection of ROI. In some instances, the fluorescence ratio image and one of the two fluorescence intensity images are used for the detection of ROI. In some instances, the fluorescence ratio image and both of the fluorescence intensity images are used for the detection of ROI. For each of the fluorescence ratio and/or fluorescence intensity images selected, threshold value(s) of ratio and/or intensity are used to generate a mask image (i.e., a corresponding binary image file where each pixel for which the original image had a ratio or intensity value equal to or below the threshold is set to a value of 0, and where each pixel for which the original image had a ratio or intensity value greater than the threshold is set to a value of 1). In instances where both the fluorescence ratio image and at least one fluorescence intensity image are used, ROI are detected by performing a logical AND operation to combine the two or more mask images. In some embodiments, the resulting ROI are optionally evaluated to ensure that they meet a minimum size requirement (i.e., to eliminate single pixel noise or other detection artifacts so as to ensure that they are of biological relevance). The minimum ROI setting is related to the optical resolution of the imaging system, and is selected to exceed the resolution of the imaging system to avoid identifying false positives. The presence of validated ROI is used to make a positive prediction for the specified biological activity within the biological specimen under study. In some embodiments, the algorithm is performed in a fully automated fashion. In some embodiments, it is performed in a semi-automated fashion. In some embodiments, it is performed in a manual fashion. In some instances, measurement of the mean value for fluorescence ratio and/or fluorescence intensities within the ROI provides a qualitative measure of biological activity. In some instances, measurement of the mean value for fluorescence ratio and/or fluorescence intensities within the ROI provides a quantitative measure of biological activity.

Figure 11:
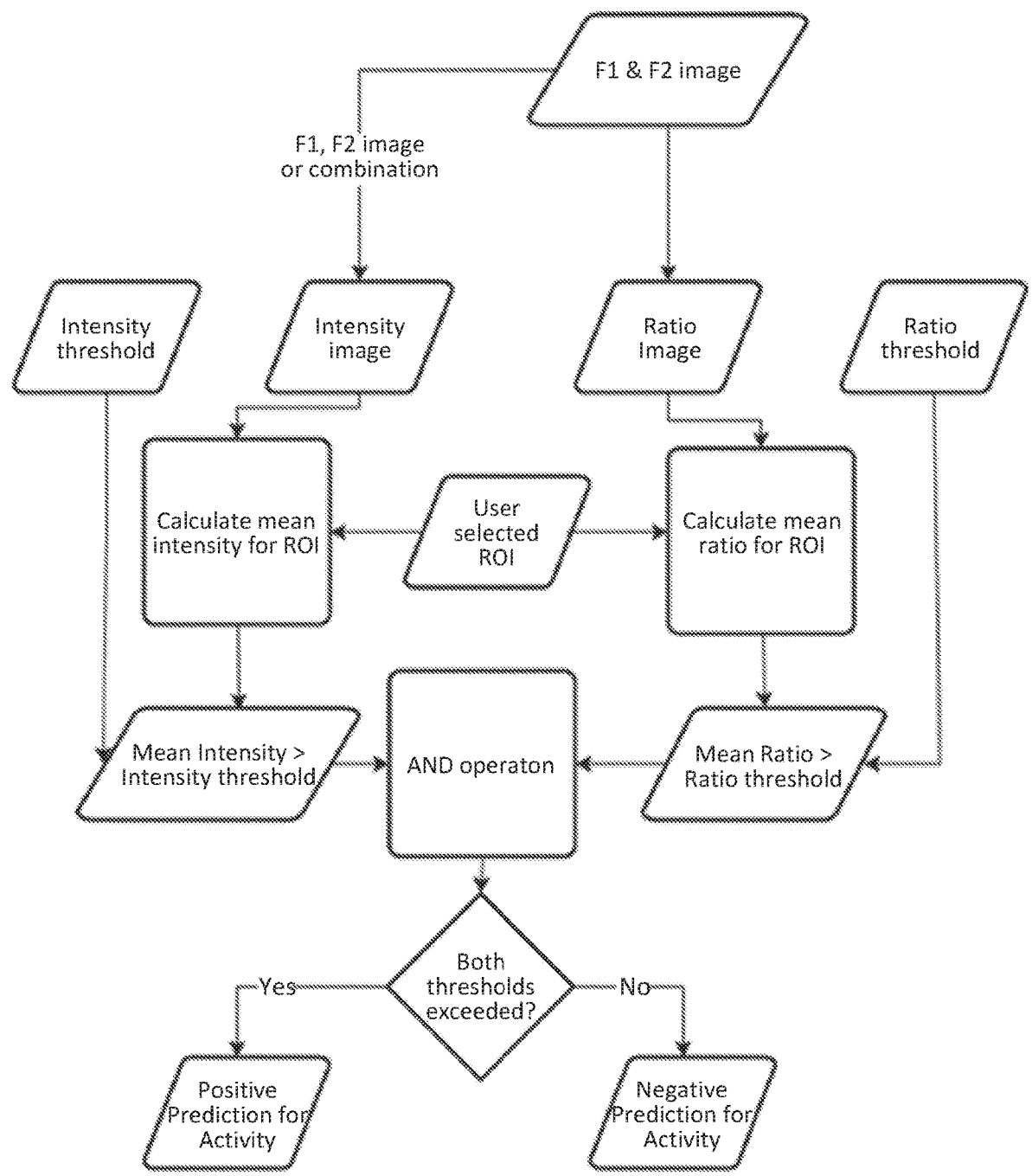
FIG. 11 illustrates an image processing algorithm used to determine a positive or negative prediction of biological activity (e.g., enhanced enzyme activity) in biological specimens that have been infused with a ratiometric fluorescence indicator, e.g., SDM-25. A determination of positive or negative activity is generated for a given combination of fluorescence ratio threshold (e.g., a Cy5/Cy7 fluorescence ratio threshold) and/or a fluorescence intensity threshold (e.g., a Cy5 fluorescence intensity threshold).

FIG. 11 illustrates an image processing algorithm wherein user-selected ROI are used to make a positive or negative prediction for the biological activity indicated by the ratiometric fluorescent indicator used in preparing the images. Fluorescence intensity images at two different emission wavelengths (F1 and F2) are used to calculate a fluorescence ratio image. In some instances, the intensity images are background subtracted and/or normalized to the exposure times used to capture the images prior to calculating the ratio. In some instances, the fluorescence ratio image is used for identifying user-selected ROI. In some instances, the fluorescence ratio image and one of the two fluorescence intensity images are used for identifying user-selected ROI. In some instances, the fluorescence ratio image and both of the fluorescence intensity images are used for identifying user-selected ROI. For each of the fluorescence ratio and/or fluorescence intensity images for which user-selected ROI are identified, the mean values of ratio and/or intensity values within the user-selected ROI are calculated and compared to fluorescence ratio and/or intensity threshold(s) to generate a mask image (i.e., a corresponding binary image file where each pixel for which the original image had a ratio or intensity value equal to or below the threshold is set to a value of 0, and where each pixel for which the original image had a ratio or intensity value greater than the threshold is set to a value of 1). In the case that two or more mask images are generated, the mask images are then combined by performing a logical AND operation to identify those ROI for which all thresholds have been exceeded. In some instances, the resulting ROI are optionally evaluated to ensure that they meet a minimum size requirement (i.e., to eliminate single pixel noise or other detection artifacts so as to ensure that they are of biological relevance). The minimum ROI setting is related to the optical resolution of the imaging system, and is selected to exceed the resolution of the imaging system to avoid identifying false positives. The presence of validated ROI is used to make a positive prediction for the specified biological activity within the biological specimen under study. In some embodiments, the algorithm is performed in a fully automated fashion. In some embodiments, it is performed in a semi-automated fashion. In some embodiments, it is performed in a manual fashion.

In some instances, measurement of the mean value for fluorescence ratio and/or fluorescence intensities within the ROI provides a qualitative measure of biological activity. In some instances, measurement of the mean value for fluorescence ratio and/or fluorescence intensities within the ROI provides a quantitative measure of biological activity.

Figure 12:
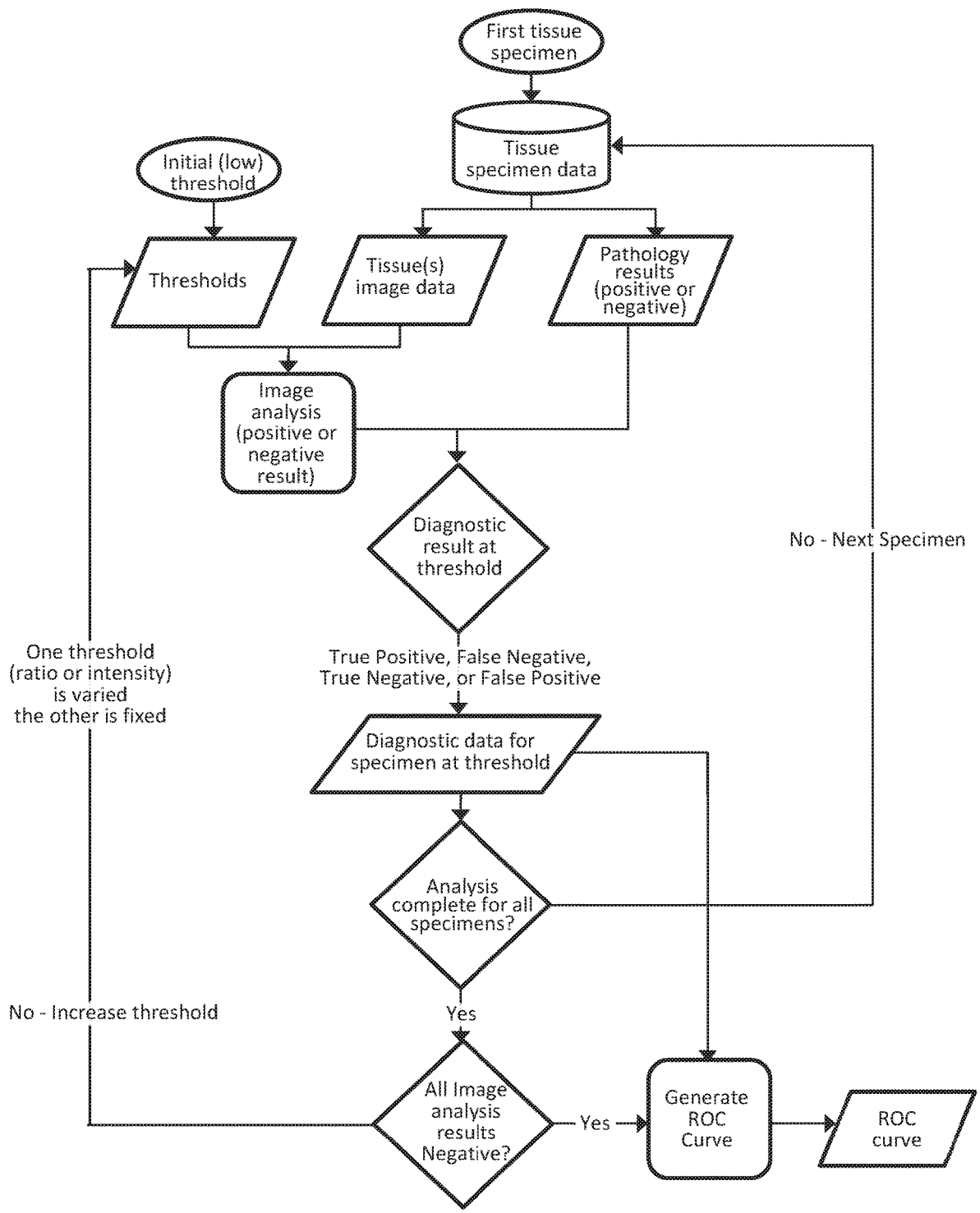
FIG. 12 illustrates one non-limiting example of an image processing algorithm used to identify the most accurate combination of fluorescence ratio and/or intensity thresholds for determining the presence of biological activity (e.g., enhanced enzyme activity) in biological specimens that have been infused with a ratiometric fluorescence indicator, e.g., SDM-25. In this example, one threshold (i.e., a fluorescence ratio threshold or a fluorescence intensity threshold) is varied while the other is held fixed to generate the most accurate threshold based on a comparison of the imaging data to pathology lab data (or other independent determinations of biological activity) for a set of biological specimens. The receiver operator characteristic (ROC) curve is generated by comparing the predictions from image analysis at different fluorescence ratio and/or intensity thresholds to, for example, the pathology lab results.

FIG. 12 illustrates one non-limiting example of an image processing algorithm used to identify the most accurate combination of fluorescence ratio and/or intensity thresholds for determining the presence of biological activity (e.g., enhanced extracellular enzyme activity correlated with cancer) in biological specimens that have been infused with a ratiometric fluorescence indicator. Fluorescence intensity images at two different emission wavelengths are used to calculate a fluorescence ratio image for each of a plurality of biological specimens, i.e., tissue specimens that have been infused with a ratiometric fluorescent indicator. In some instances, the intensity images are background subtracted and/or normalized to the exposure times used to capture the images prior to calculating the ratio. A starting value is provided for a first fluorescence intensity threshold, a second fluorescence intensity threshold, a fluorescence ratio threshold, or any combination thereof; and for each of the biological specimens, the steps of: i) processing the fluorescence ratio image, the first fluorescence intensity image, the second fluorescence intensity image, or any combination thereof, using an image analysis algorithm (e.g., the algorithms illustrated in FIG. 7, FIG. 10, or FIG. 11), wherein the image analysis algorithm uses the fluorescence ratio threshold, the first fluorescence intensity threshold, the fluorescence intensity threshold, or any combination thereof, to create mask images of the fluorescence ratio image and the fluorescence intensity image(s), performs an AND logical operation on the mask images if two or more mask images have been created, optionally checks that any detected regions of interest that exhibit a fluorescence ratio or intensity value that exceeds the specified fluorescence ratio or intensity threshold(s) are greater than a specified minimum size, and provides a classification of the biological specimen as positive or negative for the specified biological activity (e.g., cancer); ii) comparing the classification provided by the image analysis algorithm with a pathology lab test result for the biological specimen to determine whether the classification is a true positive, false negative, true negative, or false positive; and iii) storing the true positive, false negative, true negative, or false positive result are repeated. These steps are then repeated using an increased value of the first fluorescence intensity threshold, the second fluorescence intensity threshold, or the fluorescence ratio threshold while the other thresholds are held fixed until all of the biological specimens are classified as negative by the image processing algorithm. Receiver operator characteristic (ROC) curves plot clinical sensitivity (or "true positive rate") versus (1–clinical specificity) (or "false positive rate"), and are routinely used to determine the sensitivity and specificity of diagnostic tests. A receiver operator characteristic (ROC) curve is calculated using the stored classification results for each set of fluorescence ratio and intensity threshold values; and the area under the ROC curve is compared for each set of fluorescence ratio and intensity threshold values to determine an optimal setting for the values of the fluorescence ratio threshold, the first fluorescence intensity threshold, the second fluorescence intensity threshold, or any combination thereof.

One threshold (i.e., a fluorescence ratio threshold or a fluorescence intensity threshold) is varied at a time while the other(s) are held fixed to generate the most accurate threshold based on the comparison of the imaging data to pathology lab data (or other independent determinations of biological activity) for a set of biological specimens. The receiver operator characteristic (ROC) curve is generated by comparing the predictions from image analysis at different fluorescence ratio and/or intensity thresholds to, for example, the pathology lab results.

In some embodiments, the threshold optimization algorithm is performed in a fully automated fashion. In some embodiments, it is performed in a semi-automated fashion. In some embodiments, it is performed in a manual fashion.

The algorithms described herein are used, individually or in combination, to improve the clinical (or non-clinical) sensitivity (or "true positive rate"), specificity (or "true negative rate"), and overall predictive accuracy of the disclosed ratiometric imaging methods for detecting biological activities of interest using ratiometric fluorescent indicators. In some instances, the sensitivity is at least 20%, at least 30%, at least 40%, at least 50%, at least 60%, at least 70%, at least 80%, at least 90%, at least 95%, or 100%. In some instances, the specificity is at least 20%, at least 30%, at least 40%, at least 50%, at least 60%, at least 70%, at least 80%, at least 90%, at least 95%, or 100%. Those of skill in the art will recognize that the sensitivity and specificity may each individually have any value within these ranges, for example, the sensitivity may be 92% and the specificity may be 94%. In some instances, the sensitivity and/or specificity is dependent on the type of biological activity (or correlated disease state) to be detected. For example, the sensitivity and/or sensitivity may vary depending on a particular type of cancer that is being detected.

In the examples described below, the image processing algorithms disclosed herein have been implemented using the open source ImageJ software developed by the National Institutes of Health, but as will be recognized by those of skill in the art, they may also be implemented using any of a variety of other programming languages (e.g., including, but not limited to C, C++, Java, Fortran, Lua, Visual Basic, and the like) and software packages (e.g., including, but not limited to Cell Profiler, Icy, LabVIEW, MatLab (Mathworks, Natick, Mass.), and the like). In some embodiments, the image processing algorithms disclosed herein may potentially be implemented using custom software code that facilitates the performance of the algorithms such that they run faster, use less computer memory, run on inexpensive processors, etc.

Computer Systems

One or more processors are used to implement the image processing methods and algorithms disclosed herein. The one or more processors may comprise a hardware processor such as a central processing unit (CPU), a graphic processing unit (GPU), a general-purpose processing unit, or computing platform. The one or more processors may be comprised of any of a variety of suitable integrated circuits, microprocessors, logic devices and the like. Although the disclosure is described with reference to a processor, other types of integrated circuits and logic devices may also be applicable. The processor may have any suitable data operation capability. For example, the processor may perform 512 bit, 256 bit, 128 bit, 64 bit, 32 bit, or 16 bit data operations. The one or more processors may be single core or multi core processors, or a plurality of processors configured for parallel processing.

The one or more processors, or the fluorescence imaging system itself, may be part of a larger computer system and/or may be operatively coupled to a computer network (a "network") with the aid of a communication interface to facilitate transmission of and sharing of image data and predictive results. The network may be a local area network, an intranet and/or extranet, an intranet and/or extranet that is in communication with the Internet, or the Internet. The network in some cases is a telecommunication and/or data network. The network may include one or more computer servers, which in some cases enables distributed computing, such as cloud computing. The network, in some cases with the aid of the computer system, may implement a peer-to-peer network, which may enable devices coupled to the computer system to behave as a client or a server.

The computer system may also include memory or memory locations (e.g., random-access memory, read-only memory, flash memory), electronic storage units (e.g., hard disks), communication interfaces (e.g., network adapters) for communicating with one or more other systems, and peripheral devices, such as cache, other memory, data storage and/or electronic display adapters. The memory, storage units, interfaces and peripheral devices may be in communication with the one or more processors, e.g., a CPU, through a communication bus, e.g., as is found on a motherboard. The storage unit(s) may be data storage unit(s) (or data repositories) for storing data.

The one or more processors, e.g., a CPU, execute a sequence of machine-readable instructions, which are embodied in a program (or software). The instructions are stored in a memory location. The instructions are directed to the CPU, which subsequently program or otherwise configure the CPU to implement the methods of the present disclosure. Examples of operations performed by the CPU include fetch, decode, execute, and write back. The CPU may be part of a circuit, such as an integrated circuit. One or more other components of the system may be included in the circuit. In some cases, the circuit is an application specific integrated circuit (ASIC).

The storage unit stores files, such as drivers, libraries and saved programs. The storage unit stores user data, e.g., user-specified preferences and user-specified programs. The computer system in some cases may include one or more additional data storage units that are external to the computer system, such as located on a remote server that is in communication with the computer system through an intranet or the Internet.

Some aspects of the image processing methods provided herein, such as the disclosed image processing algorithms, are implemented by way of machine (e.g., processor) executable code stored in an electronic storage location of the computer system, such as, for example, in the memory or electronic storage unit. The machine executable or machine readable code is provided in the form of software. During use, the code is executed by the one or more processors. In some cases, the code is retrieved from the storage unit and stored in the memory for ready access by the one or more processors. In some situations, the electronic storage unit is precluded, and machine-executable instructions are stored in memory. The code may be pre-compiled and configured for use with a machine having one or more processors adapted to execute the code, or may be compiled at run time. The code may be supplied in a programming language that is selected to enable the code to execute in a pre-compiled or as-compiled fashion.

Various aspects of the technology may be thought of as "products" or "articles of manufacture" typically in the form of machine (or processor) executable code and/or associated data that is stored in a type of machine readable medium. Machine-executable code is stored in an electronic storage unit, such as memory (e.g., read-only memory, random-access memory, flash memory) or on a hard disk. "Storage" type media include any or all of the tangible memory of the computers, processors or the like, or associated modules thereof, such as various semiconductor memory chips, tape drives, disk drives and the like, which may provide non-transitory storage at any time for the software that encodes the image processing methods and algorithms disclosed herein.

All or a portion of the software code may at times be communicated through the Internet or various other telecommunication networks. Such communications, for example, enable loading of the software from one computer or processor into another, for example, from a management server or host computer into the computer platform of an application server. Thus, other types of media that are used to convey the software encoded instructions include optical, electrical and electromagnetic waves, such as those used across physical interfaces between local devices, through wired and optical landline networks, and over various atmospheric links. The physical elements that carry such waves, such as wired or wireless links, optical links or the like, are also considered media that convey the software encoded instructions for performing the methods disclosed herein. As used herein, unless restricted to non-transitory, tangible "storage" media, terms such as computer or machine "readable medium" refer to any medium that participates in providing instructions to a processor for execution.

The computer system typically includes, or may be in communication with, an electronic display for providing, for example, images captured by the imaging device. The display is typically also be capable of providing a user interface. Examples of UI's include, but are not limited to, graphical user interfaces (GUIs), web-based user interfaces, and the like.

EXAMPLES

These examples are provided for illustrative purposes only and not to limit the scope of the claims provided herein.

Example 1—Ratiometric Imaging in Humans

Study Design:

Ratiometric imaging was performed as part of a Phase 1, open-label, dose-escalation study in women with primary, non-recurrent breast cancer undergoing surgery. The study included 5 dose cohorts for the dose escalation phase using a 3+3 cohort expansion design starting at a dose of 1 mg, followed by a $6^{th}$ additional cohort based on the characteristics of fluorescence and safety data observed in each of the dose groups. The additional cohort compared fluorescence characteristics at different SDM-25 (AVB-620) administration times before surgery and imaging. Patients received an infusion of SDM-25 from 2 to 20 hours prior to undergoing lumpectomy/mastectomy and sentinel node biopsy/axillary dissection procedures. Imaging analysis was performed on images obtained of the surgical field as well as post-excision surgical specimens which included exposed primary tumor. Pathology reports were obtained in order to correlate imaging results with histopathologic data. SDM-25 was administered via intravenous (IV) infusion, followed by a normal saline flush. Subjects enrolled into cohorts 1 to 4 received intraperitoneal (IP) injections 12 to 20 hours before the surgical procedure (previous day). Subject in the expansion cohort received SDM-25 either 2 to 12 hours (same day) or 12 to 20 hours (previous day) before the surgical procedure.

Image Capture:

The imaging system was provided by the study sponsor and utilized a three-camera system that simultaneously records three spatially registered images. The first is a color camera and the other two cameras are used to image fluorescence. The imaging system displays four real-time images: a color bright field image, a Cy5 dye fluorescence image, a Cy7 dye fluorescence image, and a Cy5/Cy7 ratio-image generated from the two fluorescence images. Background images (with excitation light turned off) were taken prior to specimen imaging. Image exposure time varied with dose and was adjusted to fill the dynamic range of the camera sensors. In vivo images were obtained of the initial surgical field, the residual tumor bed, and the axillary contents. Following surgical excision, a number of images were collected of the primary tumor, margin specimens and all lymph nodes from multiple angles.

Image Analysis:

Stored images of excised tissue were analyzed after surgery. Cy5 and Cy7 images were background subtracted and were used to generate Cy5/Cy7 ratio images. Tumor regions (i.e., regions of interest (ROI)) were identified as areas exhibiting high fluorescence ratios. ROI were drawn so that only the area of the image containing the tissue of interest was analyzed. For quantification and comparison across cohorts, fluorescence intensity readings were normalized by exposure length. The exposure corrected fluorescence intensity values from the ROI were used to generate a final ROI ratio image.

ROIs are generated automatically based on user-defined thresholds as shown in FIG. 7. Alternatively, users manually select the ROI based on Cy5/Cy7 fluorescence ratio and/or intensities.

Pathological Analysis of Human Tissue Samples:

Pathology departments at the different study sites examined surgically-excised tissue according to local departmental protocols. Data was collected on the tumor size, grade, nodal status, including histologic classification (e.g., invasive ductal, invasive lobular, ductal carcinoma, etc.), as well as on estrogen receptor (ER), progesterone receptor (PR) and HER2 receptor status. Imaging and pathologic correlation was performed by matching data from the final pathology report to the results derived from the image analysis described above.

Figure 8A:
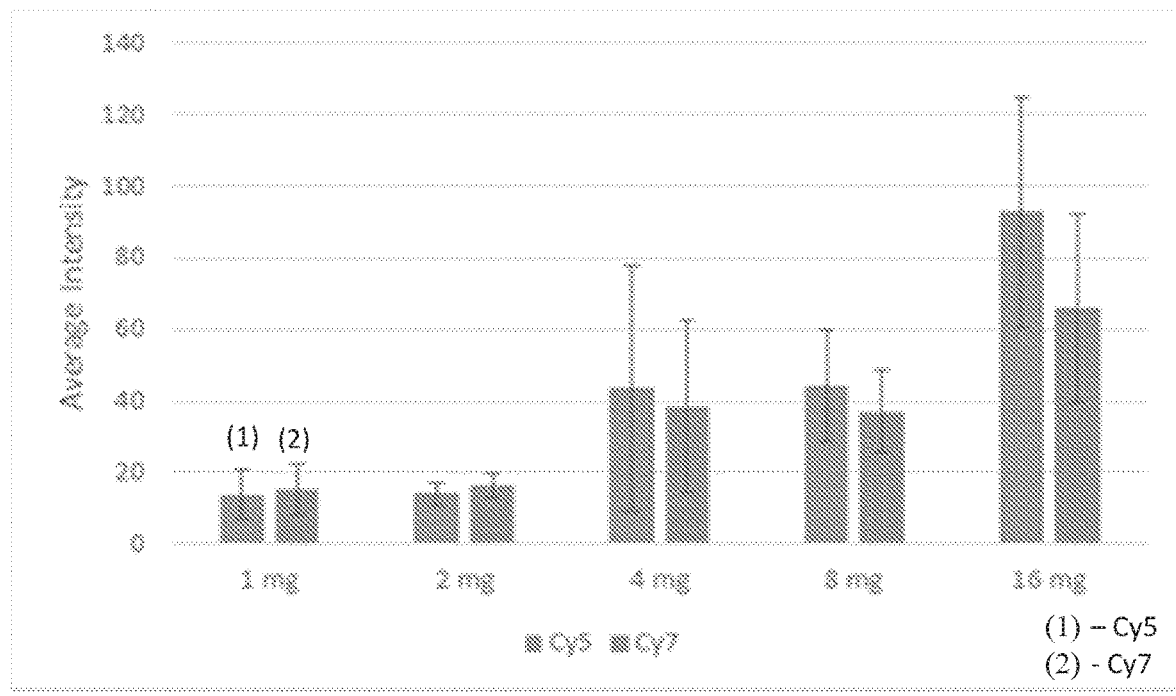
FIG. 8A-FIG. 8B show examples of fluorescence intensity data for images of biological specimens from a human dose escalation study that have been infused with SDM-25 (also referred to as AVB-620).
Figure 8B:
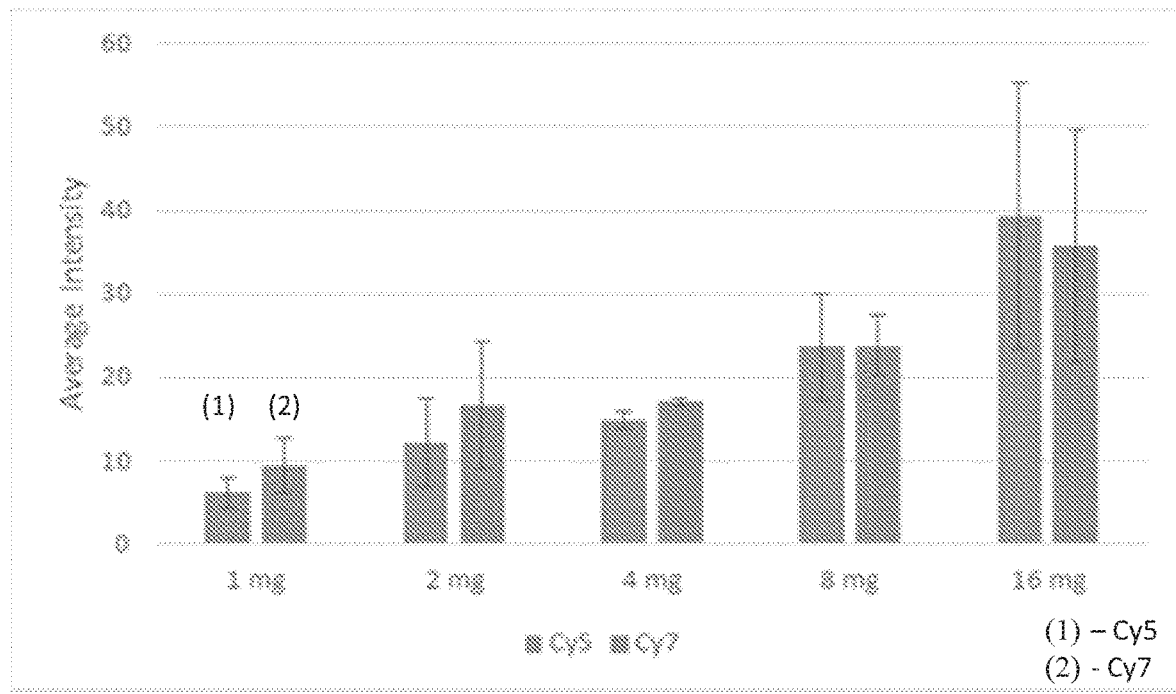
Figure 9:
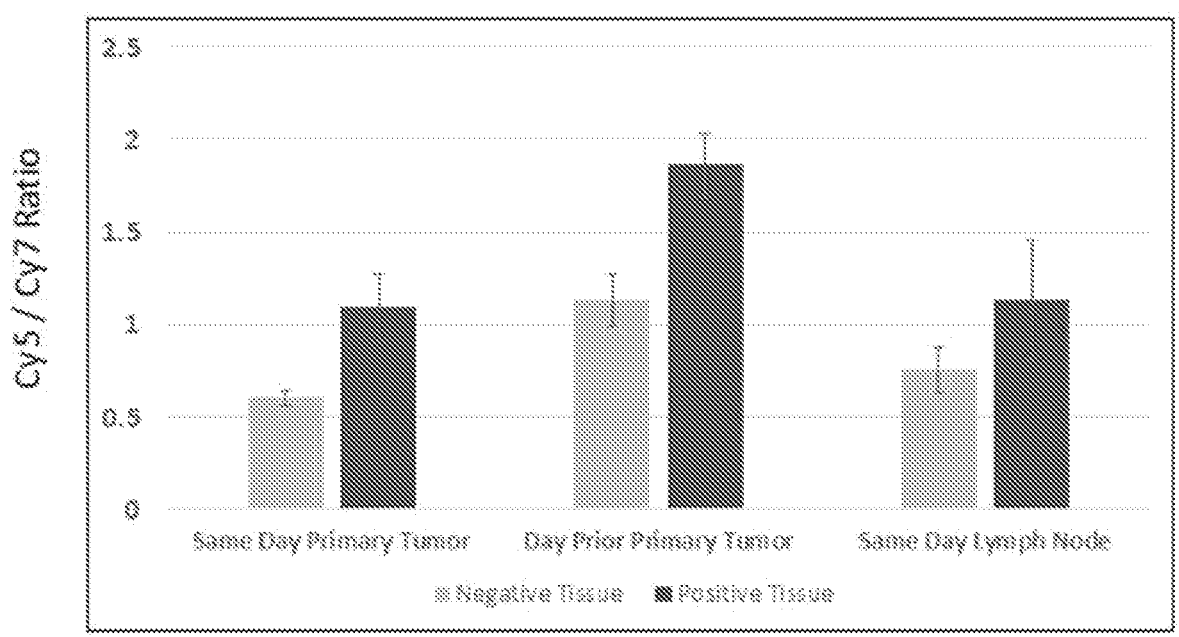
FIG. 9 shows examples of data that indicate that ratiometric fluorescence imaging using SDM-25 can differentiate between malignant (positive) and non-malignant (negative) tissue in breast cancer patients. Data from primary tumor and lymph nodes is provided. The error bars indicate standard deviations.

Results:

Both Cy5 and Cy7 fluorescence intensity increased with SDM-25 dose in both excised lumpectomy tissue and lymph nodes, as shown in FIG. 8A-FIG. 8B. FIG. 8A: primary lumpectomy specimens; plot of average Cy5 and Cy7 intensities for excised primary specimen tissue versus dose. The values were generated from the whole excised specimen. FIG. 8B: negative lymph node packets; plot of average Cy5 and Cy7 intensities for negative lymph nodes for each cohort in the study. The values were generated from the whole excised specimen. The error bars indicate standard deviations. Using only the fluorescence ratio data, the fluorescence ratio data for malignant primary tumor was significantly different than that for adjacent tissue for both same day and prior day dosing with SDM-25 (FIG. 9).

Example 2—Diagnostic Methods Based on Fluorescence Thresholds

Image analysis-based predictions of where cancer might occur were made by choosing areas where Cy5/Cy7 fluorescence ratio and Cy5 intensity were high for primary specimen images collected as described in Example 1. Automated predictions based on the use of Cy5/Cy7 ratio thresholds and/or Cy5 intensity thresholds in combination with a minimum size determination for the area above threshold value were generated using open source ImageJ software developed by the National Institutes of Health. The process, shown in FIG. 10, used image analysis to generate ROIs. Alternatively, user-selected ROIs could be used to generate predictions based on Cy5/Cy7 fluorescence and/or Cy5 intensity as shown in FIG. 11. For given thresholds of Cy5/Cy7 ratio and/or Cy5 intensity, a prediction of positive or negative is made. FIG. 11 shows a flow scheme that outlines the process for generating ROI from fluorescence ratio and individual intensity images. The method creates image masks based on fluorescence ratio threshold and/or a combination of fluorescence ratio threshold and individual fluorescence intensity thresholds. Combined application of the image masks is then used to generate ROI.

Example 3—Improving Diagnostic Performance Using Both Fluorescence Ratio and Intensity Values ROC Curve Analysis:

Receiver operator curve (ROC) analysis was used for determination of optimal Cy5/Cy7 fluorescence ratio thresholds, individual fluorescence intensity thresholds, and combined fluorescence intensity and ratio thresholds to improve prediction accuracy. ROC curves plot clinical sensitivity (or "true positive rate") versus (1−clinical specificity) (or "false positive rate"), and are routinely used to determine the clinical sensitivity and specificity of a diagnostic test. ROC curves were generated using the image analysis predictions described above that the imaged tissue samples would test positive or negative for cancer, as shown in flow scheme in FIG. 12.

Figure 13A:
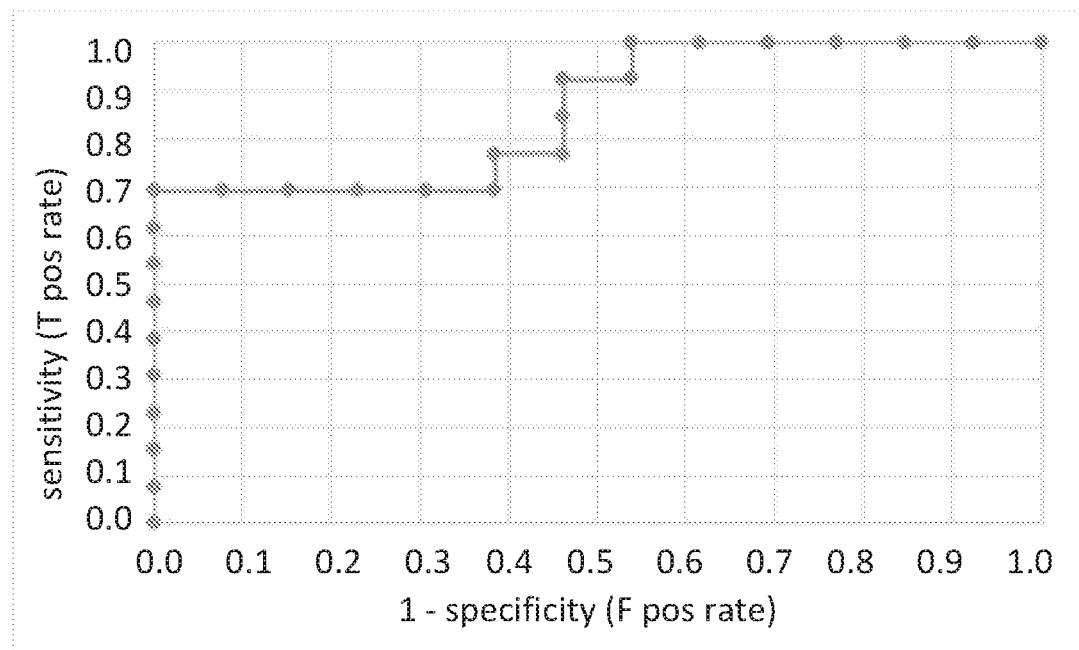
FIG. 13A-FIG. 13C provide examples of ROC curves for a primary tumor specimen from human patients infused with SDM-25 generated using different combinations of fluorescence ratio threshold and fluorescence intensity threshold.
Figure 13B:
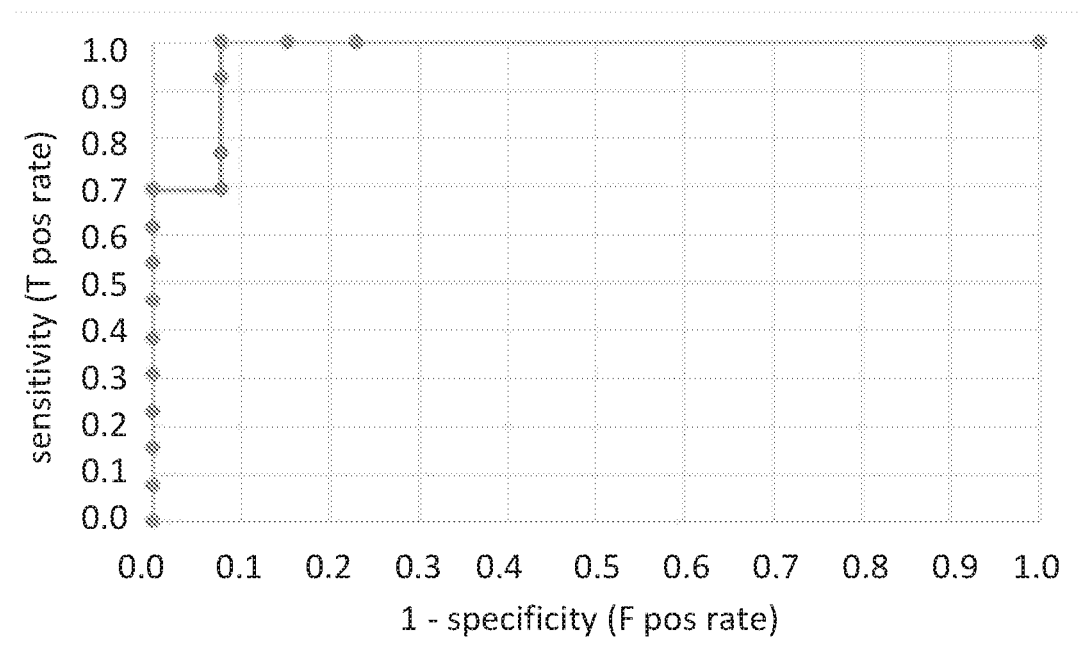
Figure 13C:
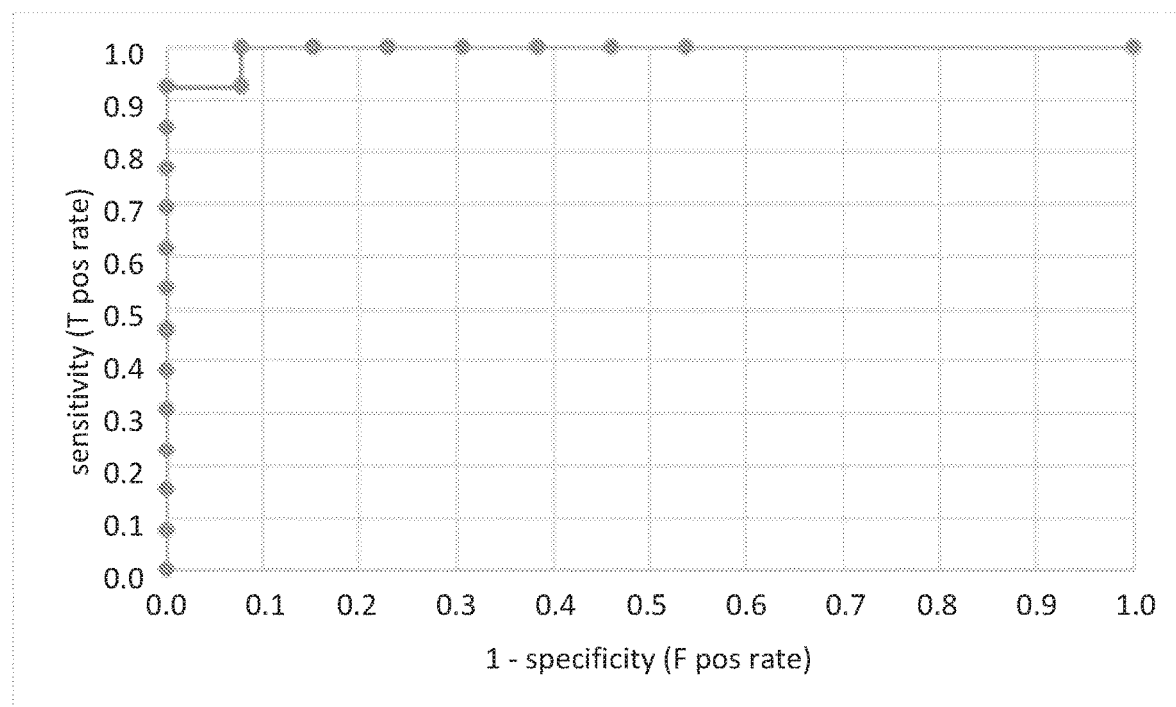

Primary Tumor Examples:

ROC curves were generated by comparing predictions from image analysis of primary specimen images using user-selected ROIs with gold standard pathology test results, which included pathologist assessments of hematoxylin and eosin (H&E) stained tissue sections, as shown in FIG. 11 and FIG. 12. The Cy5/Cy7 ratio and Cy5 intensity in ROIs were compared at different thresholds to generate pathology predictions. ROC curves were generated from threshold-based pathology predictions for combined high fluorescence ratio and high intensity area (assumed to be positive—prediction either true positive or false negative) and the lower Cy5/Cy7 ratio and lower Cy5 intensity adjacent area of the primary specimen (assumed to be negative—prediction either true negative or false positive). These assumptions were consistent with the pathology lab tests. Results are shown in FIG. 13A-FIG. 13C, which show that the highest prediction accuracy (highest "area under the curve" (AUC) for the ROC curve) utilized both Cy5/Cy7 fluorescence ratio and Cy5 intensity (FIG. 13C). FIG. 13A: ROC curve calculated by varying a fluorescence ratio threshold. Image data for all dosing times (i.e., same day, prior day) were analyzed collectively. The area under the curve (AUC)=0.86. FIG. 13B: ROC curve calculated by varying a fluorescence ratio threshold while a fluorescence intensity threshold was held fixed at value I=80; AUC=0.98. The original 8-bit intensity images were expanded to 16 bit image to normalize intensity to an exposure 500 ms. FIG. 13C: ROC curve calculated by varying a fluorescence intensity threshold while a fluorescence ratio threshold was held fixed at value R=60 (on an 8-bit image data scale of 0 to 255); AUC=0.99. In this case, the highest accuracy was achieved using a combination of fluorescence ratio and intensity thresholds.

Figure 14A:
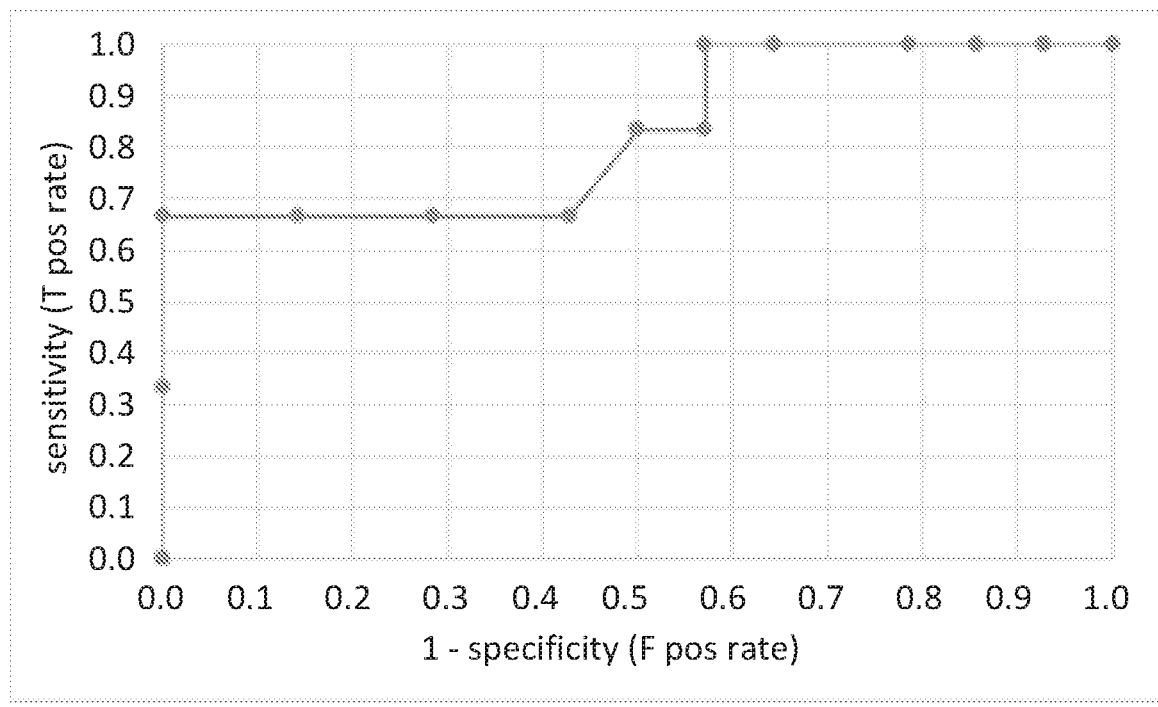
FIG. 14A-FIG. 14B provide examples of ROC curves for lymph node specimens from human patients infused with SDM-25 generated using different combinations of fluorescence ratio threshold and fluorescence intensity threshold.
Figure 14B:
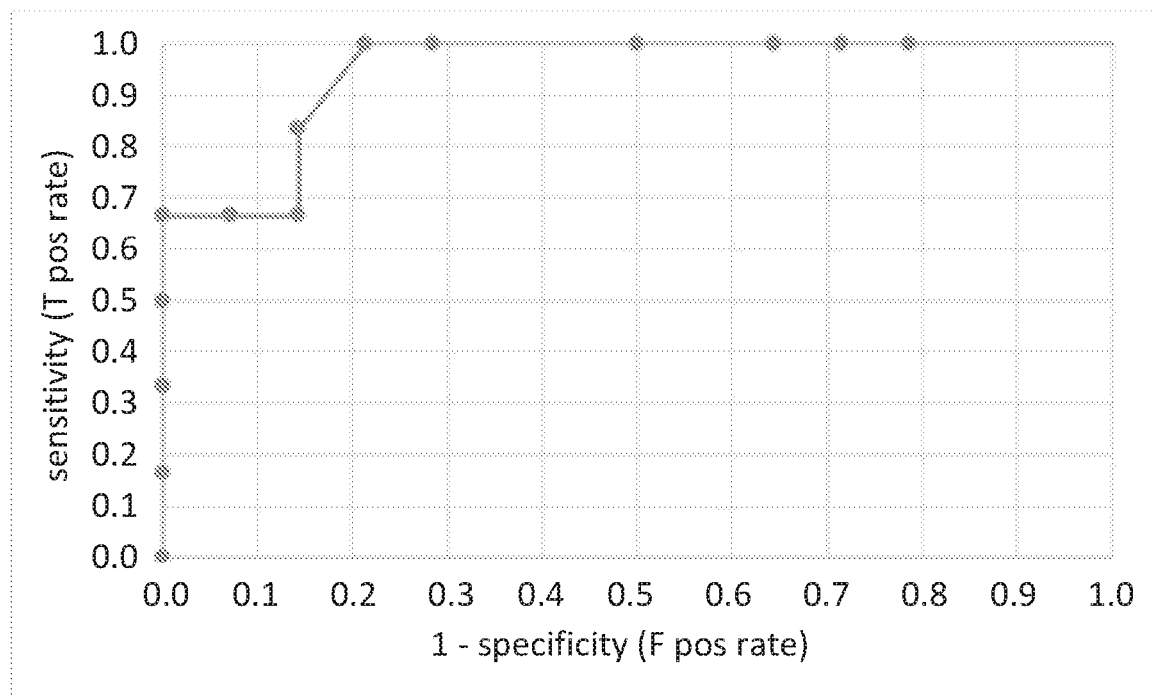

Lymph Node Examples:

The ROC curves shown in FIG. 14A-FIG. 14B for lymph node samples were generated using the image analysis processes illustrated in FIG. 7, FIG. 10, and FIG. 12 to predict whether the tissue was positive or negative for a given threshold. FIG. 14A: ROC curve calculated by varying a fluorescence ratio threshold varied; intensity threshold set at I≥10; AUC=0.83. FIG. 14B: ROC curve calculated by varying a fluorescence ratio threshold; intensity threshold set at I≥60; AUC=0.95. In this case, the highest accuracy was achieved using a combination of fluorescence ratio and intensity thresholds.

Figure 15A:
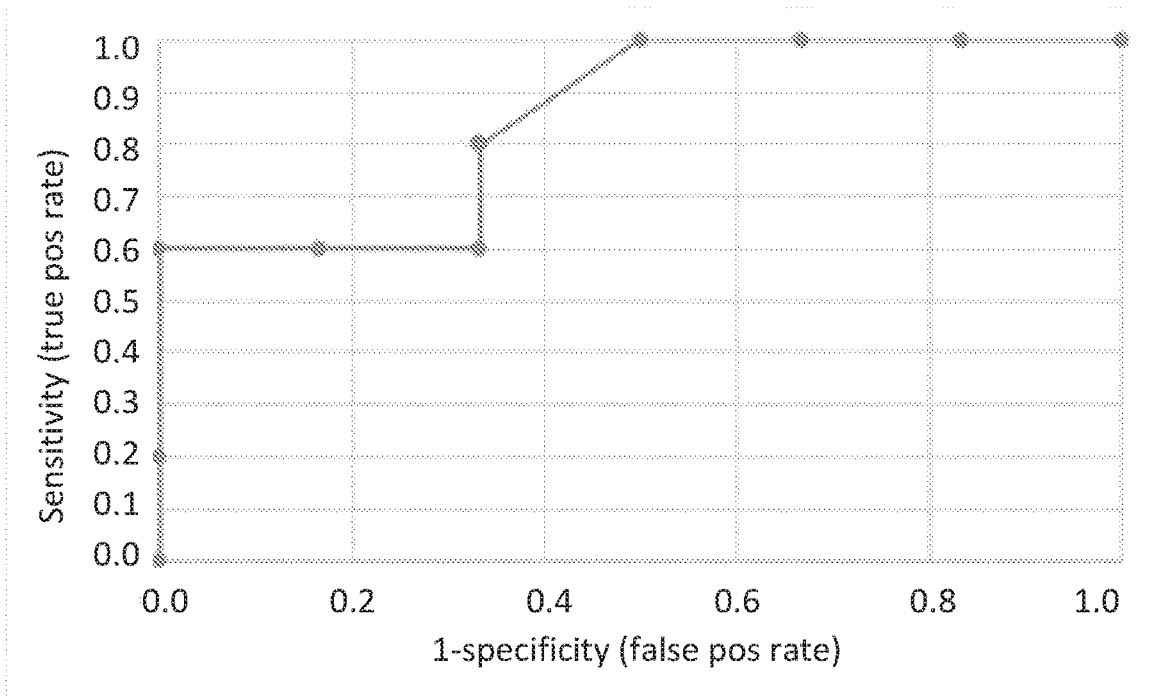
FIG. 15A-FIG. 15C provide examples of ROC curves for individual patient specimens infused with SDM-25 and generated using different combinations of fluorescence ratio threshold and fluorescence intensity threshold.
Figure 15B:
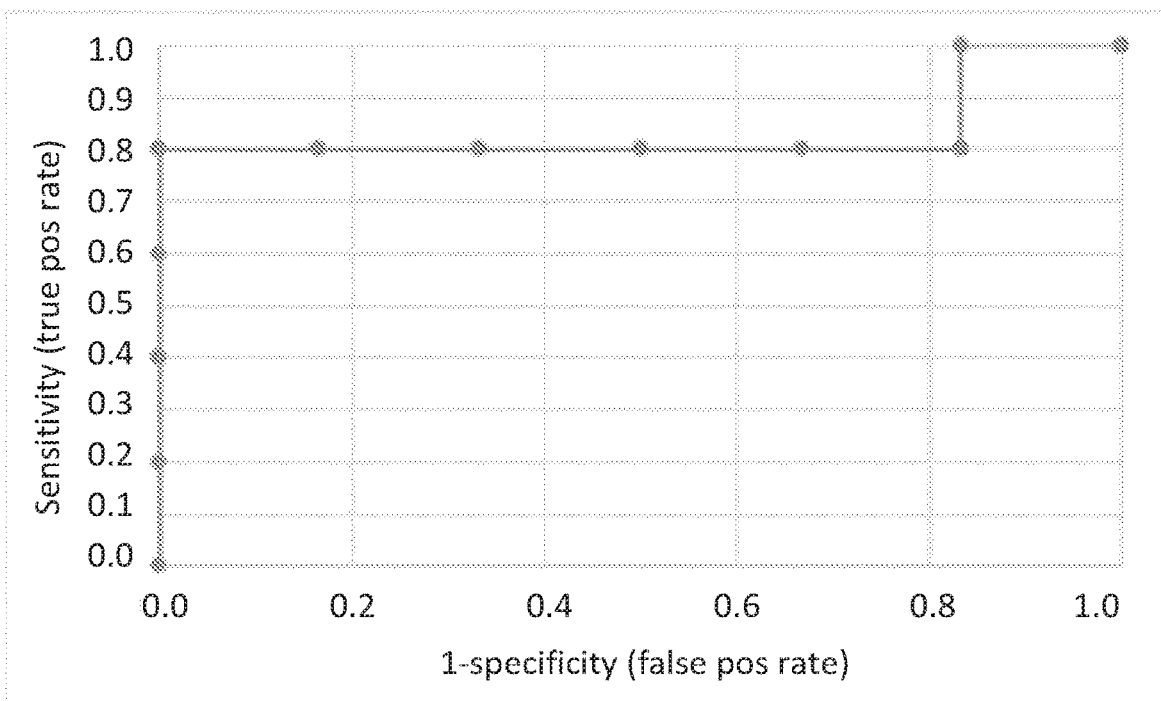
Figure 15C:
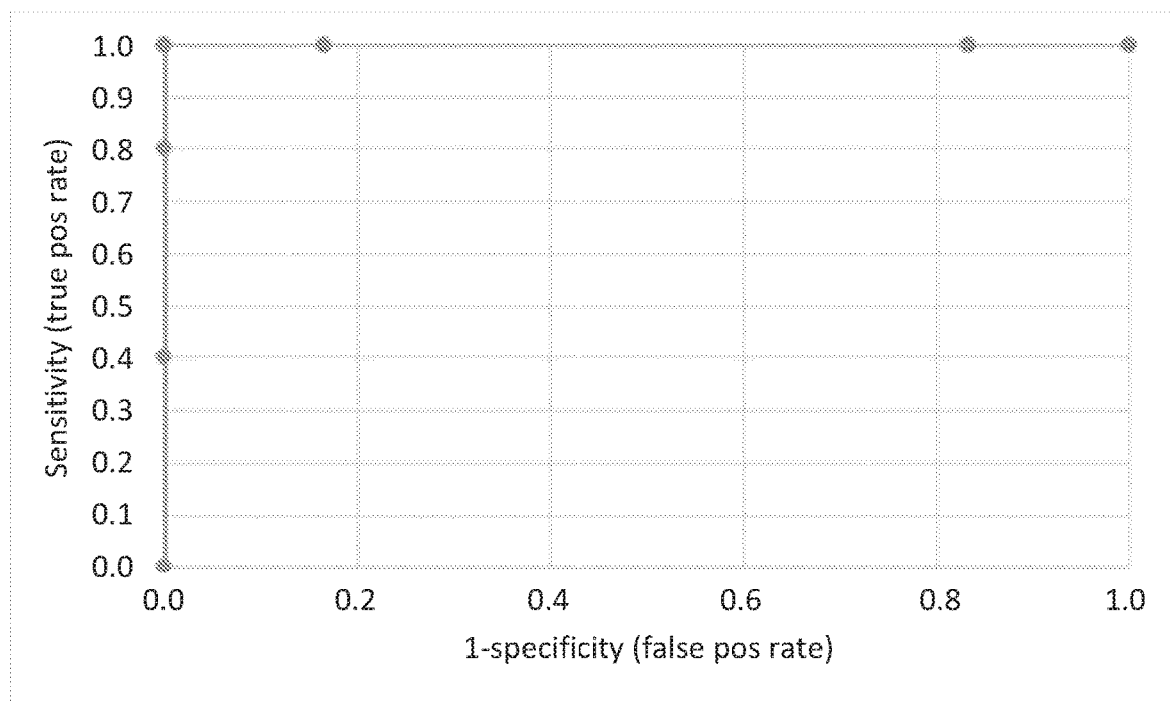

ROC curves are also be generated at the individual patient level. ROC curves for an individual patient are shown in FIG. 15A-FIG. 15C, and were generated using the image analysis process work flows illustrated in FIG. 7, FIG. 10, and FIG. 12 to predict whether the tissue was positive or negative for a given threshold. Ex vivo tissue samples that were imaged included primary specimen, lymph nodes, and margins. FIG. 15A: Fluorescence ratio threshold ROC curve for individual patient (fluorescence intensity threshold set to I≥5), AUC=0.85. FIG. 15B: Fluorescence intensity threshold ROC curve (fluorescence ratio threshold set to R≥5), AUC=0.83. FIG. 15C: Combined fluorescence ratio and fluorescence intensity ROC curve for an individual patient; the fluorescence ratio threshold was increased as the fluorescence intensity threshold was held fixed at I=85, AUC=1.00. In this case, the highest accuracy was again achieved using a combination of fluorescence ratio and intensity thresholds.

Clinical Study:

Patients were dosed with 8 mg of SDM-25 the day before surgery (DBD). The imaging and analysis methodology was based on the method described above.

Lumpectomy Surfaces and Margin Shaves Examples from Clinical Study:

The ROC curves were for generated for excised lumpectomy surfaces and shave margin samples taken from surgical cavity using the image analysis processes illustrated in FIGS. 7, 10, and 12 to predict whether the tissue was positive or negative for a given threshold. All specimens and surfaces data were correlated with pathology results. The ROC Area under the Curve (AUC) results, which is a measure of accuracy, are given in Table 1 below.

| Method | Surfaces DBD (ROC AUC %) | Shaves DBD (ROC AUC %) |
| --- | --- | --- |
| Ratio + Intensity | 63 | 67 |
| Intensity | 54 | 57 |
| Ratio | 57 | 57 |

In both of these tissue specimens illustrated in Table 1, the highest diagnostic performance or accuracy was achieved using a combination of fluorescence ratio and intensity thresholds.

Example 4—Images Displaying Predicted Cancerous Activity in Human Breast Cancer Excised from Patients Dosed with SDM-25

Figure 16:
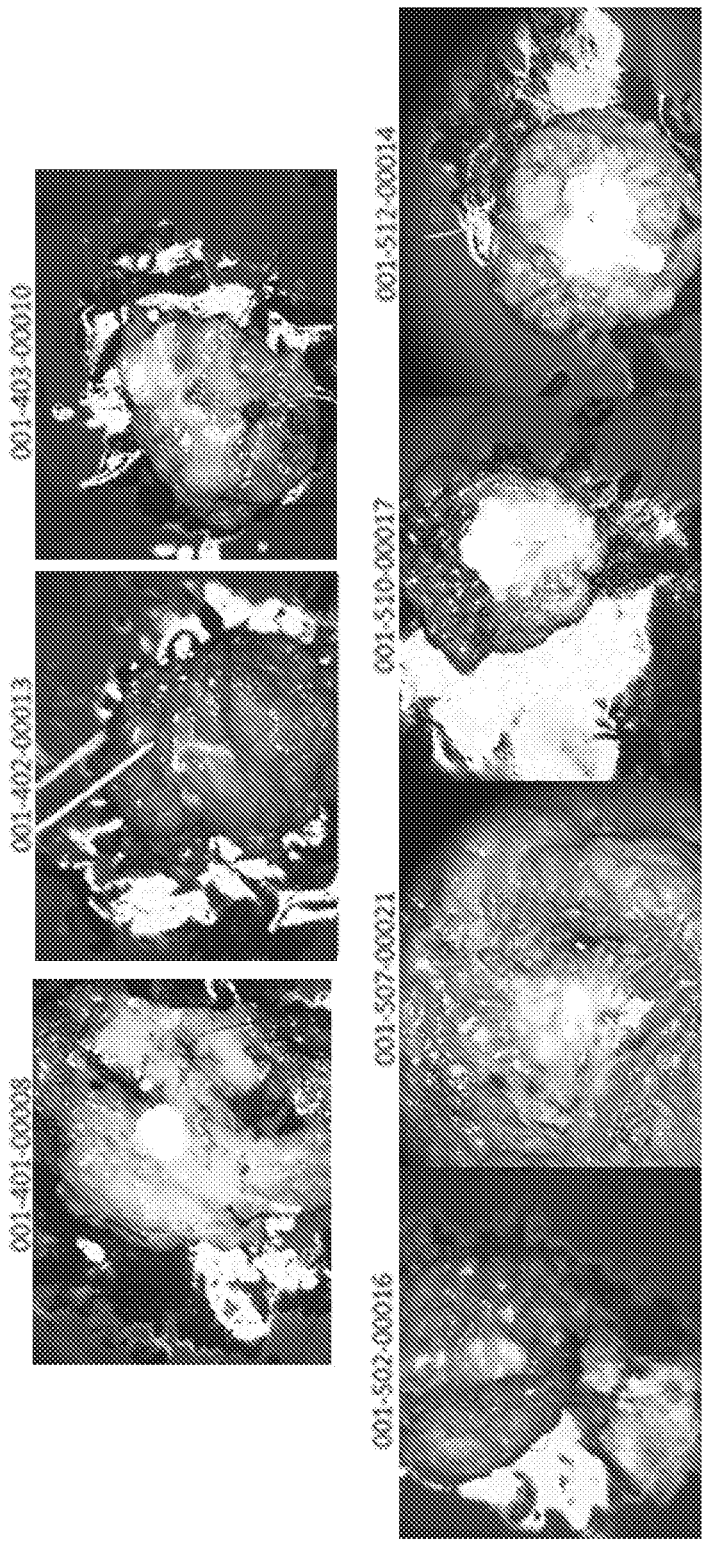
FIG. 16 provides examples of transected primary tumor specimen images from patients administered an 8 mg dose of SDM-25, where the imaging was performed the day after infusion. The white color indicates a Cy5/Cy7 fluorescence ratio threshold of R≥120 and a Cy5 intensity threshold of I≥50. The threshold values were determined using the described methods.

The method objective was to visually indicate the presence of cancer intra- or perioperative. Example images from study are shown in FIG. 16. Regions of images where the Cy5/Cy7 ratio and Cy5 intensity are above specific threshold values were determined using the methods described above are colored green. A different Cy5/Cy7 ratio threshold value was used for images taken the same day as infusion than the one used for images taken the day after infusion. Both ratio and intensity threshold values are based on the 8-bit image display of pixel values from 0 to 255 generated from camera. Cy5 intensity threshold values could be input without conversion by moving the Cy5 threshold slider in display software. Ratio threshold values (8-bit) were converted to a percentage (100×(threshold/255)) and entered by moving the slider labeled background in the software viewer. Cy5 intensity threshold values were not corrected for exposure or intensity differences.

Example 5—Images Displaying Predicted Cancerous Activity in Primary Lumpectomy Specimens Excised from Patients Dosed with SDM-25

Positive Lumpectomy Surface Margin Examples.

Figure 19A:
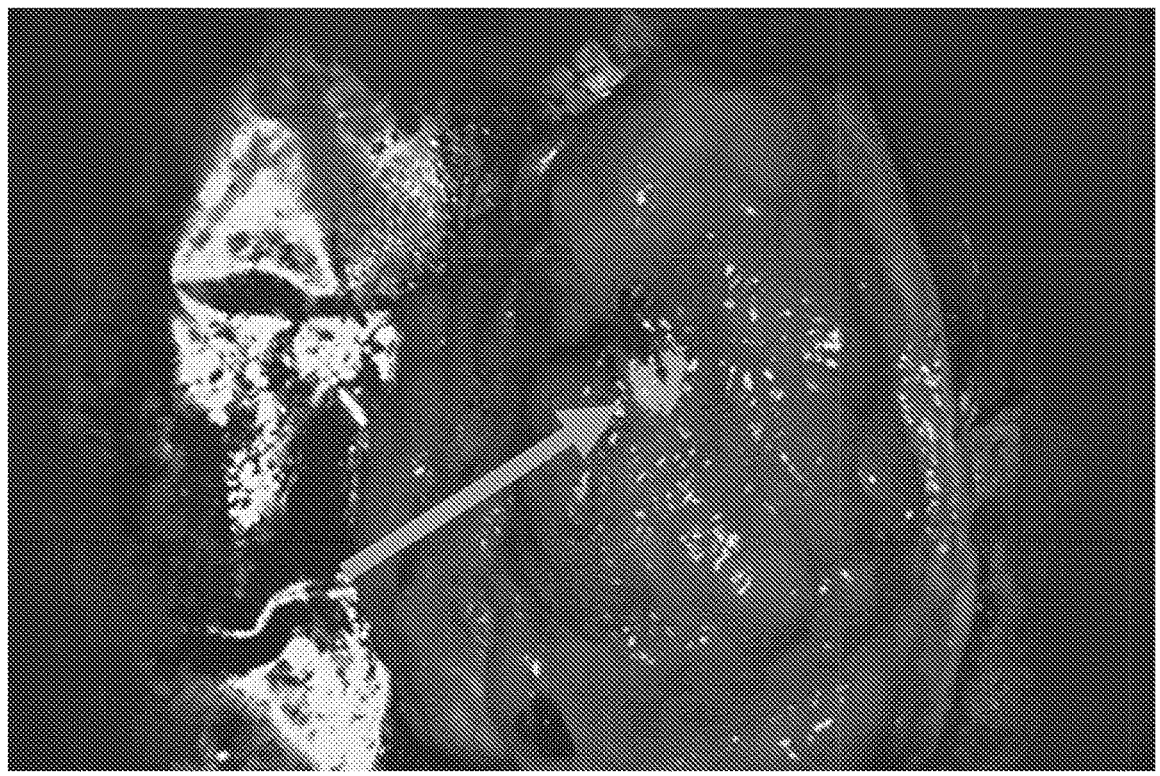
FIG. 19A provides a first example of surface margins of primary lumpectomy specimen images from patients administered an 8 mg dose of SDM-25, where the imaging was performed the day after infusion.
Figure 19B:
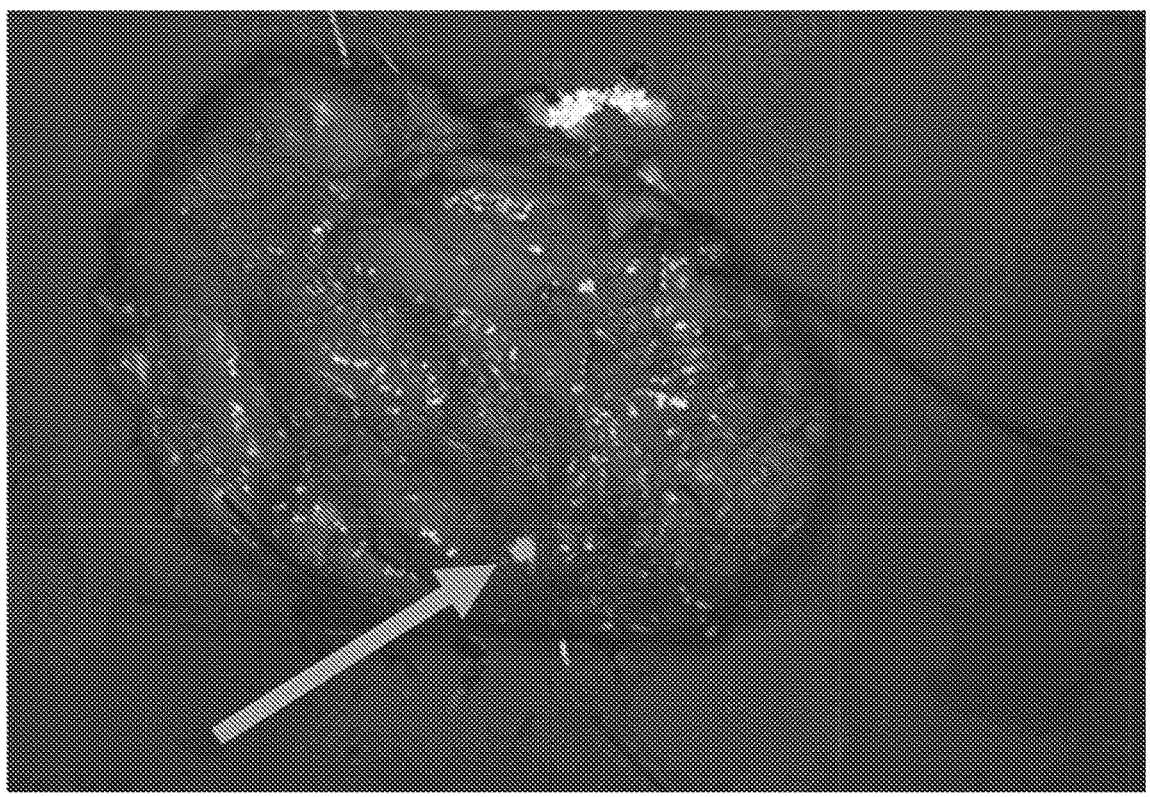
FIG. 19B provides a second example of surface margins of primary lumpectomy specimen images from patients administered an 8 mg dose of SDM-25, where the imaging was performed the day after infusion.

Example images are shown in FIG. 19A-FIG. 19B of the surfaces of surgically-removed primary lumpectomy specimens demonstrated by pathology to be positive for carcinoma. Regions of images where the Cy5/Cy7 ratio and Cy5 intensity are above specified threshold values were determined using ImageJ software using the methods described above and are again colored light gray. The arrow points to region above threshold which corresponds to surface face has cancer demonstrated by pathology. In this example Cy5 intensity threshold values were corrected for exposure using ImageJ software.

FIG. 19A and FIG. 19B provide examples of surface margins of primary specimen images from patients administered an 8 mg dose of SDM-25, where the imaging was performed the day after infusion. The light gray region indicates a Cy5/Cy7 fluorescence ratio threshold of R≥170 and a Cy5 intensity threshold of I≥50. The arrow points to region above threshold which corresponds to surface face has cancer demonstrated by pathology. The threshold values were determined using the described methods.

Example 6—Ratiometric Imaging in Mouse Model of Breast Cancer

In Vivo Mouse Model:

The mouse ear tumor model of lymphatic and cervical lymph node metastasis used for imaging agent evaluation was developed based on a modification of the method described for a melanoma model (Hoshida, et al. (2006), "Imaging Steps of Lymphatic Metastasis Reveals That Vascular Endothelial Growth Factor-C Increases Metastasis by Increasing Delivery of Cancer Cells to Lymph Nodes: Therapeutic Implications", Cancer Res. 66:8065-75). Metastatic 4T1 tumor cells from ATCC (CRL-2539™) were grown and suspended in DPBS/Matrigel™ (1:1 vol) and then injected subcutaneously ($4 \times 10^5$ tumor cells/50 mL/mouse) in female BALB/c mice on the right ear pinna above the auricular cartilage under ketamine-xylazine anesthesia. Ear tumor growth was followed by cervical lymph node metastasis by migration of cancer cells to lymph nodes. SDM-25 was tested using ear tumor-bearing mice 17 to 20 days (4T1 tumor model) post auricular tumor cell implantation. Tumor-bearing mice were randomly selected, restrained using the rotating tail injector (Braintree Scientific, Inc., MA) and dosed intravenously (tail vein) with SDM-25 solution (60 μM SDM-25; 100 μL/~20 grams mouse, i.e., 1.8 mg/kg body weight). After dosing, each tumor-bearing mouse was returned to its assigned housing cage and kept under controlled environmental conditions (food and water ad libitum) before being studied. A total of 30 4T1 tumor-bearing mice were examined at 3 h (N=9) and 6 h (N=21) post SDM-25 administration.

Imaging Procedures and Hardware:

Primary tumor and cervical lymph nodes were imaged in vivo in ear tumor-bearing mice terminally anesthetized with a mixture of Ketamine HCl/Xylazine HCl (100 mg/kg ketamine-10 mg/kg xylazine) administered intraperitoneally. Each mouse underwent a blunt dissection of ipsilateral (ear tumor side) and contralateral cervical lymph nodes. Following surgery, six major visible superficial cervical lymph nodes (including both ipsilateral and contralateral nodes) were identified, moisturized with physiological saline (0.9% Sodium Chloride Irrigation USP, B. Braun Medical Inc., Irvine, Calif.) and imaged using various systems including: a SZX10 fluorescence stereomicroscope (Olympus Optical, CO, Ltd, Tokyo, Japan) linked to a HCImage software system for image acquisition from Hamamatsu (Hamamatsu Photonics, K.K., Systems Division, Shizuoka-Pref, Japan); and a customized Navitar Imaging System (Navitar Inc, Rochester, N.Y.) interfaced with Spot Software 5.0 for image acquisition SPOT™ Imaging Solutions, Sterling Heights, Mich.). All of the above-mentioned fluorescence imaging systems were equipped with an LED light source emitting at ~630+/−20 nm to excite the Cy5 fluorophore, and two emission filters to separately capture Cy5 and Cy7 intensity images of same field of view.

Diagnostic Fluorescence Image Analysis:

Cervical lymph nodes were imaged and analyzed following SDM-25 administration in ear tumor-bearing mice. For each tumor-bearing mouse, Cy5 and Cy7 fluorescence images containing both ipsilateral and contralateral cervical lymph nodes were collected and used to make Cy5/Cy7 fluorescence ratio images. The ratio images were made by dividing the Cy5 image by the Cy7 image using the imaging processing program ImageJ. In some cases, an intensity-weighted pseudo-color ratio image was combined with a reflected light image, for display purposes. An ellipse or polygon region of interest (ROI) was drawn for each cervical lymph node and the individual averaged fluorescence intensities in ROI were measured. If the ratio was uniform in the examined lymph node, then the whole lymph node was used for the ROI. If there was a "hotspot" defined as a clearly defined region of higher fluorescence ratio (required to be >5% of the lymph node area) on the imaged cervical lymph node, then the smaller hotspot ROI was chosen for analysis. Average Cy5/Cy7 fluorescence ratios were calculated from each ROI.

For displaying the ratio images, the exposure-corrected Cy5 wavelength fluorescence image was divided by the exposure-corrected Cy7 emission wavelength imaged and multiplied by 15 so that the values for the ratio image fill the 8-bit dynamic range and lie between 0 and 255, as indicated below. A lookup table with RGB values assigned for each intensity level was then used to pseudo-color the ratio image. Pseudo-color ratio images were scaled for fluorescence intensity by multiplying the pseudo-color image by either the Cy5 or Cy7 wavelength fluorescence image resulting in images where hue or color represents the ratio and brightness represents fluorescence intensity.

$$\text{Display Ratio Image Value} = 15 \ast (I_{Cy5}/T_{Cy5})/(I_{Cy7}/T_{Cy7})$$

where:
$I_{Cy5}$=Cy5 wavelength fluorescence image intensity
$I_{Cy7}$=Cy7 wavelength fluorescence image intensity
$T_{Cy5}$=Cy5 exposure time
$T_{Cy7}$=Cy7 exposure time Comparison of the calculated fluorescence emission ratio and the lymph node pathologic status (presence/absence of cancer cells) as determined from H&E analysis of stained cervical lymph node sections were used to evaluate clinical sensitivity and specificity. Receiver Operating Characteristic (ROC) curves, which plot true positive fraction of positives (true positive rate) versus false positive fraction of negatives (false positive rate), were then constructed to determine the clinical sensitivity and specificity of SDM-25. For ROC curve analysis, data were divided into a binary classification of positives and negatives based on a threshold value for the fluorescence emission ratio.

True positives, false positives, true negatives, and false negatives were determined by comparing the prediction based on the fluorescence emission ratio data and threshold values from imaged cervical sentinel lymph nodes with the presence (positive) or absence (negative) of cancer cells determined by the pathologist using H&E stained tissue sections of imaged cervical lymph nodes.

The threshold value was gradually adjusted from low to high values to obtain a full ROC curve from (1, 1) or all positives to (0, 0) or all negatives. In practice, the ROC curve was generated by sorting the data and using threshold values just above the actual ratio values for each examined lymph node. An Excel spreadsheet using Boolean logic was used to calculate true positives, false negatives, true negatives and false positives for each point in the ROC curve. Sensitivity was calculated as the true positive rate, while specificity was calculated as one minus the false positive rate.

Histopathology:

After imaging, each mouse was terminally anesthetized and the cervical lymph nodes harvested and fixed in 10% buffered formalin. The terminally anesthetized mouse was immediately euthanized by intracardiac ketamine-xylazine overdose. After an overnight formalin fixation, cervical lymph nodes were processed for histology to assess the fluorescence/cancer correlation. Paraffin sections (5 µm) of cervical sentinel lymph nodes were obtained and processed for routine Hematoxylin & Eosin (H&E) staining performed by Zyagen (San Diego, Calif.) and HistoTox Labs, Inc. (Boulder, Colo.). Surgical pathology assessment, which was a classical determination of the presence/absence of metastatic cancer cells in the cervical lymph node tissues, was conducted by a certified anatomic and clinical pathologist at the VA San Diego Health Care System (San Diego, Calif.). H&E stained cervical lymph node sections were examined blinded using a Nikon Eclipse Microscope (Tochigi Nikon Precision Co., Ltd., Tochigi, Japan). The presence or absence of metastatic cancer cells in H&E sections was determined by applying standard histopathological criteria.

Example 7—In Vivo Diagnostic Imaging in Murine Metastatic Lymph Node Model

Figure 17A:
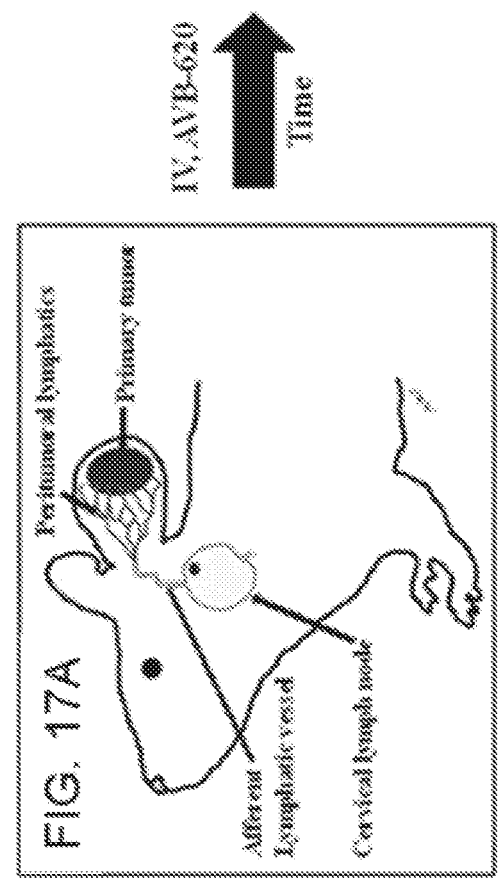
FIG. 17A-FIG. 17D provide a schematic illustration of a metastatic lymph node model and in vivo diagnostic imaging protocol. Breast cancer cells are implanted into a mouse ear and metastasize to the cervical lymph nodes (FIG. 17A). In order to evaluate the lymph node status, SDM-25 (AVB-620) is administered via a tail vein injection, and 3-6 hours later the cervical area is surgically exposed (FIG. 17B) and the lymph nodes are imaged. A fluorescence ratio image is obtained and displayed superimposed on a white light image using an RGB scale, where high fluorescence ratio is red and a low ratio is blue—an example shown in (FIG. 17C). The nodes are then surgically removed and processed for H&E histopathological analysis (FIG. 17D). The pathology results are directly compared to image ratio values using the RGB scale where red is equal to a high ratio. The red arrow indicates a metastatic (cancer positive) cervical lymph node fluorescently labeled by SDM-25 (AVB-620). Cyan colored arrows indicate cancer negative cervical lymph nodes as determined by histopathology.
Figure 17B:
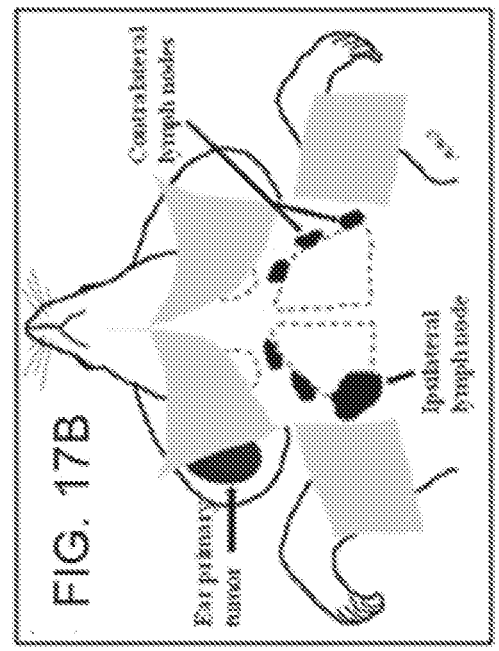
Figure 17C:
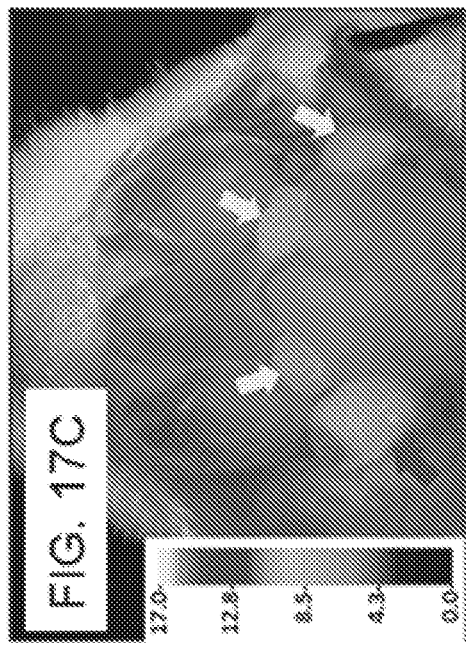
Figure 17D:
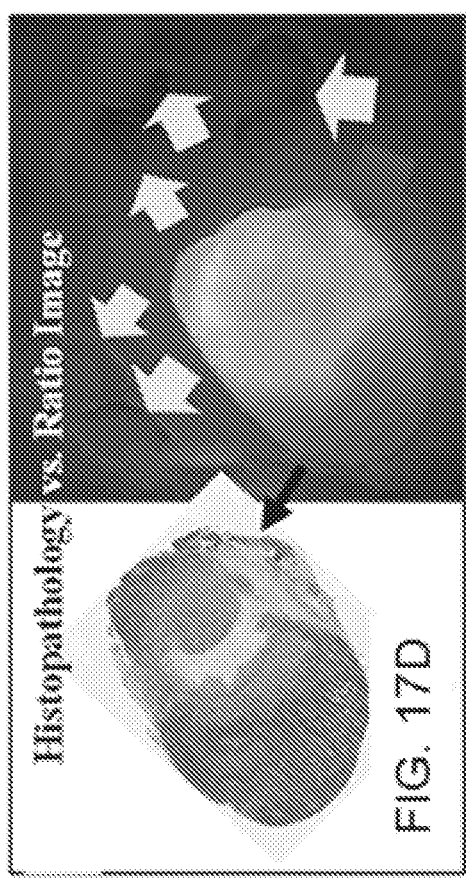
Figure 18A:
FIG. 18A-FIG. 18D show a comparison of fluorescence ratio imaging and histopathology using the murine 4T1 breast metastatic lymph node model.
Figure 18B:
Figure 18B:
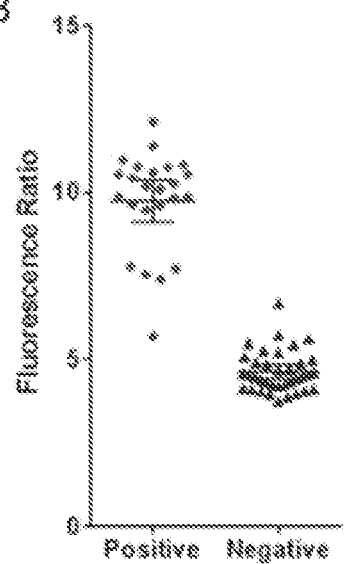
Figure 18C:
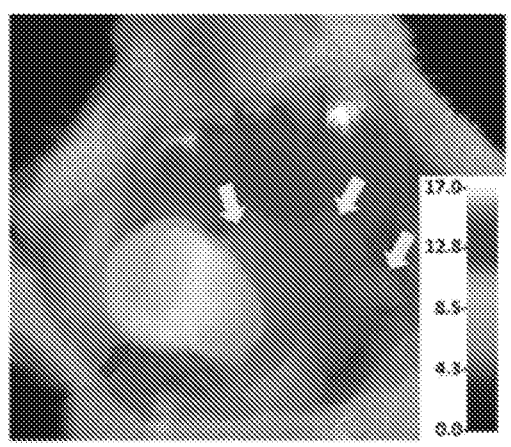

To evaluate SDM-25's ability to be activated in vivo and visualize breast cancer in lymph nodes, a murine metastatic breast cancer in lymph node models were used. A schematic of the experimental protocol is shown in FIG. 17A-FIG. 17D. Cancer cells were implanted in the ears of immuno-competent mice and after ~2 weeks metastasize to cervical lymph nodes (FIG. 17A). SDM-25 was administered and 3-6 h later the mice were anesthetized and cervical lymph nodes were surgically exposed, and imaged (FIG. 17B-FIG. 17C). Finally, the imaged lymph nodes were removed, processed for H&E pathology assessment, and imaging and pathology results were compared (FIG. 17D). In the first model, 30 female BALB/c mice bearing metastatic 4T1 breast cancer tumors on the ear pinna were dosed intravenously via tail vein injection with SDM-25 (6 nmol). The imaging dose was established from dose ranging studies from 2 to 24 nmol/mouse. The 6 nmol dose produced the largest Cy5/Cy7 fluorescence ratio difference between malignant and non-malignant lymph nodes, while still providing acceptable fluorescence intensity signal-to-background in both Cy5 and Cy7 images. Pre-surgical fluorescence imaging of dorsal, anterior view of mouse and surgically exposed cervical lymph nodes was performed after 3-6 h. The pre-surgical images show the primary tumor implanted in ear. A representative black and white image with and without superimposed fluorescence ratio images is shown in FIG. 18A. The images show that the pathology-confirmed primary tumor has high Cy5/Cy7 fluorescence ratio and intensity compared to the rest of the exposed body. After surgery, fluorescence ratio images of 60 lymph nodes were analyzed and compared to the results of a gold standard H&E histopathology test to assess imaging accuracy, the results are shown in FIG. 18B. The diagnostic sensitivity and specificity were 96% and 100% respectively using ratio thresholds from 6.7-7.4, which produced the highest overall accuracy of 98%. A representative image from one mouse is shown in FIG. 18C.

Figure 18D:
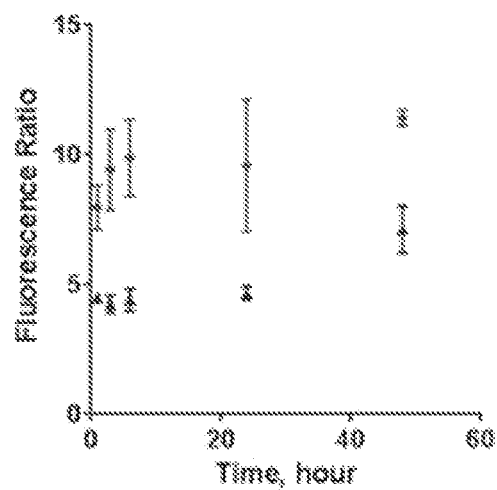

The kinetics and stability of the Cy5/Cy7 fluorescence ratio difference between cancer-free and metastatic lymph nodes was evaluated from 1 to 48 h after dosing with SDM-25. The results are shown in FIG. 18D. A significant fluorescence ratio difference is observed at 1 h ($p<0.02$, t-test) but is greatest at 3-6 h and is stable to 24 h. This useful time window is much greater than the SDM-25 plasma half-life in mice of 0.24 h. At 48 h the ratio difference is still significant ($p<0.01$, t-test) but reduced primarily due to a Cy5/Cy7 ratio increase in the uninvolved lymph nodes. This result is very different than that observed for r9e9 ratiometric ACPPs, which appear to have maximum contrast at 2 hours and show no difference between malignant and non-malignant tissue at 24 hours.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in any combination in practicing the invention. It is intended that the following claims define the scope of the invention and that methods and structures within the scope of these claims and their equivalents be covered thereby.

What is claimed is:

1. A method for detecting regions of biological activity in a biological specimen, the method comprising:
   a) contacting the biological specimen with a ratiometric fluorescent indicator of the biological activity;
   b) capturing a first fluorescence intensity image of the biological specimen at a first emission wavelength, and a second fluorescence intensity image of the biological specimen at a second emission wavelength;
   c) combining the first fluorescence intensity image and the second fluorescence intensity image to create a fluorescence ratio image;
   d) processing the fluorescence ratio image, the first fluorescence intensity image, the second fluorescence intensity image, or any combination thereof, using an image analysis algorithm to detect regions of biological activity, wherein the image analysis algorithm:
   i) uses a fluorescence ratio threshold, a first fluorescence intensity threshold, a second fluorescence intensity threshold, or any combination thereof, to create a mask image of the fluorescence ratio image, the first fluorescence intensity image, the second fluorescence intensity image, or any combination thereof,
   ii) performs an AND logical operation on two or more images selected from the group consisting of the mask image of the fluorescence ratio image, the mask image of the first fluorescence intensity image, and the mask image of the second fluorescence intensity image, if two or more mask images have been created in step (i), and
   iii) provides a classification of the biological specimen as either positive or negative for the biological activity, wherein the classification is based on a detection of a region of interest within the fluorescence ratio image, the first fluorescence intensity image, the second fluorescence intensity image, or the combination thereof that was used in step (i), that exhibits a fluorescence ratio value or a fluorescence intensity value that exceeds the value of the fluorescence ratio threshold, the first fluorescence intensity threshold, the second fluorescence intensity threshold, or the combination thereof that was used in step (i), and iv) stores the classification result in a computer memory.

2. The method of claim 1, further comprising displaying the region of interest within the fluorescence ratio image, the first fluorescence intensity image, the second fluorescence intensity image, or any combination thereof.

3. The method of claim 1, wherein the biological specimen is a cell sample, an ex vivo tissue sample, or an in vivo tissue sample.

4. The method of claim 1, wherein the biological activity to be detected is correlated with a disease, wherein the disease is arthritis, atherosclerosis, cancer, pre-cancer, or inflammation.

5. The method of claim 4, wherein the cancer is breast cancer.

6. The method of claim 1, wherein steps (b) to (d) are repeated two or more times at defined time intervals to provide a series of first fluorescence intensity images, second fluorescence intensity images, and fluorescence ratio images for monitoring a change in biological activity over time.

7. The method of claim 1, wherein the first fluorescence intensity image and the second fluorescence intensity image are captured using an endoscope, and the display of the region of interest is used to guide a positioning of the endoscope.

8. The method of claim 1, wherein the ratiometric fluorescent indicator is SDM-25, having the structure:

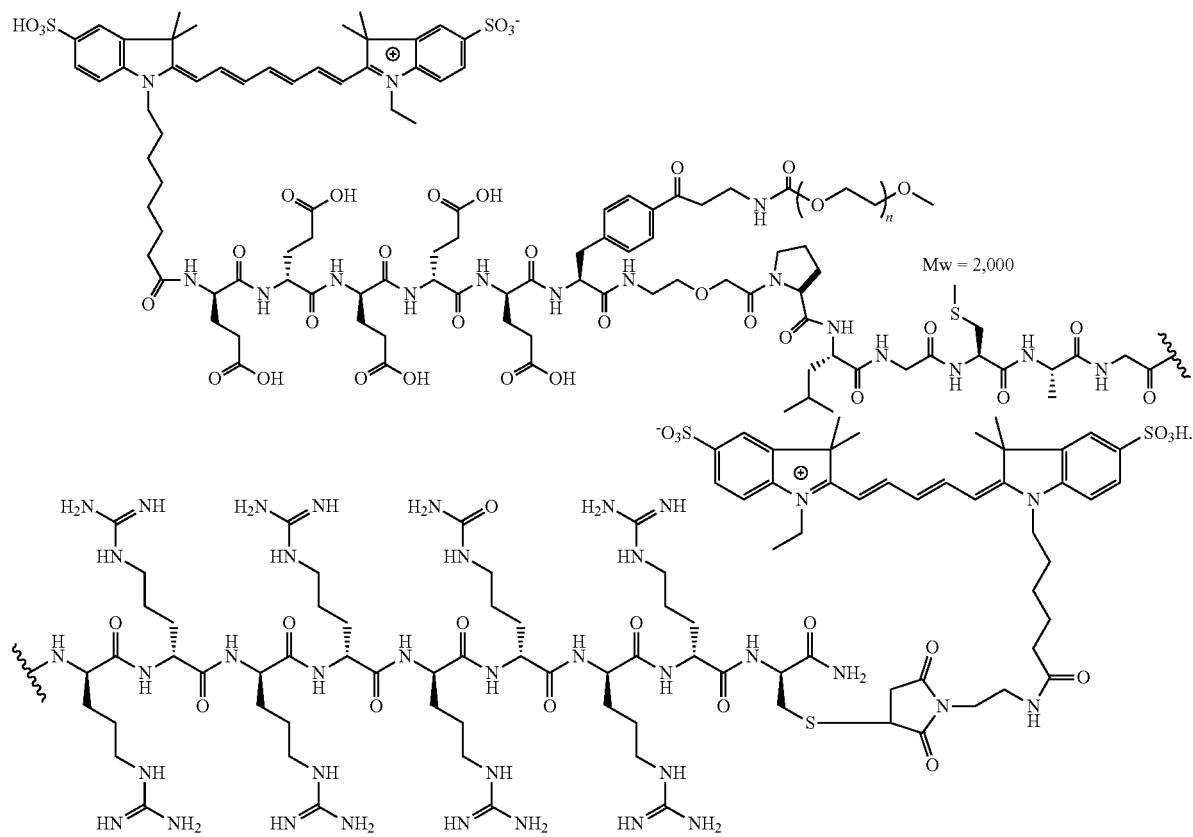

9. The method of claim 1, wherein the first and second fluorescence intensity images are normalized by image exposure time prior to creation of the fluorescence ratio image.

10. The method of claim 1, wherein a mean fluorescence ratio or a mean fluorescence intensity value within a region of interest provides a qualitative or quantitative measure of biological activity in the region of interest.

11. A method for automated optimization of fluorescence ratio and fluorescence intensity thresholds used to detect regions of biological activity in ratiometric fluorescence images of biological specimens, the method comprising:
 a) contacting a plurality of the biological specimens with a ratiometric fluorescent indicator of the biological activity;
 b) capturing a first fluorescence intensity image at a first emission wavelength and a second fluorescence intensity image at a second emission wavelength for each of the biological specimens;
 c) combining the first fluorescence intensity image and the second fluorescence intensity image to create a fluorescence ratio image for each of the biological specimens;
 d) providing a starting value for a first fluorescence intensity threshold, a second fluorescence intensity threshold, a fluorescence ratio threshold, or any combination thereof; and
 e) for each of the biological specimens: i) processing the fluorescence ratio image, the first fluorescence intensity image, the second fluorescence intensity image, or any combination thereof, using an image analysis algorithm, wherein the image analysis algorithm: uses the fluorescence ratio threshold, the first fluorescence intensity threshold, the second fluorescence intensity threshold, or any combination thereof, to create a mask image of the fluorescence ratio image, the first fluorescence intensity image, the second fluorescence intensity image, or any combination thereof, performs an AND logical operation on two or more images selected from the group consisting of the mask image of the fluorescence ratio image, the mask image of the first fluorescence intensity image, and the mask image of the second fluorescence intensity image, if two or more mask images have been created in the previous step, optionally checks that a detected region of interest within the fluorescence ratio image, the first fluorescence intensity image, the second fluorescence intensity image, or any combination thereof, is greater than a specified minimum size, wherein the detected region of interest is a region that exhibits a fluorescence ratio or a fluorescence intensity value that exceeds the value of the fluorescence ratio threshold, the first fluorescence intensity threshold, the second fluorescence intensity threshold, or any combination thereof, and provides a classification of the biological specimen as positive for the biological activity if a region of interest has been detected, or provides a classification of the biological specimen as negative for the biological activity if no region of interest has been detected; ii) comparing the classification provided by the image analysis algorithm with a pathology lab test result for the biological specimen to determine whether the classification is a true positive, false negative, true negative, or false positive; iii) storing the true positive, false negative, true negative, or false positive classification result in a computer memory; and f) repeating step (e) with: i) an incrementally increased value of the first fluorescence intensity threshold, while the second fluorescence intensity threshold and the fluorescence ratio threshold are held fixed until all of the biological specimens are classified as negative by the image processing algorithm, or ii) an incrementally increased value of the second fluorescence intensity threshold, while the first fluorescence intensity threshold and the fluorescence ratio threshold are held fixed until all of the biological specimens are classified as negative by the image processing algorithm, or iii) an incrementally increased value of the fluorescence ratio threshold, while the first fluorescence intensity threshold and the second fluorescence intensity threshold are held fixed until all of the biological specimens are classified as negative by the image processing algorithm;

g) calculating a receiver operator characteristic (ROC) curve using the stored classification results for each set of fluorescence ratio threshold, first fluorescence intensity threshold, and second fluorescence intensity threshold values; and h) comparing the area under the ROC curve for each set of fluorescence ratio threshold, first fluorescence intensity threshold, and second fluorescence intensity threshold values to determine an optimal setting for the fluorescence ratio threshold, the first fluorescence intensity threshold, the second fluorescence intensity threshold, or any combination thereof.

12. The method of claim 11, wherein the biological specimen is a cell sample, an ex vivo tissue sample, or an in vivo tissue sample.

13. The method of claim 11, wherein the biological activity to be detected is correlated with a disease, wherein the disease is arthritis, atherosclerosis, cancer, pre-cancer, or inflammation.

14. The method of claim 13, wherein the cancer is breast cancer.

15. The method of claim 11, wherein the ratiometric fluorescence indicator is SDM-25, having the structure:

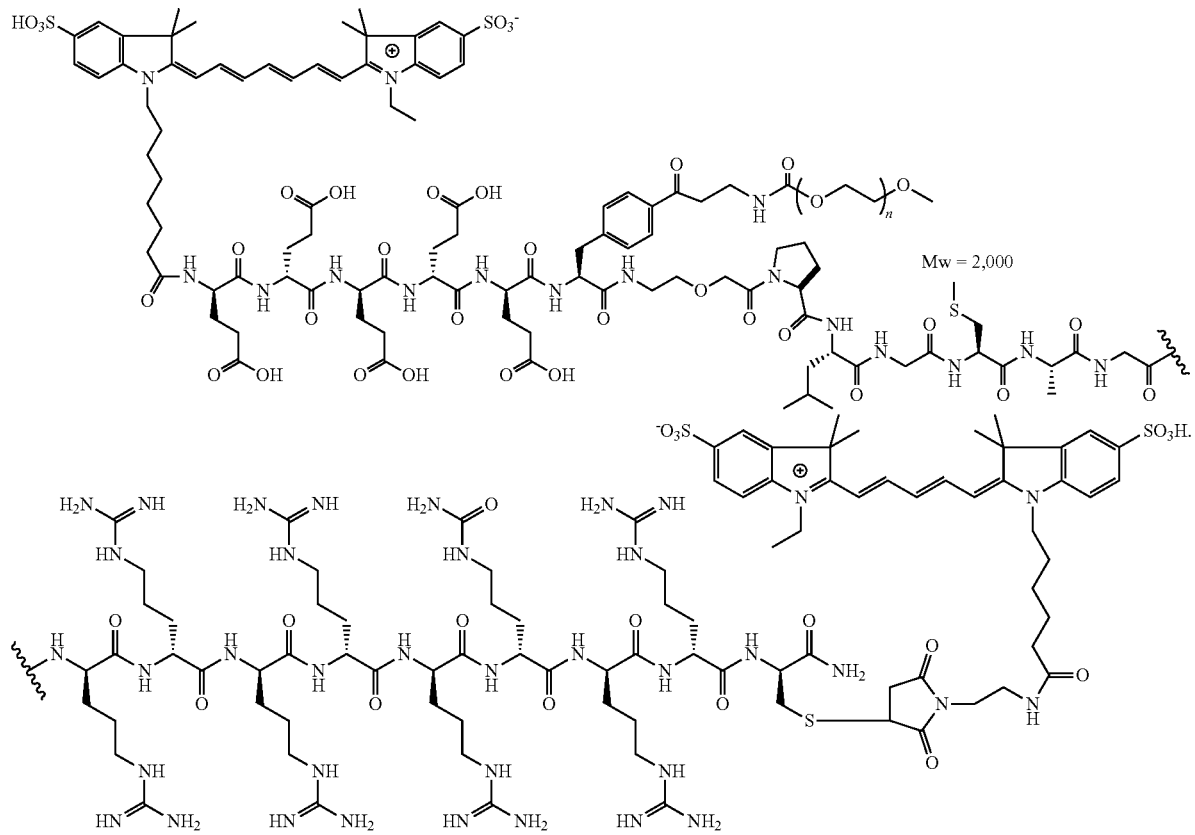

* * * * *